(12) United States Patent
Wu et al.

(10) Patent No.: US 11,649,245 B2
(45) Date of Patent: May 16, 2023

(54) CYCLOPROPYLAMINE COMPOUND AS LSD1 INHIBITOR AND USE THEREOF

(71) Applicants: HELIOEAST PHARMACEUTICAL CO., LTD., JiangXi (CN); Helioeast Science & Technology Co., Ltd., JiangXi (CN)

(72) Inventors: Lingyun Wu, Shanghai (CN); Qiuyan Wang, Shanghai (CN); Jian Li, Shanghai (CN); Shuhui Chen, Shanghai (CN)

(73) Assignees: HELIOEAST PHARMACEUTICAL CO., LTD., Nanchang (CN); Helioeast Science & Technology Co., Ltd., Nanchang (CN)

( * ) Notice: Subject to any disclaimer, the term of this patent is extended or adjusted under 35 U.S.C. 154(b) by 99 days.

(21) Appl. No.: 17/275,534

(22) PCT Filed: Sep. 12, 2019

(86) PCT No.: PCT/CN2019/105683
§ 371 (c)(1),
(2) Date: Mar. 11, 2021

(87) PCT Pub. No.: WO2020/052649
PCT Pub. Date: Mar. 19, 2020

(65) Prior Publication Data
US 2022/0119401 A1    Apr. 21, 2022

(30) Foreign Application Priority Data

Sep. 13, 2018 (CN) .......................... 201811070319.6
Jan. 31, 2019 (CN) .......................... 201910100629.6

(51) Int. Cl.
*C07D 491/107* (2006.01)
(52) U.S. Cl.
CPC ................................. *C07D 491/107* (2013.01)
(58) Field of Classification Search
CPC .................................................. C07D 491/107
See application file for complete search history.

(56) References Cited

U.S. PATENT DOCUMENTS

| 8,853,408 B2 | 10/2014 | Johnson et al. |
| 2014/0213657 A1 | 7/2014 | Munoz et al. |
| 2015/0025054 A1 | 1/2015 | Munoz et al. |
| 2018/0000805 A1 | 1/2018 | Johnson et al. |
| 2018/0354902 A1 | 12/2018 | Ortega Munoz et al. |

FOREIGN PATENT DOCUMENTS

| CN | 102947265 A | 2/2013 |
| CN | 103857393 A | 6/2014 |
| CN | 104203914 A | 12/2014 |
| JP | 2014515013 A | 6/2014 |
| JP | 2014532619 A | 12/2014 |
| WO | WO-2017027678 A1 | 2/2017 |
| WO | WO-2017195216 A1 | 11/2017 |
| WO | WO-2018081343 A1 | 5/2018 |

OTHER PUBLICATIONS

Chinese Office Action regarding Patent Application No. 201980060312.2, dated Jan. 29, 2022.
May 9, 2022 extended European search report issued in European Patent Application No. 19859831.0.
Apr. 26, 2022 First office action issued in Japanese Patent Application No. 2021514367.
International Search Report issued in International Patent Application No. PCT/CN2010/073565, dated Dec. 23, 2019.
Written Opinion of the International Searching Authority issued in International Patent Application No. PCT/CN2010/073565, dated Dec. 23, 2019.
Xueshun wang, et al., Medicinal chemistry insights in the discovery of novel LSD1 inhibitors—Epigenomics, vol. 7—No. 8, pp. 1379-1396, Dec. 8, 2015.
Adrian Bird, Perceptions of epigenetics—Nature, vol. 447—No. 7143, pp. 396-398, May 24, 2007.
James T Lynch, et al., LSD1 inhibition: a therapeutic strategy in cancer—Expert Opin Ther Targets, vol. 16—No. 12, pp. 1239-1249, Sep. 8, 2012.
Yujiang Shi, et al., Histone Demethylation Mediated by the Nuclear Amine Oxidase Homolog LSD1-Cell, vol. 119, pp. 941-953, Dec. 29, 2004.
Daniel P. Mould, et al., Reversible Inhibitors of LSD1 as Therapeutic Agents in Acute Myeloid Leukemia: Clinical Significance and Progress to Date—Med Res Rev, vol. 35—No. 3, pp. 586-618, Dec. 24, 2014.
Ruchi Anand, et al., Structure and Mechanism of Lysine-specific Demethylase Enzymes—Journal of Biological Chemistry, vol. 282—No. 49, pp. 35425-35429, Dec. 7, 2007.
Yong Chen, et al., Crystal structure of human histone lysine-specific demethylase 1 (LSD1)—Proc Natl Acad Sci U S A, vol. 103—No. 38, pp. 13956-13961, Sep. 19, 2006.
Eric Metzger, et al., LSD1 demethylates repressive histone marks to promote androgen-receptor-dependent transcription—Nature, vol. 437—No. 7057, pp. 436-439, Aug. 3, 2008.
Yi Chao Zheng, et al., A Systematic Review of Histone Lysine-Specific Demethylase 1 and Its Inhibitors, Medicinal Research Reviews, vol. 35—No. 5, pp. 1032-1071, May 19, 2015.

(Continued)

Primary Examiner — Rebecca L Anderson
(74) Attorney, Agent, or Firm — Harness, Dickey & Pierce, P.L.C.

(57) ABSTRACT

Provided is a cyclopropylamine compound as lysine-specific demethylase 1 (LSD1) inhibitor, and a use thereof in preparation of drug for treating diseases associated with LSD1. The cyclopropylamine compound is a compound represented by formula (I), an isomer thereof, and a pharmaceutically acceptable salt thereof.

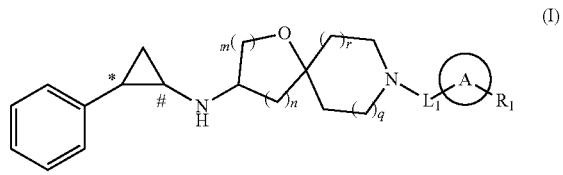

15 Claims, No Drawings

(56) References Cited

OTHER PUBLICATIONS

Zheng Y C, et al., TCPs: privileged scaffolds for identifying potent LSD1 inhibitors for cancer therapy—Epigenomics, vol. 8—No. 5, pp. 651-666, Apr. 2, 2016.

Pete Stavropoulos, et al., Crystal structure and mechanism of human lysine-specific demethylase-1—Nature Structral & Molecular Biology, vol. 13—No. 7, pp. 626-632, Jun. 25, 2006.

Yujiang Shi, et al., Histone Demethylation Mediated by the Nuclear Amine Oxidase Homolog LSD1—Cell, vol. 119—No. 7, pp. 941-953, Dec. 29, 2004.

Hosseini A, et al., A comprehensive review of lysine-specific demethylase 1 and its roles in cancer—Epigenomics, vol. 9—No. 8, pp. 1123-1142, Jul. 12, 2017.

CYCLOPROPYLAMINE COMPOUND AS LSD1 INHIBITOR AND USE THEREOF

CROSS-REFERENCE TO RELATED APPLICATIONS

This application is a U.S. National Phase Application under 35 U.S.C. 371 of International Application No. PCT/CN2019/105683, filed Sep. 12, 2019, which claims the benefit of Chinese Patent Application No. CN 201811070319.6, filed Sep. 13, 2018 and Chinese Patent Application No. CN 201910100629.6, filed Jan. 31, 2019.

TECHNICAL FIELD

The present disclosure relates to a class of cyclopropylamine compounds as lysine-specific demethylase 1 (LSD1) inhibitor, and use thereof in the preparation of a medicament for treating a disease associated with LSD1. Specifically, it relates to a compound of formula (I), an isomer thereof and a pharmaceutically acceptable salt thereof.

PRIOR ART

Post-translational modifications of histones includes processes of methylation, acetylation, phosphorylation, ubiquitination, and the like. They are important regulatory means of epigenetics, and can affect gene expression by changing the structure of chromatin [Xueshun Wang, Boshi Huang, Takayoshi Suzuki et al., Epigenomics, 2015, 1379-1396]. Although these modifications do not alter the underlying sequence of DNA, this epigenetic change may persist through cell division throughout the cell life cycle or cell iteration process [Adrian Bird, Nature, 2007, 396-398]. Therefore, epigenetic dysfunction is closely related to the pathological process of various diseases [James T Lynch, William J Harris & Tim C P Somervaille, Expert Opin. Ther. Targets, 2012, 1239-1249], such as various solid tumors, hematological tumors, viral infections, neurological abnormalities and other diseases. Therefore, epigenetics has now become a research hotspot in the field of drug research and development. The methylation status of histones is regulated by histone methyltransferase and histone demethylase. Lysine specific demethylase (Lysine specific demethylase 1, LSD1, also known as KDM1A) is the first reported histone lysine demethylase that regulates the methylation of histone lysine, it is widely involved in transcriptional regulation and affects many physiological processes such as cell proliferation and differentiation, embryonic stem cell pluripotency and the like. [Yujiang Shi, Fei Lan, Caitlin Matson et al., Cell, 2004, 941-953] [Daniel P. Mould, Alison E. McGonagle, Daniel H. Wiseman et al., Medicinal Research Reviews, 2015, 35, 586-618]. The LSD1 structure includes three main parts: the N-terminal SWIRM domain, the C-terminal aminooxidase domain (AOL) and the central Tower domain. [Ruchi Anand, Ronen Marmorstein, Journal of Biological Chemistry, 2007, 35425-35429]. The C-terminal aminooxidase domain includes two active pockets, one is the site for FAD binding, and the other is the site for recognition and binding to the substrate [Pete Stavropoulos, Gunter Blobel, André Hoelz, Nature Structral & Molecular Biology, 2006, 626-632]. There is no clear conclusion about the function of the SWIRM domain. It does not directly participate in the binding of FAD or substrates, but mutation or removal of this domain will reduce the activity of LSD1, therefore, it is speculated that this domain may affect the active region by adjusting its conformation. [Yong Chen, Yuting Yang, Feng Wang et al., Biochemistry, 2006, 13956-13961]. Tower domain is a binding domain of LSD1 and other protein factors. After LSD1 binds to different protein factors, it acts on different substrates and plays a different role in regulating histones and gene expression. For example, after LSD1 binds to CoREST, it will preferentially act on histone H3K4 through demethylation to remove activation-related histone markers and inhibit gene transcription; upon binding to the androgen receptor protein, recombinant LSD1 will act preferentially on H3K9 through demethylation to activate androgen receptor-related gene transcription [Ruchi Anand, Ronen Marmorstein, Journal of Biological Chemistry, 2007, 35425-35429; Eric Metzger, Melanie Wissmann, Na Yin et al., Nature, 2005, 436-439.]. In addition, LSD1 also regulates the methylation status of some non-histone substrates, including the tumor suppressor gene p53 and DNA methyltransferase 1 (DNMT1), etc., [Yi Chao Zheng, Jinlian Ma, Zhiru Wang, Medicinal Research Reviews, 2015, 1032-1071].

LSD1 is a FAD-dependent amino oxidase, in which proton transfer is considered the most likely oxidation mechanism [Zheng Y C, Yu B, Chen Z S, et al. Epigenomics, 2016, 8, 651-666.]. First, through proton transfer, the N—$CH_3$ bond of the substrate is converted into an imine bond, this imine ion intermediate undergoes a hydrolysis reaction to generate demethylated amine on one side and formaldehyde on the other side. During this catalytic cycle, FAD is reduced to FADH2, which is then oxidized back to FAD by a molecule of oxygen, and a molecule of $H_2O_2$ is generated at the same time. [Yujiang Shi, Fei Lan, Caitlin Matson, Cell, 2004, 941-953].

LSD1 is abnormally expressed in many different types of tumors. LSD1 is highly expressed in acute myeloid leukemia (AML) subtypes, and is an important factor in maintaining the potential of leukemia stem cells (LSC). LSD1 is highly expressed in a variety of solid tumors such as lung cancer, breast cancer, prostate cancer, liver cancer and pancreatic cancer, and is closely related to the poor prognosis of tumors. LSD1 inhibits the expression of cadherin, which is closely related to tumor invasion and epithelial-mesenchymal transition (EMT) [Hosseini A, Minucci S. Epigenomics, 2017, 9, 1123-1142.].

Currently, no drug as LSD1 inhibitor has been approved for marketing, and 8 drugs have entered the human clinical trial stage, mainly for the treatment of diseases such as hematological tumors, small cell lung cancer and Ewing's sarcoma. However, in the face of a huge unsatisfied market, this field still needs candidate compounds with better activity and pharmacokinetic parameters to advance clinical trials and meet the therapeutic needs.

Content of the Present Invention

The present disclosure has provided a compound of formula (I), an isomer thereof or a pharmaceutically acceptable salt thereof,

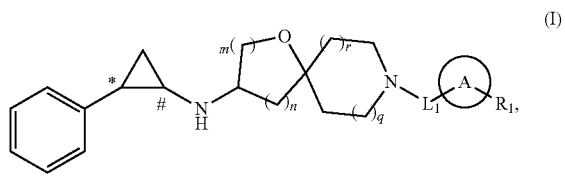

wherein, $L_1$ is selected from —$(CH_2)g$-, —C(=O)—NH—, —C(=O)— and —C(=O)—O—;

R₁ is selected from H, Cl, F, Br, I, OH, NH₂, CN, COOH, —C(═O)NH₂, $C_{1-6}$ alkyl, $C_{1-6}$ alkoxyl, —C(═O)NH—$C_{1-6}$ alkyl and 5-6 membered heteroaryl, wherein the $C_{1-6}$ alkyl, $C_{1-6}$ alkoxyl, —C(═O)NH—$C_{1-6}$ alkyl and 5-6 membered heteroaryl are optionally substituted by 1, 2 or 3 $R_a$;

ring A is selected from $C_{6-10}$ aryl, 5-6 membered heteroaryl, $C_{3-8}$ cycloalkyl and 3-6 membered heterocycloalkyl;

$R_a$ is selected from F, Cl, Br, I, OH, NH₂, CN, COOH and $C_{1-3}$ alkyl;

m is 0, 1 or 2;

n is 0, 1 or 2, and m and n are not 0 at the same time;

r is 0 or 1;

q is 0 or 1;

g is 0, 1, 2 or 3;

each of the 5-6 membered heteroaryl and 3-6 membered heterocycloalkyl comprises 1, 2, 3 or 4 heteroatoms or heteroatom groups independently selected from —NH—, —O—, —S— and N;

the carbon atom marked with "*" is a chiral carbon atom and exists in the form of (R) or (S) single enantiomer or enriched in one enantiomer;

the carbon atom marked with "#" is a chiral carbon atom and exists in the form of (R) or (S) single enantiomer or enriched in one enantiomer.

In some embodiments of the present disclosure, $R_a$ is selected from F, Cl, Br, I, OH, NH₂, CN, COOH and —CH₃, the other variables are as defined in the present disclosure.

In some embodiments of the present disclosure, R₁ is selected from H, C₁, F, Br, I, OH, NH₂, CN, COOH, —C(═O)NH₂, $C_{1-3}$ alkyl, $C_{1-3}$ alkoxyl, —C(═O)NH₂—$C_{1-3}$ alkyl and 5 membered heteroaryl, wherein the $C_{1-3}$ alkyl, $C_{1-3}$ alkoxyl, —C(═O)NH₂—$C_1$-3 alkyl and 5 membered heteroaryl are optionally substituted by 1, 2 or 3 $R_a$, the other variables are as defined in the present disclosure.

In some embodiments of the present disclosure, R₁ is selected from H, F, C₁, Br, I, OH, NH₂, CN, COOH, —C(═O)NH₂, —CH₃, —OCH₃ and tetrazolyl, wherein the —CH₃, —OCH₃ and tetrazolyl are optionally substituted by 1, 2 or 3 $R_a$, the other variables are as defined in the present disclosure.

In some embodiments of the present disclosure, R₁ is selected from H, F, C₁, Br, I, OH, NH₂, CN, COOH, —C(═O)NH₂, —CF₃, —OCH₃, —CH₂—COOH and

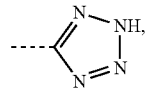

the other variables are as defined in the present disclosure.

In some embodiments of the present disclosure, L₁ is selected from a single bond, —CH₂—, —(CH₂)₂—, —C(═O)—NH—, —C(═O)— and —C(═O)—O—, the other variables are as defined in the present disclosure.

In some embodiments of the present disclosure, ring A is selected from phenyl, naphthyl, tetrazolyl, pyridyl, pyrazinyl, cyclopropyl, cyclobutyl, cyclohexyl, bicyclo[2.2.2]octyl and azetidinyl, the other variables are as defined in the present disclosure.

In some embodiments of the present disclosure, ring A is selected from

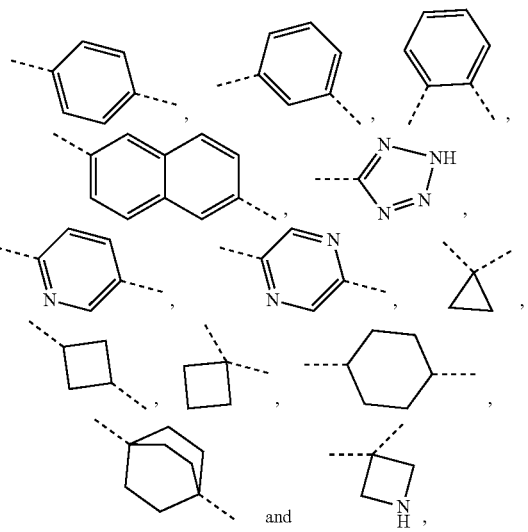

the other variables are as defined in the present disclosure.

In some embodiments of the present disclosure, the moiety

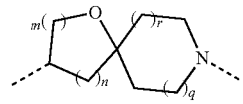

is selected from

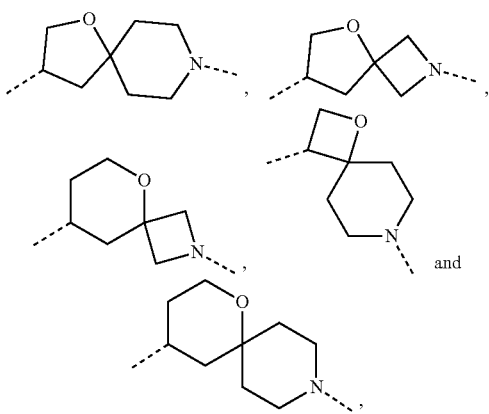

the other variables are as defined in the present disclosure.

In some embodiments of the present disclosure, the moiety

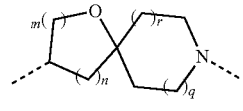

is selected from

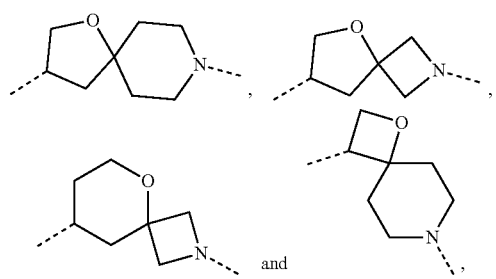

and the other variables are as defined in the present disclosure.

There are also some embodiments of the present disclosure that come from arbitrary combination of the above variables.

In some embodiments of the present disclosure, the compound, the isomer thereof or the pharmaceutically acceptable salt thereof, the compound is selected from (I-1)
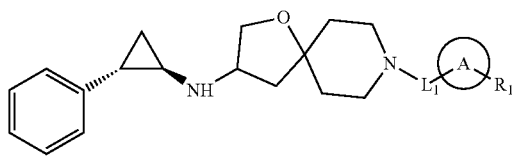

(I-2)
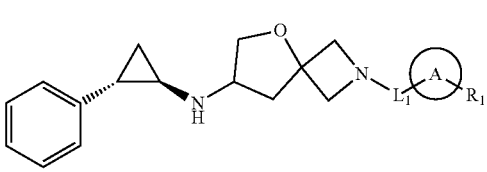

(I-3)
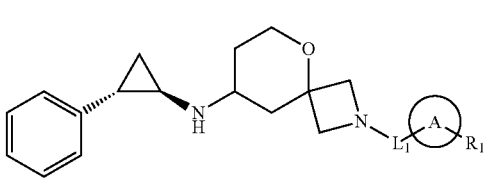

(I-4)
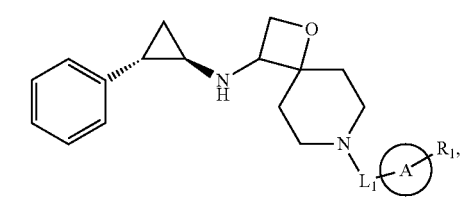

wherein, $R_1$, $L_1$ and ring A are as defined in the present disclosure.

In some embodiments of the present disclosure, the compound, the isomer thereof or the pharmaceutically acceptable salt thereof, the compound is selected from (I-1A)
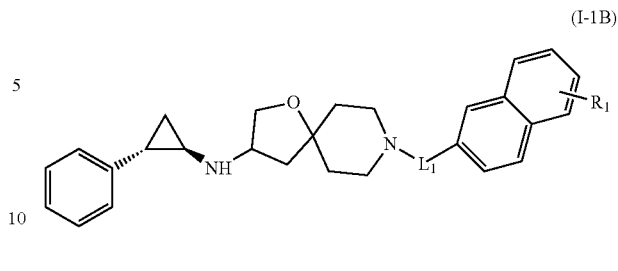

(I-1B)
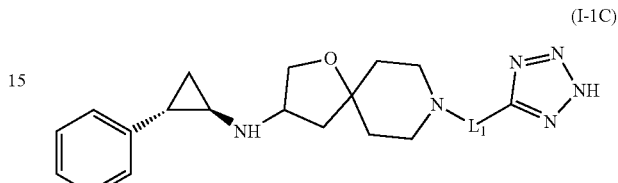

(I-1C)
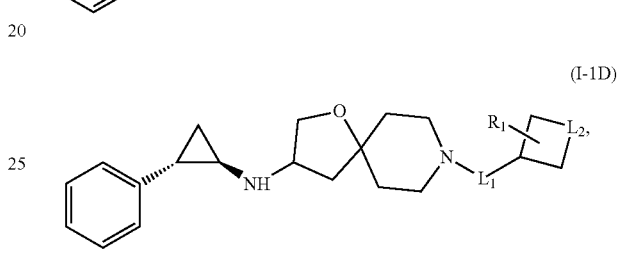

(I-1D)
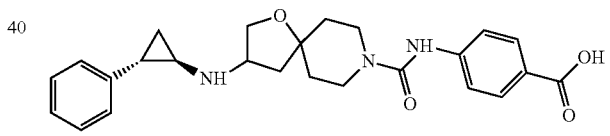

wherein,

L2 is selected from a single bond, —$CH_2$—, —$(CH_2)_2$—, —$(CH_2)_3$— and —NH—;

$R_1$ and $L_1$ are as defined in the present disclosure.

The present disclosure also provided a compound of the following formula, an isomer thereof or a pharmaceutically acceptable salt thereof

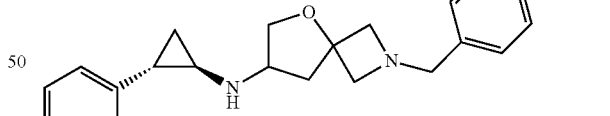

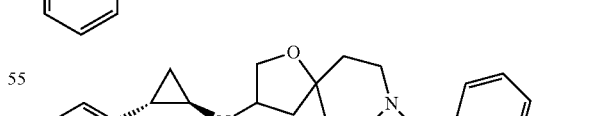

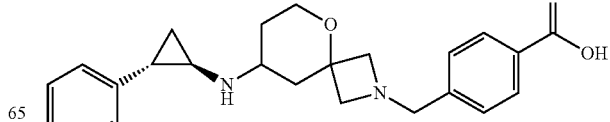

-continued
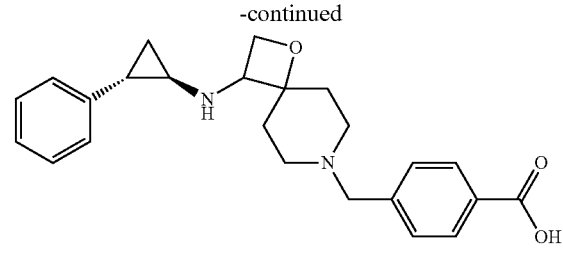
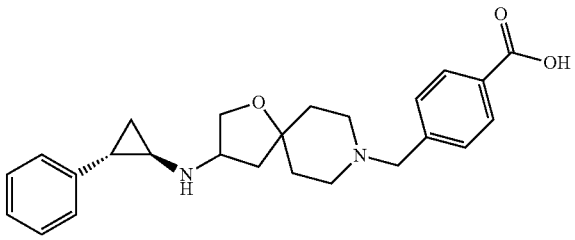
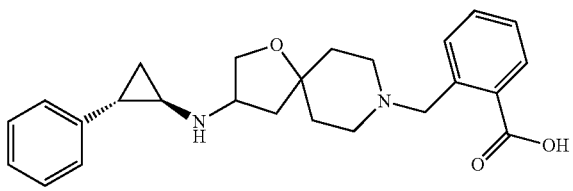
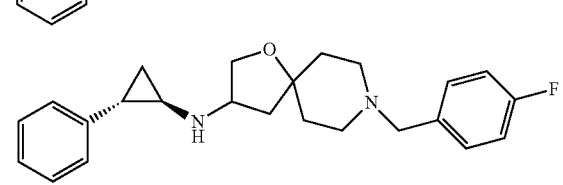
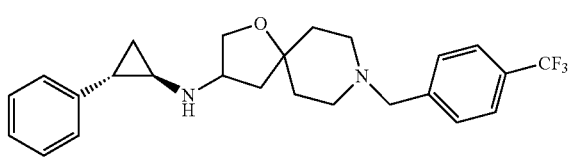
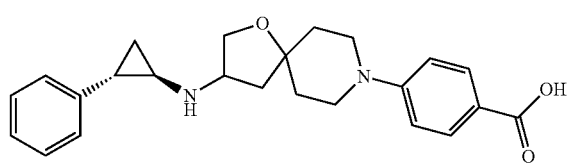
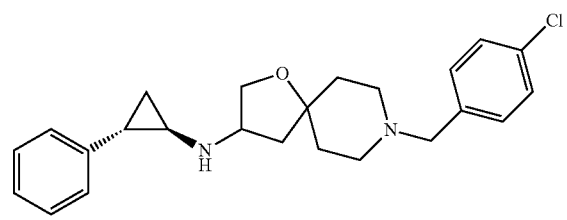
-continued
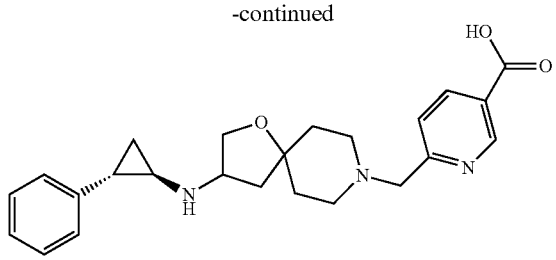
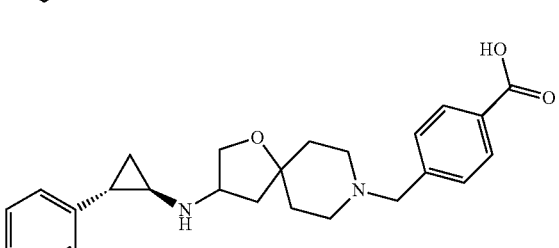
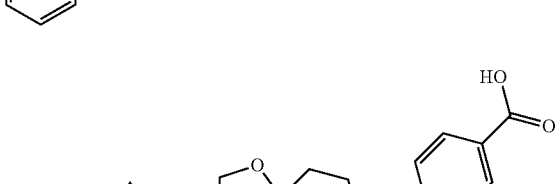
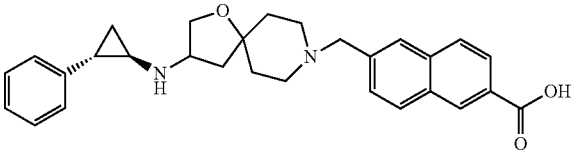
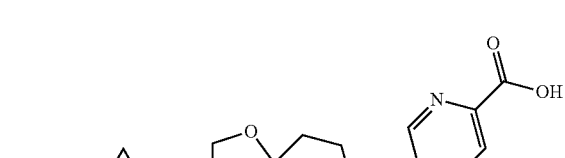
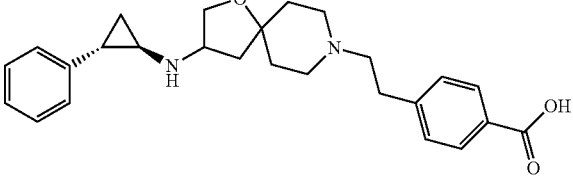
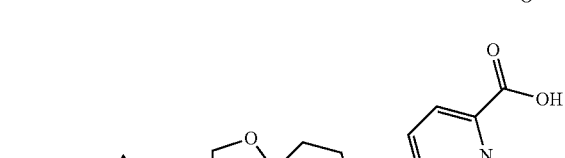

9
-continued
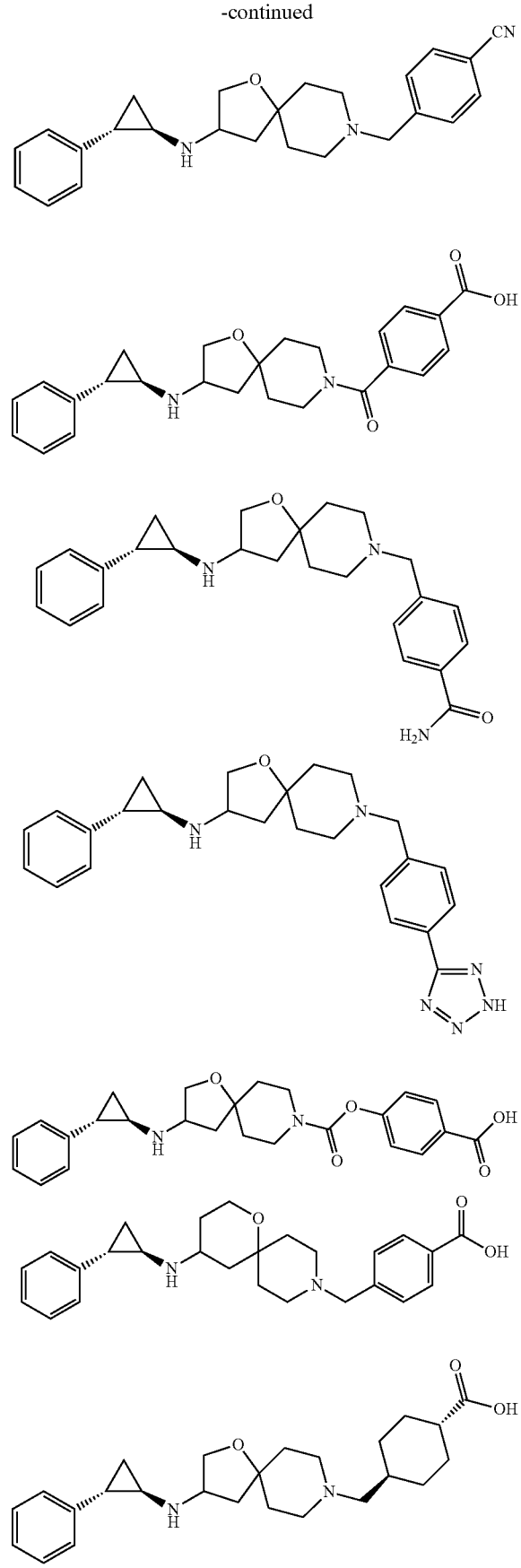
10
-continued
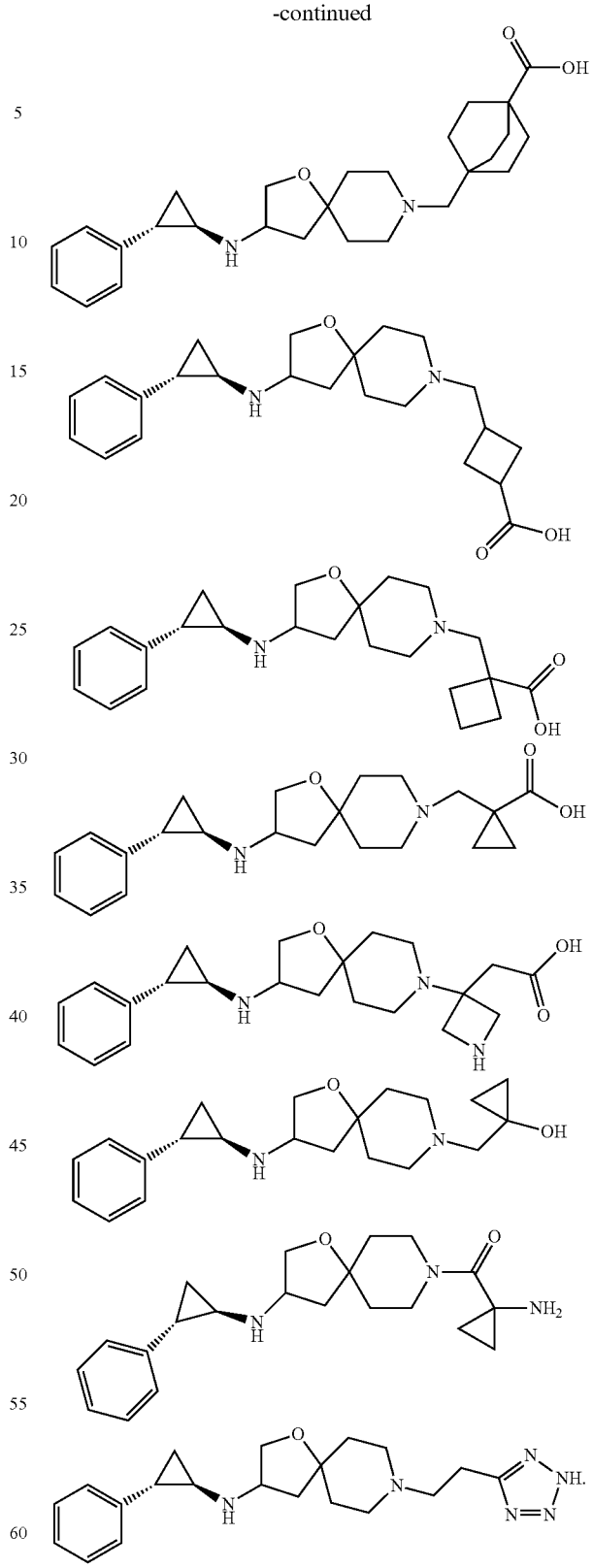
In some embodiments of the present disclosure, the salt is selected from hydrochloride.
The present disclosure also provides a use of the compound above, the isomer thereof or the pharmaceutically acceptable salt thereof in manufacturing a medicament for the treatment of a disease associated with LSD1.

Technical Effect

As a new type of LSD1 inhibitor, the compounds of the present disclosure have significant inhibitory activity against LSD1, and have obvious inhibitory activity against the proliferation of NCI-H1417, HL60 and MV-4-11 cells; have good pharmacokinetic properties simultaneously; and have excellent tumor inhibition effects in combination with the chemotherapy drug cisplatin in the human small cell lung cancer NCI-H1417 xenograft tumor model, and incombination with PD-1 monoclonal antibody in the MC38 mouse colon cancer xenograft model.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(D)" or "(+)" refers to dextrorotation, "(L)" or "(−)" refers to levorotation, and "(DL)" or "(±)" refers to racemic.

Unless otherwise specified, the absolute configuration of a stereogenic center is represented by a wedged solid bond ( ▰ ) and a wedged dashed bond ( ▰ ), and the relative configuration of a stereogenic center is represented by a straight solid bond ( ▰ ) and a straight dashed bond ( ▰ ), a wave line ( ∿ ) is used to represent a wedged dashed bond ( ▰ ) or a wedged dashed bond ( ▰ ), or the wave line ( ∿ ) is used to represent a straight solid bond ( ▰ ) and a straight dashed bond ( ▰ ).

Unless otherwise specified, when double bond structure, such as carbon-carbon double bond, carbon-nitrogen double bond, and nitrogen-nitrogen double bond, exists in the compound, and each of the atoms on the double bond is connected to two different substituents (including the condition where a double bond contains a nitrogen atom, the lone pair of electrons attached on the nitrogen atom is regarded as a substituent connected), if the atom on the double bond in the compound is connected to its substituent by a wave line ( ∿ ), this refers to the (Z) isomer, (E) isomer or a mixture of two isomers of the compound. For example, the following formula (A) means that the compound exists as a single isomer of formula (A-1) or formula (A-2) or as a mixture of two isomers of formula (A-1) and formula (A-2); the following formula (B) means that the compound exists in the form of a single isomer of formula (B-1) or formula (B-2) or in the form of a mixture of two isomers of formula (B-1) and formula (B-2). The following formula (C) means that the compound exists as a single isomer of formula (C-1) or formula (C-2) or as two a mixture of two isomers of formula (C-1) and formula (C-2).

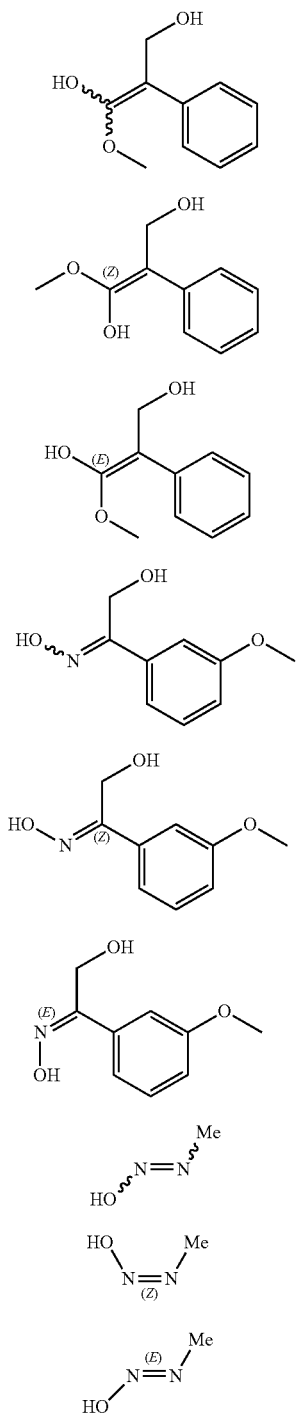

(A)
(A-1)
(A-2)
(B)
(B-1)
(B-2)
(C)
(C-1)
(C-2)

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (9-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^{3}$H), iodine-125 ($^{125}$I) or C-14 ($^{14}$C). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure. The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the bond of a substituent can be cross-connected to more than two or one atoms on a ring, this kind of substituent can be bonded to any atom on the ring, for example, the moiety

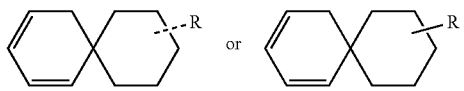

represents for substitution of the substituent R can occurred at any position on the cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

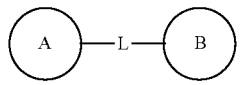

is-M-W—, then-M-W— can link ring A and ring B to form

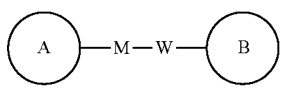

in the direction same as left-to-right reading order, and form

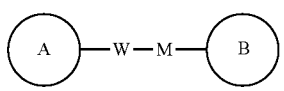

in the direction contrary to left-to-right reading order. A combination of the linking groups, substituents and/or variables thereof is allowed only when such combination can result in a stable compound.

Unless otherwise specified, the number of atoms in a ring is generally defined as the number of ring members. For example, "5-7 membered ring" refers to a "ring" in which 5 to 7 atoms are arranged around.

Unless otherwise specified, the term "3-12 membered ring" refers to a cycloalkyl, heterocycloalkyl, cycloalkenyl, or heterocycloalkenyl having 3 to 12 ring atoms. The ring includes single ring, and also includes double ring or multiple ring system such as spiro ring, fused ring, and bridged ring. Unless otherwise specified, the ring optionally contains 1, 2 or 3 heteroatoms independently selected from O, S and N. The 3-12 membered ring includes 3-10 membered, 3-9 membered, 3-8 membered, 3-7 membered, 3-6 membered, 3-5 membered, 4-10 membered, 4-9 membered, 4-8 membered, 4-7 membered, 4-6 membered, 4-5 membered, 5-10 membered, 5-9 membered, 5-8 membered, 5-7 membered, 5-6 membered, 6-10 membered, 6-9 membered, 6-8 membered and 6-7 membered rings, etc. The term "5-7 membered heterocycloalkyl" includes piperidyl, but excluding phenyl. The term "ring" also includes a ring system containing at least one ring, wherein each "ring" independently meets the above definition.

Unless otherwise specified, the term "$C_{1-6}$ alkyl" refers to a linear or branched saturated hydrocarbon group containing 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl groups and the like. It can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl, etc.

Unless otherwise specified, the term "$C_{1-3}$ alkyl" refers to a linear or branched saturated hydrocarbon group having 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-6}$ alkoxy" refers to an alkyl group containing 1 to 6 carbon atoms that are connected to the rest of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy, etc. Examples $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentoxy (including n-pentoxy, isopentoxy and neopentoxy), hexoxy, etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy) etc.

Unless otherwise specified, "$C_{3-8}$ cycloalkyl" refers a saturated cyclic hydrocarbon group having 3 to 8 carbon atoms, which includes monocyclic and bicyclic systems, where the bicyclic systems include spiro ring, fused ring and bridged ring. $C_{3-8}$ cycloalkyl includes $C_{3-6}$, $C_{3-5}$, $C_{4-8}$, $C_{4-6}$, $C_{4-5}$, $C_{5-8}$ or $C_{5-6}$ cycloakyl, etc; and it may be monovalent, divalent, or multivalent. Examples of $C_{3-8}$ cycloalkyl include, but are not limited to, cyclopropyl, cyclobutyl, cyclopentyl, cyclohexyl, cycloheptyl, norbornyl, [2.2.2] dicyclooctane and the like.

Unless otherwise specified, the term "3-6 membered heterocycloalkyl" by itself or in combination with other terms refers to a saturated cyclic group having 3 to 6 ring atoms, with 1, 2, 3 or 4 ring atoms being heteroatoms independently selected from O, S and N, and the rest are carbon atoms, wherein the N atom is optionally quaternized, and the N and S heteroatoms may optionally be oxidized (i.e. NO and $S(O)_p$, p is 1 or 2). It includes monocyclic and bicyclic systems, wherein bicyclic system includes spiro ring, fused ring, and bridged ring. In addition, with regard to the "3-6 membered heterocycloalkyl", a heteroatom may occupy the linking position of the heterocycloalkyl with the rest of the molecule. The 3-6 membered heterocycloalkyl includes 4-6 membered, 5-6 membered, 4 membered, 5 membered, and 6 membered heterocycloalkyl groups. Examples of 3-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidyl (including 1-piperidyl, 2-piperidyl and 3-piperidyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl.

Unless otherwise specified, the terms "$C_{6-10}$ aromatic ring" and "$C_{6-10}$ aryl" can be used interchangeably in the present disclosure, and the term "$C_{6-10}$ aromatic ring" or "$C_{6-10}$ aryl" refers a cyclic hydrocarbon group containing 6 to 10 carbon atoms, having a conjugated π-electron system, it can be a single ring, a fused bicyclic ring or a fused tricyclic ring system, wherein each ring is aromatic. It can be monovalent, divalent or multivalent, $C_{6-10}$ aryl groups include $C_{6-9}$, $C_9$, $C_{10}$ and $C_6$ aryl groups, etc. Examples of $C_{6-10}$ aryl groups include, but are not limited to, phenyl, naphthyl (including 1-naphthyl and 2-naphthyl).

Unless otherwise specified, the terms "5-6 membered heteroaromatic ring" and "5-6 membered heteroaryl" can be used interchangeably in the present disclosure. The term "5-6 membered heteroaryl" refers to a monocyclic group having 5 or 6 ring atoms, having a conjugated π-electron system, with 1, 2, 3 or 4 ring atoms being heteroatoms independently selected from O, S and N, and the rest are carbon atoms, wherein the N atom is optionally quaternized, and the N and S heteroatoms may optionally be oxidized (i.e. NO and $S(O)_p$, p is 1 or 2). The 5-6 membered heteroaryl can be connected to the rest of the molecule through a heteroatom or a carbon atom. The 5-6 membered heteroaryl includes 5 membered and 6 membered heteroaryl groups. Examples of the 5-6 membered heteroaryl group include, but are not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl or pyrimidinyl (including 2-pyrimidinyl and 4-pyrimidinyl, etc.).

Unless otherwise specified, $C_{n-n+m}$ or $C_{n-C+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n membered to n+m membered means that the number of atoms on the ring is from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring, etc.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl, and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvents used in the present disclosure are commercially available. The present disclosure uses the following abbreviations: aq represents for water; HATU represents for O-(7-azabenzotriazol-1-yl)-N, N, N', N'-tetramethyluronium hexafluorophosphate; EDC represents for N-(3-dimethylaminopropyl)-N'-ethylcarbodiimide hydrochloride; m-CPBA represents for 3-chloroperoxybenzoic acid; eq represents for equivalent; CDI represents for carbonyl diimidazole; DCM represents for dichloromethane; PE represents for petroleum ether; DIAD represents for diisopropyl azodicarboxylate; DMF represents for N, N-dimethylformamide; DMSO represents for dimethyl sulfoxide; EtOAc represents for ethyl acetate; EtOH represents for ethanol; MeOH represents for methanol; CBz represents for benzyloxycarbonyl, which is an amine protecting group; BOC represents for tert-butoxycarbonyl, which is an amine protecting group;

HOAc represents for acetic acid; NaCNBH₃ represents for sodium cyanoborohydride; r.t. represents for room temperature; O/N represents for overnight; THF represents for tetrahydrofuran; Boc₂O represents for di-tert-butyl dicarbonate; TFA represents for trifluoroacetic acid; the pH value of the hydrochloride of the compound of the present disclosure can be adjusted to neutral by adding saturated sodium bicarbonate solution, and then purified by high performance liquid chromatography (neutral, ammonium bicarbonate system) to obtain the free base of the compound.

The compounds of the present disclosure are named according to the conventional naming principles in the art or by ChemDraw® software, and the commercially available compounds use the supplier catalog names.

DETAILED DESCRIPTION OF THE EMBODIMENTS

The following examples further illustrate the present disclosure, but the present disclosure is not limited thereto.

The present disclosure has been described in detail herein, and its specific embodiments have also been disclosed, for one skilled in the art, it is obvious to make various modifications and improvements to the embodiments of the present disclosure without departing from the spirit and scope of the present disclosure.

Embodiment 1

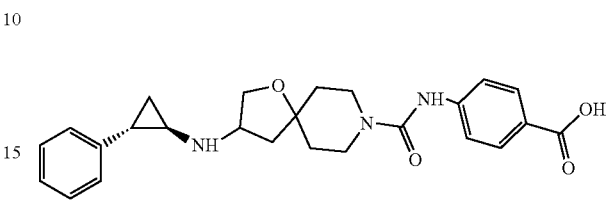

Synthetic Route:

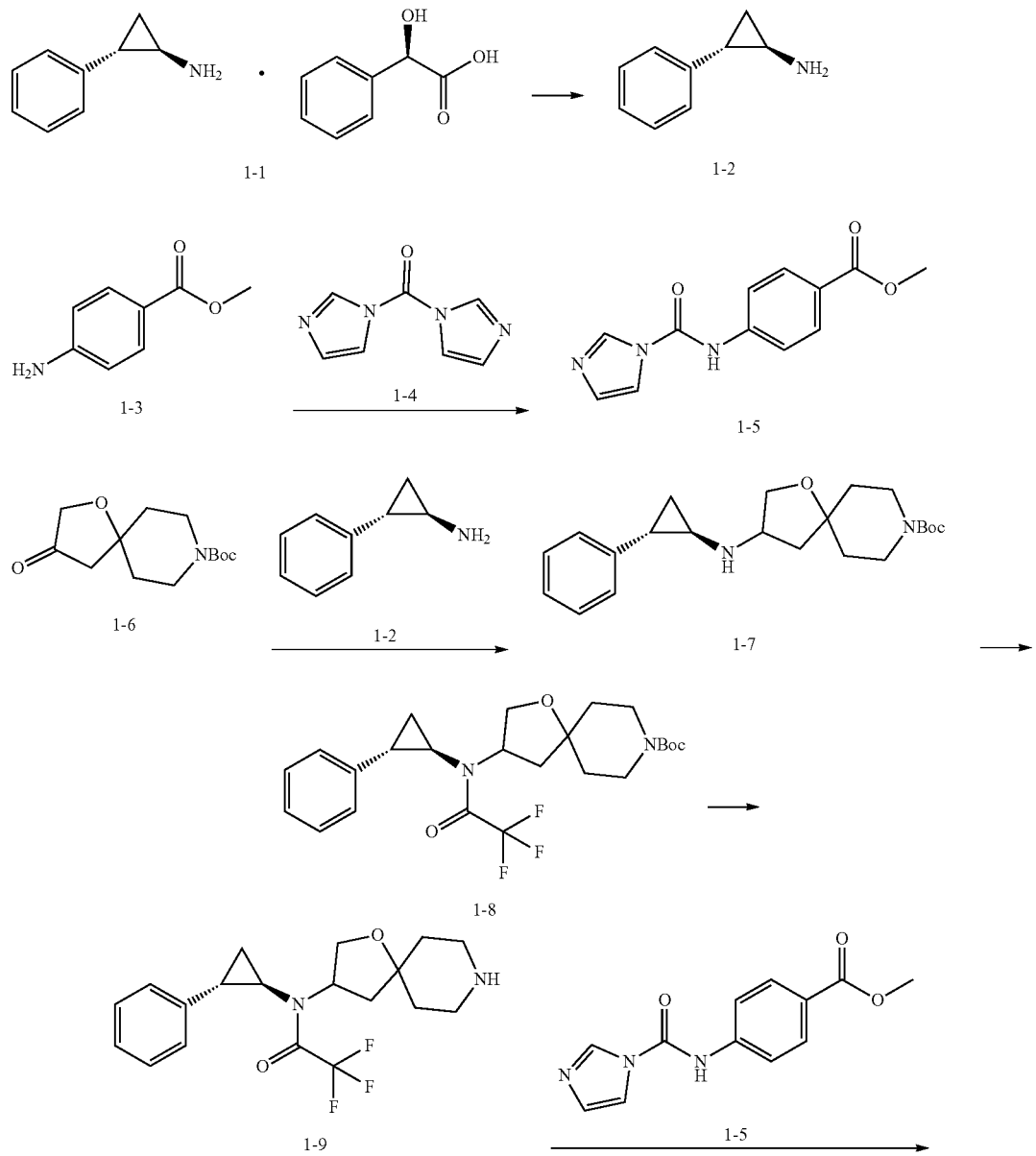

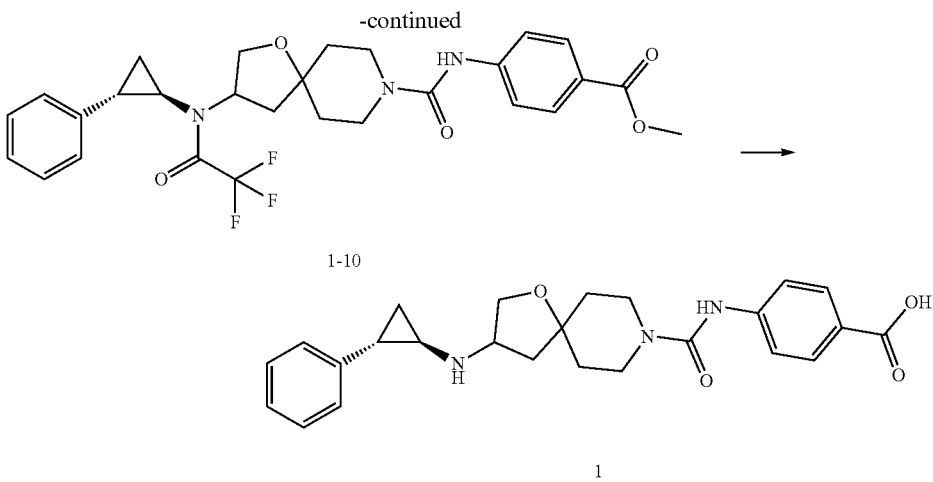

1-10

1

Step 1

Sodium hydroxide (279 g, 6.99 mol) was dissolved in water (3 L), then the reaction mixture was cooled to 10° C. with an ice-water bath, compound 1-1 (997 g, 3.49 mol) was added to the reaction mixture in batches, and the reaction mixture was stirred at 10° C. for 2 hours. Ethyl acetate (2 L×1) was added to the reaction mixture for extraction, the mixture was extracted with ethyl acetate (1.6 L×1). The organic phases were combined, washed with water (1.5 L×1), and then washed with saturated brine (1.5 L×1). The organic phase was dried over anhydrous sodium sulfate, filtered, and concentrated under reduced pressure to remove the solvent to obtain the compound 1-2. $^1H$ NMR (400 MHz, CDCl$_3$) δ 7.18-7.14 (m, 2H), 7.08-7.04 (m, 1H), 6.95-6.92 (m, 2H), 2.48-2.44 (m, 1H), 1.80-1.76 (m, 1H), 0.98-0.87 (m, 2H).

Step 2

Compound 1-3 (1.00 g, 6.62 mmol) and compound 1-4 (1.50 g, 9.26 mmol) were dissolved in 1, 2-dichloroethane (10 mL). The reaction mixture was stirred at 50° C. for 12 hours. The reaction mixture was cooled to 0° C. and stirred for 1 hour, filtered, and the filter cake was washed with dichloromethane (10 mL×2) to obtain compound 1-5. $^1H$ NMR (400 MHz, DMSO-d$_6$) δ 8.43 (s, 1H), 8.02-7.99 (m, 2H), 7.82-7.80 (m, 2H), 7.11 (s, 1H), 7.04 (s, 1H), 3.85 (m, 3H).

Step 3

Compound 1-6 (1.00 g, 3.92 mmol) and compound 1-2 (522 mg, 3.92 mmol) were dissolved in anhydrous dichloromethane (20 mL), and glacial acetic acid (706 mg, 11.8 mmol) was added to the reaction mixture. The reaction mixture was stirred at 20° C. for 1 hour, sodium triacetoxyborohydride (2.49 g, 11.8 mmol) was added thereto, and the reaction mixture was stirred at 20° C. for 10 hours. The reaction mixture was diluted with dichloromethane (80 mL) and washed with saturated aqueous solution of sodium bicarbonate (100 mL×3), water (100 mL×2), and saturated brine (100 mL×1), and then dried over anhydrous sodium sulfate, filtered, and the resulting mother liquor was concentrated to obtain compound 1-7. $^1H$ NMR (400 MHz, CDCl$_3$) δ 7.18-7.16 (m, 2H), 7.11-7.17 (m, 1H), 6.96-6.94 (m, 2H), 3.92-3.89 (m, 1H), 3.61-3.55 (m, 1H), 3.52-3.48 (m, 3H), 3.27-3.23 (m, 2H), 2.24-2.21 (m, 1H), 1.99-1.94 (m, 1H), 1.85-1.79 (m, 1H), 1.55-1.47 (m, 6H), 1.38 (s, 9H), 1.01-0.90 (m, 2H). MS-ESI calculated value [M+H]$^+$ 373, measured value 373.

Step 4

Compound 1-7 (1.10 g, 2.95 mmol) was dissolved in anhydrous dichloromethane (20 mL), triethylamine (448 mg, 4.43 mmol) and trifluoroacetic anhydride (930 mg, 4.43 mmol) were added thereto. The reaction mixture was stirred at 15° C. for 12 hours. Dichloromethane (50 mL) was added to the reaction mixture, the organic phase was washed with hydrochloric acid (1M, 50 mL×1) and saturated brine (50 mL×1), dried over anhydrous sodium sulfate, filtered, and the mother liquor was concentrated, the crude product was purified by column chromatography (5/1 petroleum ether/ ethyl acetate, R$_f$=0.3) to obtain compound 1-8. MS-ESI calculated values [M−56+H]$^+$413, [M−Boc+H]$^+$369, measured values 413, 369.

Step 5

Compound 1-8 (600 mg, 1.28 mmol) was dissolved in anhydrous dichloromethane (6 mL), and trifluoroacetic acid (4.62 g, 40.5 mmol) was added thereto at 20° C. The reaction mixture was stirred at 20° C. for 2 hours, concentrated under reduced pressure to remove the solvent, and the residue was dissolved in dichloromethane (6 mL), and then triethylamine (250 µL) was added thereto, and stirred at room temperature for half an hour. The solvent was removed by concentration under reduced pressure to obtain compound 1-9. MS-ESI calculated value [M+H]$^+$ 369, measured value 369.

Step 6

Compound 1-9 (100 mg, 0.271 mmol) and compound 1-5 (69.9 mg, 0.285 mmol) were dissolved in 1, 2-dichloroethane (10 mL). The reaction mixture was stirred at 50° C. for 2 hours, concentrated under reduced pressure to remove the solvent, the residue was dissolved in dichloromethane (50 mL), and the organic phase was washed with water (50 mL×1) and saturated brine (50 mL×1) in sequence, then dried over anhydrous sodium sulfate, filtered, and then the mother liquor was concentrated, the crude product was purified by thin layer chromatography (1/1 petroleum ether/ethyl acetate, $R_f$=0.34) to obtain compound 1-10. MS-ESI calculated value [M+H]⁺ 546, measured value 546.

Step 7

Compound 1-10 (100 mg, 0.183 mmol) was dissolved in water (3 mL) and tetrahydrofuran (3 mL), and sodium hydroxide (22.0 mg, 0.549 mmol) was added thereto. The reaction mixture was stirred at 50° C. for 12 hours, concentrated under reduced pressure to remove tetrahydrofuran, and the residue was dissolved in water (3 mL), the pH value was adjusted to 4 with hydrochloric acid (1 mol/L), and the mixture was separated by high performance liquid chromatography (acidic, hydrochloric acid system) to obtain the hydrochloride of compound 1. ¹H NMR (400 MHz, CD₃OD) δ 7.92 (d, J=8.8, 2H), 7.47 (d, J=8.8, 2H), 7.34-7.30 (m, 2H), 7.26-7.22 (m, 1H), 7.20-7.18 (m, 2H), 4.16-4.06 (m, 3H), 3.86-3.79 (m, 2H), 3.42-3.38 (m, 2H), 3.02-3.01 (m, 1H), 2.53-2.38 (m, 2H), 1.93-1.79 (m, 4H), 1.56-1.53 (m, 2H), 1.46-1.43 (m, 1H). MS-ESI calculated value [M+H]⁺ 436, measured value 436.

Embodiment 2

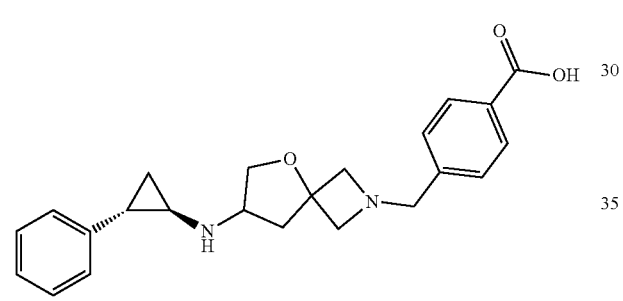

Synthetic Route:

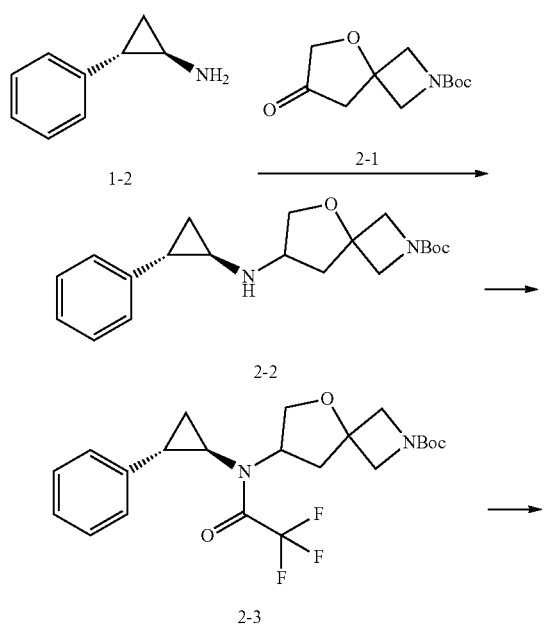

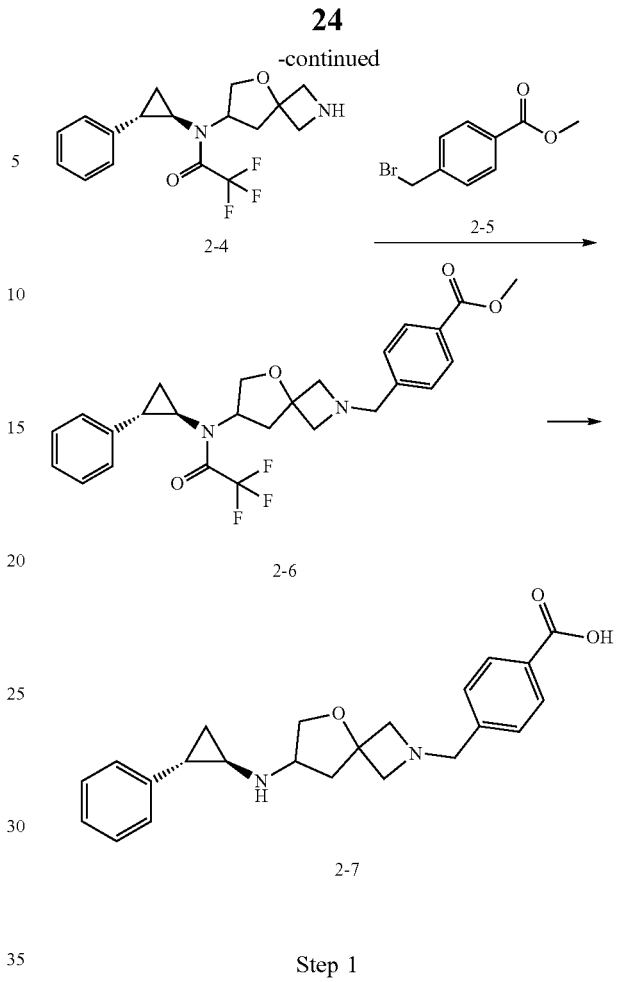

Step 1

Compound 2-1 (194 mg, 0.856 mmol) and compound 1-2 (114 mg, 0.856 mmol) were dissolved in anhydrous dichloromethane (1 mL), glacial acetic acid (154 mg, 2.57 mmol) was added to the reaction mixture. The reaction mixture was stirred at 26° C. for 2 hours, sodium triacetoxyborohydride (544 mg, 2.57 mmol) was added thereto, and the reaction mixture was stirred at 26° C. for 10 hours. Saturated sodium bicarbonate (30 mL) solution was added to the reaction mixture, extracted with dichloromethane (30 mL×3), the organic phases were combined and washed with saturated brine (30 mL×1), then dried over anhydrous sodium sulfate, filtered, and the mother liquor was concentrated, the crude product was purified by thin layer chromatography (2:1 petroleum ether/ethyl acetate, $R_f$=0.26) to obtain compound 2-2. MS-ESI calculated value [M+H]⁺ 345, measured value 345.

Step 2

Compound 2-2 (154 mg, 0.447 mmol) was dissolved in anhydrous dichloromethane (5 mL), triethylamine (67.9 mg, 0.670 mmol) and trifluoroacetic anhydride (141 mg, 0.670 mmol) were added thereto. The reaction mixture was stirred at 25° C. for 12 hours. Dichloromethane (50 mL) was added to the reaction mixture, the organic phase was washed with hydrochloric acid (1M, 30 mL) and saturated brine (50 mL), dried over anhydrous sodium sulfate, filtered, and the mother liquor was concentrated, the crude product was purified by thin layer chromatography (3/1 petroleum ether/ethyl acetate, $R_f$=0.84) to obtain compound 2-3. ¹H NMR (400 MHz, CDCl$_3$) δ 7.34-7.31 (m, 2H), 7.28-7.23 (m, 1H), 7.09-7.03 (m, 2H), 4.55-4.47 (m, 1H), 4.16-3.84 (m, 6H), 3.12-2.91 (m, 1H), 2.49-2.05 (m, 3H), 1.53-1.43 (m, 11H). MS-ESI calculated values [M−56+H]$^+$ 385, [M−Boc+H]$^+$ 341, measured values 385, 341.

Step 3

Compound 2-3 (160 mg, 0.408 mmol) was dissolved in anhydrous dichloromethane (2 mL), and trifluoroacetic acid (1 mL, 13.5 μmol) was added dropwise at 0° C. The reaction mixture was stirred at 20° C. for 1 hour, and concentrated under reduced pressure to remove the solvent to obtain compound 2-4. MS-ESI calculated value [M+H]$^+$ 341, measured value 341.

Step 4

Compound 2-4 (200 mg, 0.587 mmol), compound 2-5 (137 mg, 0.599 mmol) and triethylamine (178 mg, 1.76 mmol) were dissolved in acetonitrile (5 mL). The reaction mixture was stirred at 50° C. for 2 hours, concentrated under reduced pressure to remove the solvent, the residue was dissolved in dichloromethane (50 mL), and the organic phase was washed with water (50 mL×1) and saturated brine (50 mL×1) in sequence, the mixture was dried over anhydrous sodium sulfate, filtered, the mother liquor was concentrated, and the crude product was purified by thin layer chromatography (1/1 petroleum ether/ethyl acetate, R$_f$=0.34) to obtain compound 2-6. $^1$H NMR (400 MHz, CDCl$_3$) δ 8.01-7.98 (m, 2H), 7.38-7.24 (m, 5H), 7.10-7.04 (m, 2H), 4.62-4.51 (m, 1H), 4.04-3.98 (m, 1H), 3.92-3.84 (m, 4H), 3.73-3.70 (m, 2H), 3.54-3.18 (m, 4H), 3.08-2.89 (m, 1H), 2.60-2.34 (m, 3H), 1.59-1.42 (m, 2H). MS-ESI calculated values [M+H]$^+$ 489, measured values 489.

Step 5

Compound 2-6 (140 mg, 0.287 mmol) was dissolved in water (1 mL) and tetrahydrofuran (4 mL), and sodium hydroxide (34.4 mg, 0.859 mmol) was added thereto. The reaction mixture was stirred at 50° C. for 2 hours, concentrated under reduced pressure to remove tetrahydrofuran, and the residue was dissolved in water (3 mL), the pH value was adjusted to 4 with hydrochloric acid (1 mol/L), and the mixture was purified by high performance liquid chromatography (acid, hydrochloric acid system) to obtain the hydrochloride of compound 2. $^1$H NMR (400 MHz, CD$_3$OD) δ 8.12-8.10 (m, 2H), 7.61-7.59 (m, 2H), 7.33-7.29 (m, 2H), 7.25-7.17 (m, 3H), 4.65-4.45 (m, 3H), 4.36-4.08 (m, 6H), 3.03-2.99 (m, 1H), 2.90-2.80 (m, 1H), 2.60-2.53 (m, 2H), 1.61-1.55 (m, 1H), 1.45-1.40 (m, 1H). MS-ESI calculated values [M+H]$^+$ 379, measured values 379.

Embodiment 3

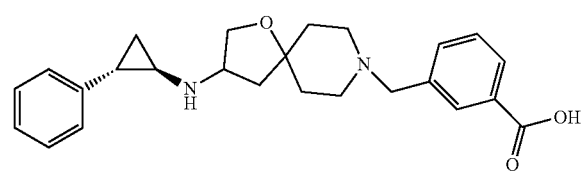 [SMILES: O=C(O)c1cccc(CN2CCC3(CC2)CC(N[C@@H]2C[C@H]2c2ccccc2)CO3)c1]

Synthetic Route:

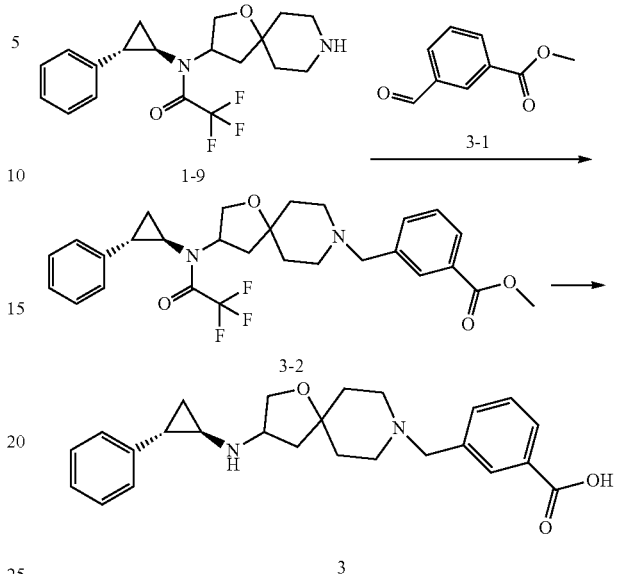

Step 1

Compound 3-1 (89.1 mg, 0.543 mmol) and compound 1-9 (100 mg, 0.271 mmol) were dissolved in anhydrous dichloromethane (2 mL), and glacial acetic acid (48.9 mg, 0.814 mmol) was added thereto. The reaction mixture was stirred at 0-30° C. for 12 hours, sodium triacetoxyborohydride (173 mg, 0.814 mmol) was added thereto, and the reaction mixture was stirred at 30° C. for 1 hour. Saturated sodium bicarbonate solution (20 mL) was added to the reaction mixture, the mixture was extracted with dichloromethane (10 mL×3), and the combined organic phase was washed with water (10 mL×1) and saturated brine (10 mL×1) in sequence, the mixture was then dried over anhydrous sodium sulfate, filtered, the filtrate was concentrated, and the crude product was purified by thin layer chromatography (3:1 petroleum ether/ethyl acetate, R$_f$=0.86) to obtain compound 3-2. MS-ESI calculated value [M+H]$^+$ 517, measured value 517.

Step 2

Compound 3-2 (30.0 mg, 0.580 mmol) was dissolved in tetrahydrofuran (1 mL), ethanol (1 mL) and water (1 mL), and sodium hydroxide (6.97 mg, 0.174 mmol) was added to the reaction mixture. The reaction mixture was stirred for reaction at 60° C. for 3 hours, and concentrated under reduced pressure to remove the solvent. The residue was diluted with water, and the pH value was adjusted to about 4 with aqueous solution of hydrochloric acid (1 mol/L), and the mixture was purified by high performance liquid chromatography (hydrochloric acid system) to obtain the hydrochloride of compound 3. $^1$H NMR (400 MHz, CD$_3$OD) δ 8.23 (s, 1H), 8.18-8.16 (m, 1H), 7.85-7.83 (m, 1H), 7.64-7.62 (m, 1H), 7.34-7.31 (m, 2H), 7.25-7.19 (m, 3H), 4.54 (s, 2H), 4.44-4.14 (m, 3H), 3.42-3.37 (m, 2H), 3.31-3.28 (m, 2H), 3.03-3.02 (m, 1H), 2.62-2.58 (m, 1H), 2.45-2.40 (m, 1H), 2.16-2.05 (m, 4H), 1.95-1.88 (m, 1H), 1.64-1.59 (m, 1H), 1.46-1.42 (m, 1H). MS-ESI calculated values [M+H]$^+$ 407, measured values 407.

Embodiment 4

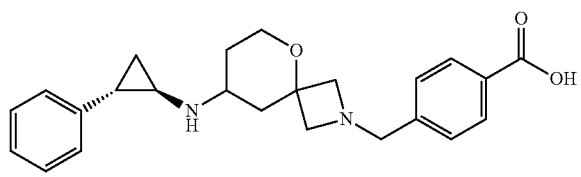 [SMILES: O=C(O)c1ccc(CN2CC3(CC(N[C@@H]4C[C@H]4c4ccccc4)CCO3)C2)cc1]

Synthetic Route:

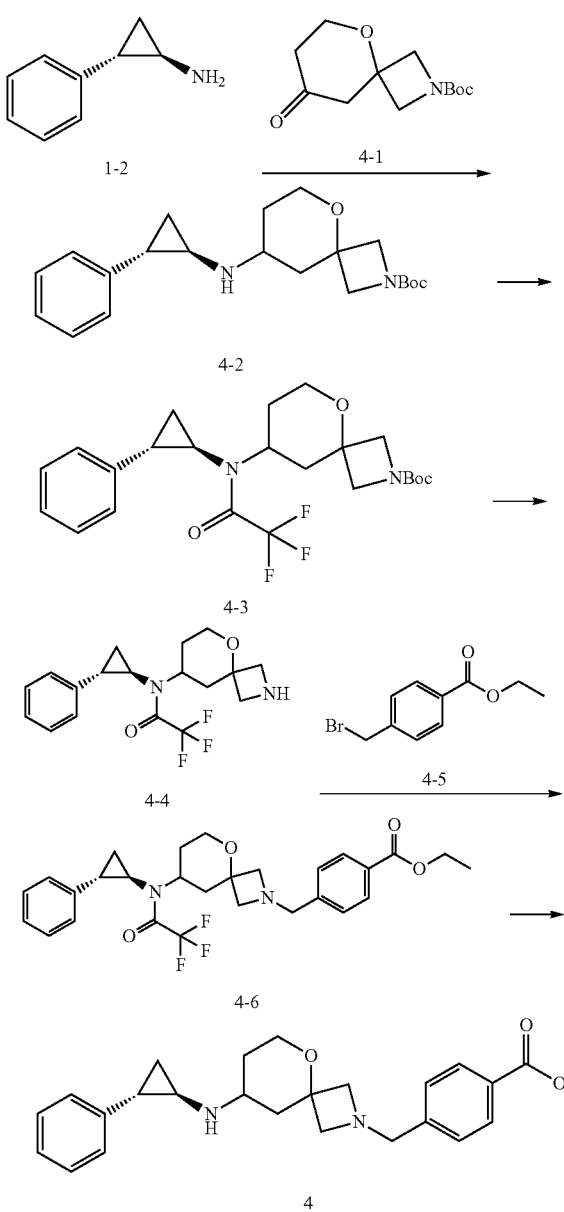

Step 1

Compound 4-2 was obtained by referring to Step 1 of Embodiment 2. MS-ESI calculated value [M+H]$^+$ 359, measured value 359.

Step 2

Compound 4-3 was obtained by referring to Step 2 of Embodiment 2. MS-ESI calculated values [M+Na]$^+$477, measured values 477.

Step 3

Compound 4-4 was obtained by referring to Step 3 of Embodiment 2. MS-ESI calculated values [M+H]$^+$ 355, measured values 355.

Step 4

Compound 4-6 was obtained by referring to Step 4 of Embodiment 2. $^1$H NMR (400 MHz, CDCl$_3$) δ 7.92-7.90 (m, 2H), 7.28-7.26 (m, 4H), 7.25-7.22 (m, 2H), 7.16-7.01 (m, 1H), 4.32-4.27 (m, 2H), 4.14-4.02 (m, 1H), 3.84-3.74 (m, 1H), 3.66-3.63 (m, 2H), 3.40-3.37 (m, 2H), 3.15-3.08 (m, 1H), 3.03-2.95 (m, 3H), 2.15-2.10 (m, 4H), 1.65-1.55 (m, 1H), 1.39-1.29 (m, 5H). MS-ESI calculated values [M+H]$^+$ 517, measured values 517.

Step 5

The hydrochloride of Compound 4 was obtained by referring to Step 5 of Embodiment 2. $^1$H NMR (400 MHz, CD$_3$OD) δ 8.11 (d, J=8.0, 2H), 7.63 (dd, J=8.0, 2.8, 2H), 7.31-7.29 (m, 2H), 7.23-7.19 (m, 3H), 4.55 (s, 2H), 4.36-4.34 (m, 3H), 4.23-4.02 (m, 2H), 3.64-3.62 (m, 2H), 3.02-2.99 (m, 1H), 2.79-2.71 (m, 1H), 2.55-2.49 (m, 1H), 2.12-2.07 (m, 1H), 1.85-1.73 (m, 2H), 1.60-1.56 (m, 1H), 1.46-1.44 (m, 1H). MS-ESI calculated values [M+H]$^+$ 393, measured values 393.

Embodiment 5

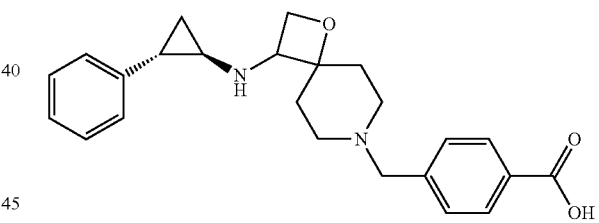

Synthetic Route:

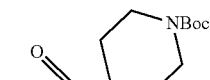

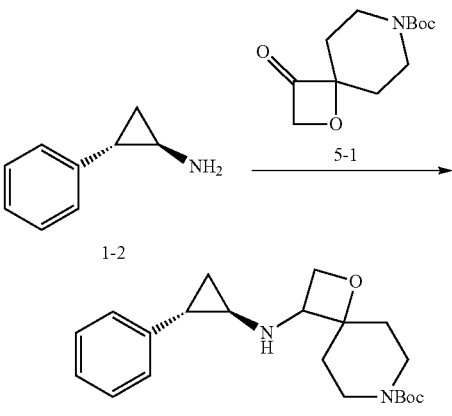

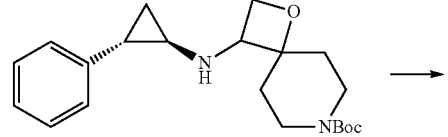

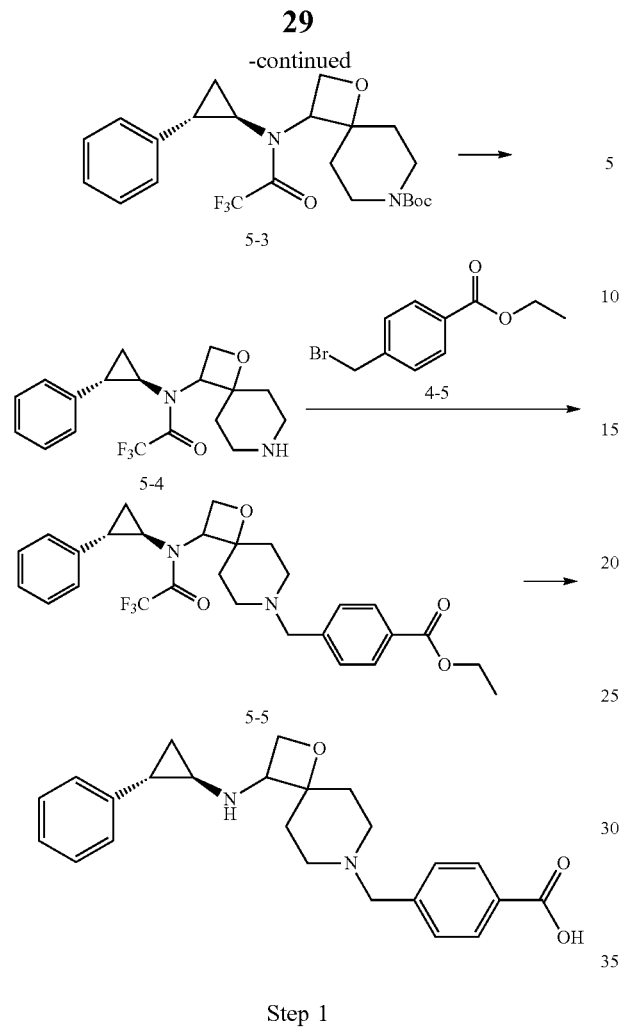

CD₃OD) δ 8.13 (d, J=8.0, 2H), 7.68 (d, J=8.0, 2H), 7.31-7.28 (m, 2H), 7.24-7.15 (m, 3H), 4.70-4.64 (m, 1H), 4.45-4.37 (m, 3H), 3.53-3.34 (m, 2H), 3.27-3.21 (m, 2H), 2.91-2.88 (m, 1H), 2.60-2.20 (m, 6H), 1.63-1.58 (m, 1H), 1.38-1.32 (m, 1H). MS-ESI calculated values [M+H]⁺ 393, measured values 393.

Embodiment 6

Synthetic Route:

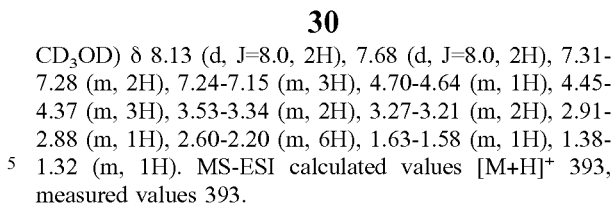

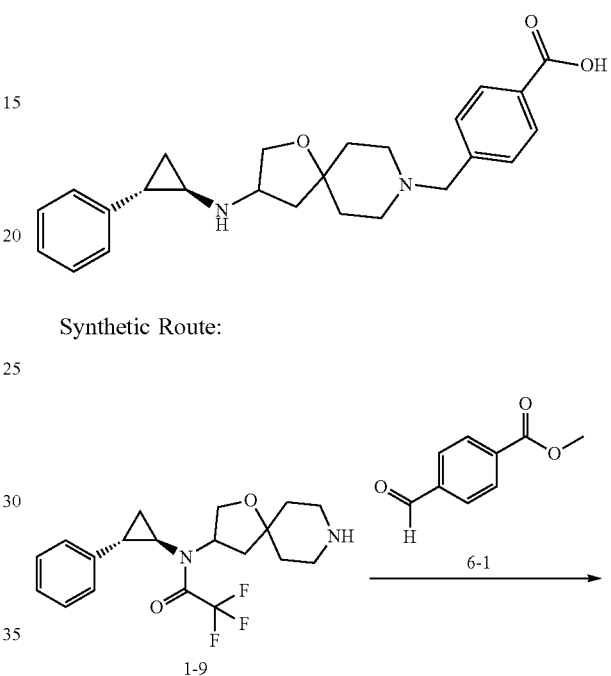

Step 1

Compound 5-2 was obtained by referring to Step 1 of Embodiment 2. MS-ESI calculated values [M+H]⁺ 359, measured values 359.

Step 2

Compound 5-3 was obtained by referring to Step 2 of Embodiment 2. MS-ESI calculated values [M+H]⁺ 455, measured values 455.

Step 3

Compound 5-4 was obtained by referring to Step 3 of Embodiment 2. MS-ESI calculated values [M+H]⁺ 355, measured values 355.

Step 4

Compound 5-5 was obtained by referring to Step 4 of Embodiment 2. ¹H NMR (400 MHz, CDCl₃) δ 7.96-7.94 (m, 2H), 7.36-7.29 (m, 4H), 7.22-7.20 (m, 1H), 7.02-6.95 (m, 2H), 4.63-4.52 (m, 2H), 4.32-4.26 (m, 2H), 3.52 (s, 2H), 3.11-3.02 (m, 1H), 2.65-2.63 (m, 2H), 2.29-2.14 (m, 3H), 1.93-1.79 (m, 2H), 1.54-1.49 (m, 4H), 1.33-1.26 (m, 4H). MS-ESI calculated values [M+H]⁺ 517, measured values 517.

Step 5

The hydrochloride of Compound 5 was obtained by referring to Step 5 of Embodiment 2. ¹H NMR (400 MHz, Step 1

Compound 1-9 (345 mg, 0.936 mmol) and compound 6-1 (154 mg, 0.937 mmol) were dissolved in anhydrous dichloromethane (10 mL), and glacial acetic acid (5.62 mg, 93.6 μmol) was added to the reaction mixture. The reaction mixture was stirred at 20° C. for 10 hours, sodium triacetoxyborohydride (397 mg, 1.87 mmol) was added thereto, and the reaction mixture was stirred at 20° C. for 2 hours. After the reaction mixture was diluted with dichloromethane (50 mL), it was washed with saturated aqueous solution of sodium bicarbonate (50 mL×3), water (50 mL×2) and saturated brine (50 mL×1), and dried over anhydrous sodium sulfate, then filtered, the resulting mother liquor was concentrated, and the crude product was purified by thin layer chromatography (1:1 petroleum ether/ethyl acetate, $R_f$=0.24) to obtain compound 6-2. MS-ESI calculated value [M+H]+ 517, measured value 517.

Step 2

Compound 6-2 (280 mg, 0.542 mmol) was dissolved in tetrahydrofuran (3 mL), water (3 mL) and ethanol (3 mL), and sodium hydroxide (65.1 mg, 1.63 mmol) was added thereto. The reaction mixture was stirred at 60° C. for 3 hours, concentrated under reduced pressure to remove tetrahydrofuran and ethanol, the residue was dissolved in water (10 mL), the pH value was adjusted to 4 with hydrochloric acid (1 M), and the mixture was concentrated under reduced pressure, the residue was purified by high performance liquid chromatography (acidic, hydrochloric acid system) to obtain the hydrochloride of compound 6. $^1$H NMR (400 MHz, CD$_3$OD) δ 8.13 (d, J=8.0 Hz, 2H), 7.72 (d, J=8.0 Hz, 2H), 7.34-7.30 (m, 2H), 7.26-7.19 (m, 3H), 4.43 (s, 2H), 4.22-4.19 (m, 1H), 4.7-4.11 (m, 2H), 3.53-3.37 (m, 2H), 3.32-3.24 (m, 2H), 3.03-3.00 (m, 1H), 2.64-2.60 (m, 1H), 2.45-2.40 (m, 1H), 2.24-2.05 (m, 4H), 2.00-1.93 (m, 1H), 1.64-1.61 (m, 1H), 1.45-1.40 (m, 1H). MS-ESI calculated value [M+H]$^+$ 407, measured value 407. The hydrochloride of compound 6 was dissolved in water (2 mL) and acetonitrile (2 mL), and the pH value was adjusted to neutral by adding saturated sodium bicarbonate solution. The mixture was purified by high performance liquid chromatography (neutral, ammonium bicarbonate system) to obtain compound 6.

Embodiment 7

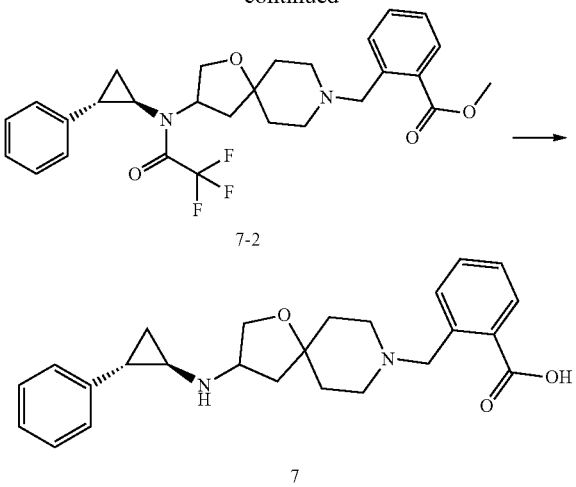

Step 1

Compound 7-2 was obtained by referring to Step 1 of Embodiment 6. MS-ESI calculated values [M+H]$^+$ 517, measured values 517.

Step 2

The hydrochloride of Compound 7 was obtained by referring to Step 2 of Embodiment 6. $^1$H NMR (400 MHz, CD$_3$OD) δ 8.25-8.23 (m, 1H), 7.74-7.65 (m, 3H), 7.34-7.31 (m, 2H), 7.26-7.21 (m, 3H), 4.61 (s, 2H), 4.23-4.21 (m, 3H), 3.52-3.37 (m, 4H), 3.03-3.00 (m, 1H), 2.67-2.63 (m, 1H), 2.44-2.40 (m, 1H), 2.16-2.09 (m, 4H), 1.96-1.87 (m, 1H), 1.69-1.66 (m, 1H), 1.45-1.39 (m, 1H). MS-ESI calculated value [M+H]$^+$ 407, measured value 407.

Embodiment 8

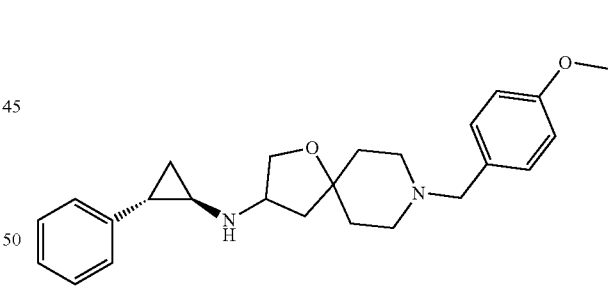

Synthetic Route:

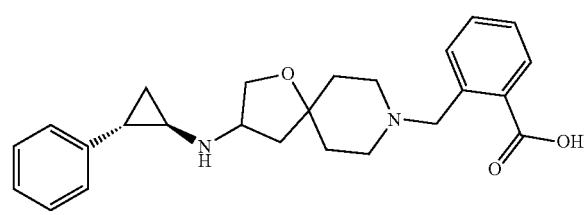 [SMILES: O=C(O)c1ccccc1CN1CCC2(CC1)CC(N[C@@H]1C[C@H]1c1ccccc1)CO2]

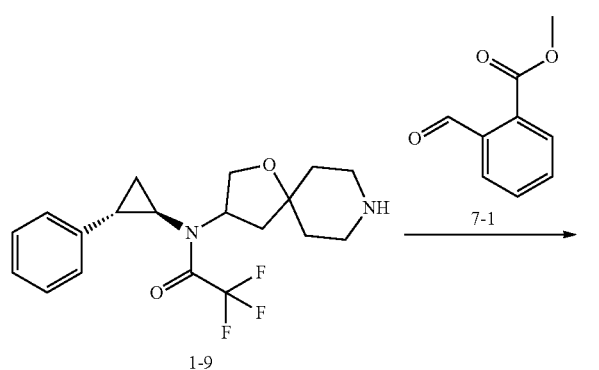

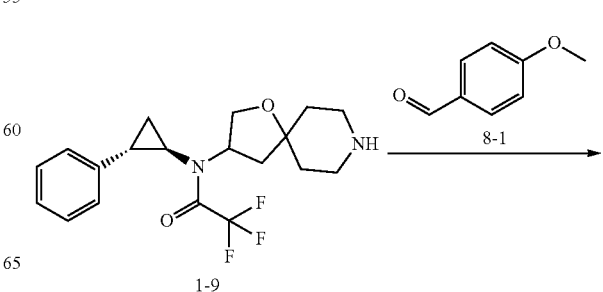

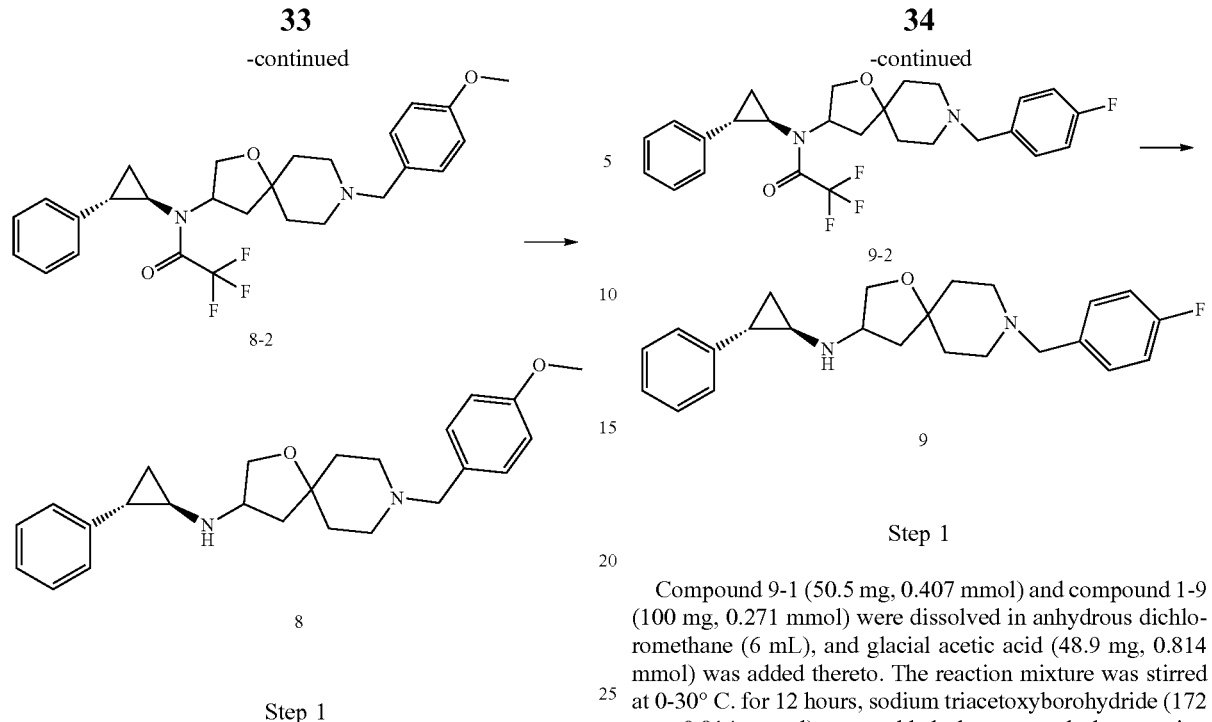

8-2

8

Step 1

Compound 8-2 was obtained by referring to Step 1 of Embodiment 6. MS-ESI calculated values [M+H]+ 489, measured values 489.

Step 2

The hydrochloride of Compound 8 was obtained by referring to Step 2 of Embodiment 6. ¹H NMR (400 MHz, CD₃OD) δ 7.50 (d, J=8.8 Hz, 2H), 7.34-7.31 (m, 2H), 7.26-7.20 (m, 3H), 7.03 (d, J=8.8 Hz, 2H), 4.27 (s, 2H), 4.21-4.19 (m, 1H), 4.16-4.15 (m, 2H), 3.84 (s, 3H), 3.49-3.38 (m, 2H), 3.25-3.16 (m, 2H), 3.03-3.02 (m, 1H), 2.65-2.61 (m, 1H), 2.44-2.39 (m, 1H), 2.17-2.06 (m, 4H), 1.98-1.89 (m, 1H), 1.65-1.62 (m, 1H), 1.45-1.39 (m, 1H). MS-ESI calculated value [M+H]+ 393, measured value 393.

Embodiment 9

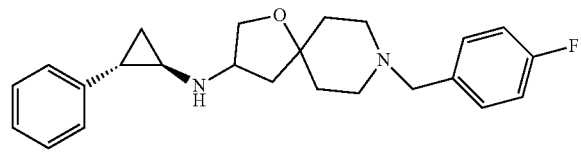 [SMILES: Fc1ccc(CN2CCC3(CC2)CC(N[C@@H]2C[C@H]2c2ccccc2)CO3)cc1]

Synthetic Route:

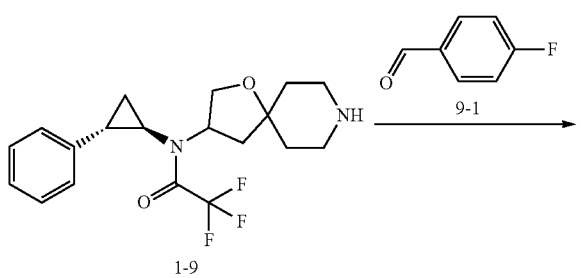

Step 1

Compound 9-1 (50.5 mg, 0.407 mmol) and compound 1-9 (100 mg, 0.271 mmol) were dissolved in anhydrous dichloromethane (6 mL), and glacial acetic acid (48.9 mg, 0.814 mmol) was added thereto. The reaction mixture was stirred at 0-30° C. for 12 hours, sodium triacetoxyborohydride (172 mg, 0.814 mmol) was added thereto, and the reaction mixture was stirred at 30° C. for 1 hour. Then saturated sodium bicarbonate (20 mL) was added to the reaction mixture, the mixture was extracted with dichloromethane (10 mL×3), the organic phases were combined, and then washed with water (10 mL×1) and saturated brine (10 mL×1), dried over anhydrous sodium sulfate, filtered, then the mother liquor was concentrated, and the crude product was purified by thin layer chromatography (3:1 petroleum ether/ethyl acetate, $R_f$=0.86) to obtain compound 9-2. MS-ESI calculated value [M+H]+ 477, measured value 477.

Step 2

Compound 9-2 (40.0 mg, 83.9 μmol) was dissolved in tetrahydrofuran (1 mL), ethanol (1 mL) and water (1 mL), and sodium hydroxide (10.0 mg, 0.252 mmol) was added to the reaction mixture. The reaction mixture was stirred at 60° C. for 2.5 hours, concentrated under reduced pressure to remove the solvent, the residue was diluted with water, and the pH value was adjusted to about 4 with aqueous hydrochloric acid (1 mol/L). The hydrochloride of compound 9 was prepared by high performance liquid chromatography (acidic, hydrochloric acid system). ¹H NMR (400 MHz, CD₃OD) δ 7.66-7.63 (dd, J=7.7, 5.5, 2H), 7.33-7.31 (m, 2H), 7.26-7.20 (m, 5H), 4.35 (s, 2H), 4.22-4.15 (m, 3H), 3.43-3.36 (m, 2H), 3.26-3.20 (m, 2H), 3.03 (s, 1H), 2.63-2.62 (m, 1H), 2.45-2.40 (m, 1H), 2.19-2.08 (m, 4H), 1.98-1.95 (m, 1H), 1.65-1.62 (m, 1H), 1.43-1.42 (m, 1H). MS-ESI calculated value [M+H]+ 381, measured value 381.

Embodiment 10

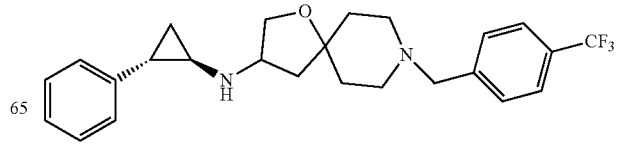

Embodiment 11

Synthetic Route:

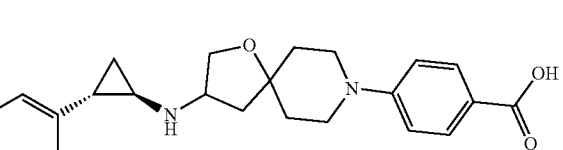

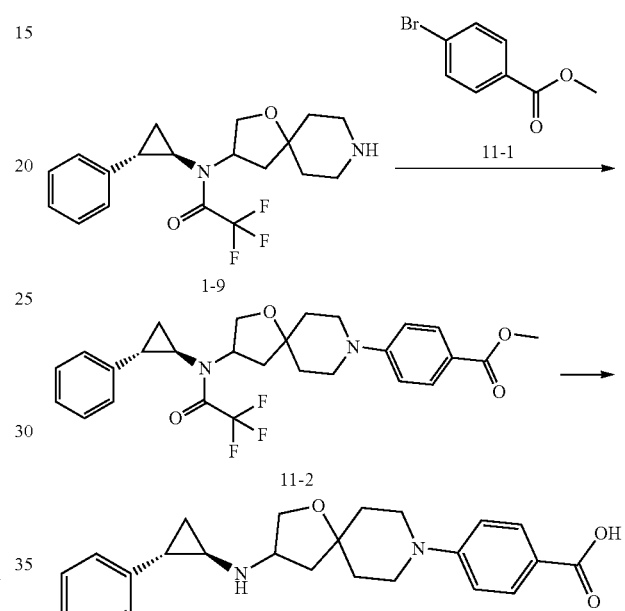

Synthetic Route:

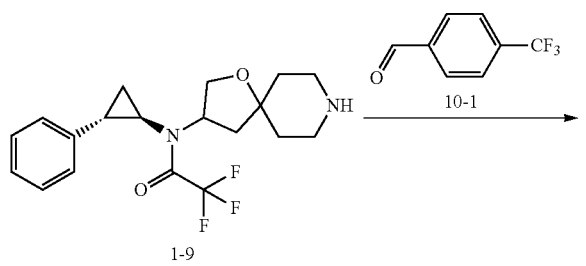

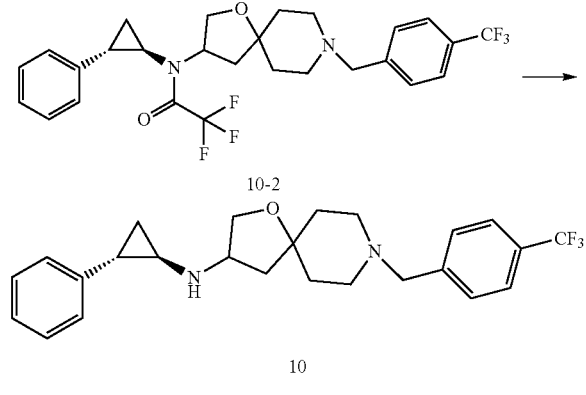

Step 1

Compound 10-1 (70.9 mg, 0.407 mmol) and compound 1-9 (100 mg, 0.271 mmol) were dissolved in anhydrous dichloromethane (2 mL), and glacial acetic acid (48.9 mg, 0.814 mmol) was added to the reaction mixture. The reaction mixture was stirred at 30° C. for 12 hours, sodium triacetoxyborohydride (173 mg, 0.814 mmol) was added thereto, and the reaction mixture was stirred at 30° C. for 1 hour. Saturated sodium bicarbonate solution (20 mL) was added to the reaction mixture, extracted with dichloromethane (10 mL×3), the organic phases were combined and washed with water (10 mL×1) and saturated brine (10 mL×1), dried over anhydrous sodium sulfate, filtered, the filtrate was concentrated, and the crude product was purified by thin layer chromatography (3:1 petroleum ether/ethyl acetate, $R_f$=0.86) to obtain compound 10-2. MS-ESI calculated value [M+H]$^+$ 527, measured value 527.

Step 2

Compound 10-2 (40.0 mg, 76.0 umol) was dissolved in tetrahydrofuran (1 mL), ethanol (1 mL) and water (1 mL), and sodium hydroxide (9.12 mg, 0.228 mmol) was added to the reaction mixture. The reaction mixture was stirred at 60° C. for 2.5 hours, concentrated under reduced pressure to remove the solvent, the residue was diluted with water, and the pH value was adjusted to about 4 with aqueous hydrochloric acid solution (1 mol/L). The hydrochloride of compound 10 was prepared by high performance liquid chromatography (acidic, hydrochloric acid system). $^1$H NMR (400 MHz, CD$_3$OD) δ 7.84-7.80 (m, 4H), 7.35-7.31 (m, 2H), 7.27-7.26 (m, 1H), 7.22-7.19 (m, 2H), 4.46 (s, 2H), 4.23-4.12 (m, 3H), 3.45-3.42 (m, 2H), 3.29-3.25 (m, 2H), 3.04-3.02 (m, 1H), 2.61-2.57 (m, 1H), 2.46-2.41 (m, 1H), 2.20-2.04 (m, 4H), 1.97-1.94 (m, 1H), 1.61-1.59 (m, 1H), 1.47-1.41 (m, 1H). MS-ESI calculated value [M+H]$^+$ 431, measured value 431.

Step 1

Compound 11-1 (87.6 mg, 0.407 mmol) and compound 1-9 (100 mg, 0.271 mmol) were dissolved in anhydrous dioxane (5 mL), and 4,5-bis(di-tert-butylphosphino)-9,9-dimethylxanthene (31.4 mg, 54.3 μmol), tris(dibenzylideneacetone) dipalladium (24.9 mg, 27.1 umol) and cesium carbonate (177 mg, 0.543 mmol) was added to the reaction mixture. The reaction mixture was stirred at 100° C. for 10 hours. Water (10 mL) was added to the reaction mixture, extracted with ethyl acetate (10 mL×3), the combined organic phase was dried over anhydrous sodium sulfate, filtered, and the mother liquor was concentrated. The crude product was purified by thin layer chromatography (3:1 petroleum ether/ethyl acetate, $R_f$=0.40) to obtain compound 11-2. MS-ESI calculated value [M+H]$^+$ 503, measured value 503.

Step 2

Compound 11-2 (35.0 mg, 55.5 μmol) was dissolved in tetrahydrofuran (1 mL), ethanol (1 mL) and water (1 mL), and sodium hydroxide (6.66 mg, 0.166 mmol) was added to the reaction mixture. The reaction mixture was stirred for reaction at 60° C. for 3 hours, and concentrated under reduced pressure to remove the solvent. The residue was diluted with water, and the pH value was adjusted to about 4 with aqueous hydrochloric acid solution (1 mol/L). The hydrochloride of compound 11 was prepared by high performance liquid chromatography (acidic, hydrochloric acid system). $^1$H NMR (400 MHz, CD$_3$OD) δ 8.15-8.13 (d, 2H), 7.64-7.61 (d, J=8.56, 2H), 7.36-7.33 (m, 2H), 7.28-7.22 (m, 3H), 4.25-4.18 (m, 3H), 3.81-3.62 (m, 4H), 3.10-3.06 (m, 1H), 2.63-2.59 (m, 1H), 2.55-2.50 (m, 1H), 2.33-2.32 (m, 1H), 2.20-2.09 (m, 4H), 1.65-1.60 (m, 1H), 1.49-1.45 (m, 1H). MS-ESI calculated value [M+H]$^+$ 393, measured value 393.

Embodiment 12

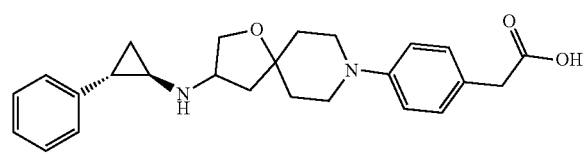 [SMILES: O=C(O)Cc1ccc(N2CCC3(CC2)CC(N[C@@H]2C[C@H]2c2ccccc2)CO3)cc1]

Synthetic Route:

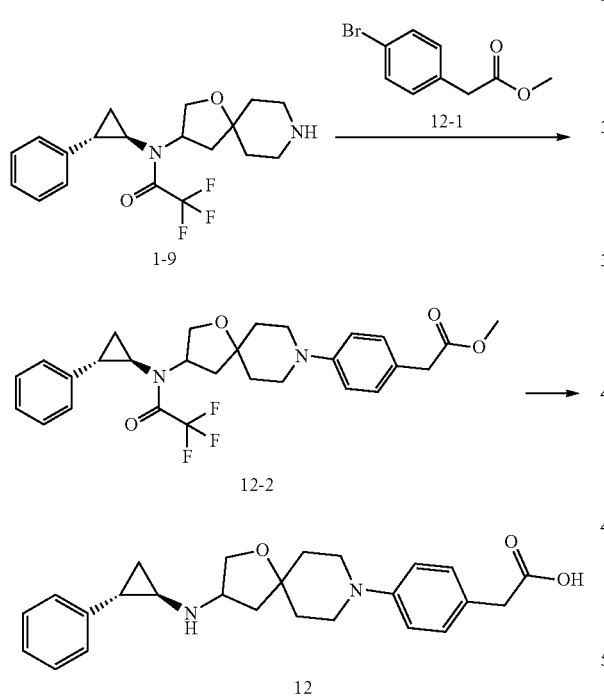

Step 1

Compound 12-1 (219 mg, 0.957 mmol) and compound 1-9 (235 mg, 0.638 mmol) were dissolved in anhydrous dioxane (4 mL), and cesium carbonate (520 mg, 1.59 mmol) and methanesulfonato(2-dicyclohexylphosphino-3,6-dimethoxy-2,4,6-tri-i-propyl-1,1-biphenyl)(2-amino-1,1-biphenyl-2-yl)palladium(II) (57.8 mg, 63.8 μmol) were added to the reaction mixture under nitrogen protection. The reaction mixture was stirred at 100° C. for 14 hours. Water (10 mL) was added to the reaction mixture, extracted with ethyl acetate (10 mL×3), the organic phases were combined, dried over anhydrous sodium sulfate, filtered, and the mother liquor was concentrated. The crude product was purified by thin-layer chromatography (2:1 petroleum ether/ethyl acetate, R$_f$=0.50) to obtain compound 12-2. MS-ESI calculated value [M+H]$^+$ 517, measured value 517.

Step 2 le;2qCompound 12-2 (140 mg, 0.271 mmol) was dissolved in tetrahydrofuran (1 mL), ethanol (1 mL) and water (1 mL), and sodium hydroxide (32.5 mg, 0.813 mmol) was added to the reaction mixture. The reaction mixture was stirred for reaction at 60° C. for 3 hours, and concentrated under reduced pressure to remove the solvent. The residue was diluted with water, and the pH value was adjusted to about 4 with aqueous hydrochloric acid solution (1 mol/L). The hydrochloride of compound 12 was prepared by high performance liquid chromatography (acidic, hydrochloric acid system). $^1$H NMR (400 MHz, CD$_3$OD) δ 7.76-7.73 (d, 2H), 7.56-7.54 (d, J=8.31, 2H), 7.36-7.30 (m, 2H), 7.28-7.22 (m, 3H), 4.30-4.20 (m, 2H), 3.91-3.82 (m, 2H), 3.73 (s, 2H), 3.66-3.59 (m, 2H), 3.34-3.32 (m, 1H), 3.09-3.05 (m, 1H), 2.68-2.64 (m, 1H), 2.58-2.46 (m, 2H), 2.32-2.18 (m, 4H), 1.70-1.64 (m, 1H), 1.48-1.42 (m, 1H). MS-ESI calculated values [M+H]$^+$ 407, measured values 407.

Embodiment 13

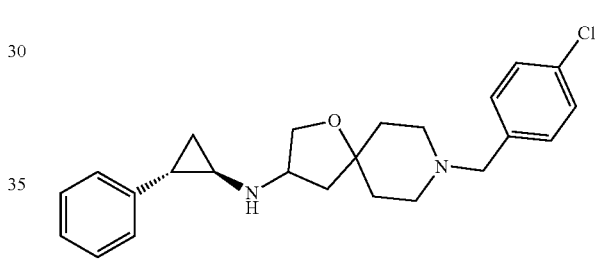

Synthetic Route:

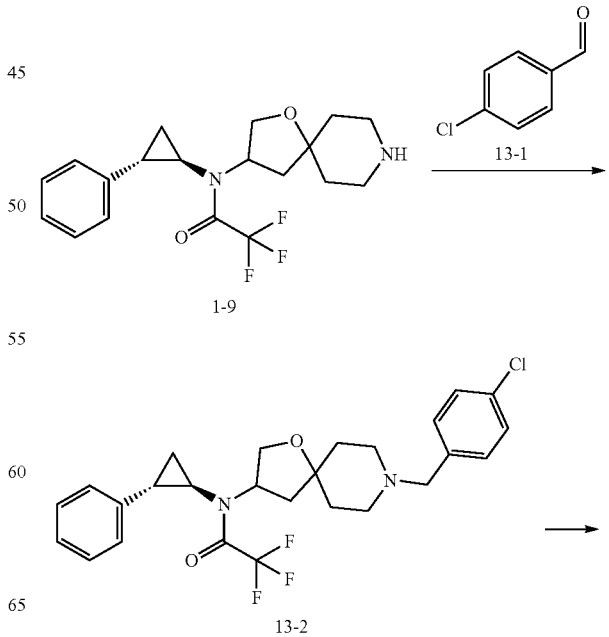

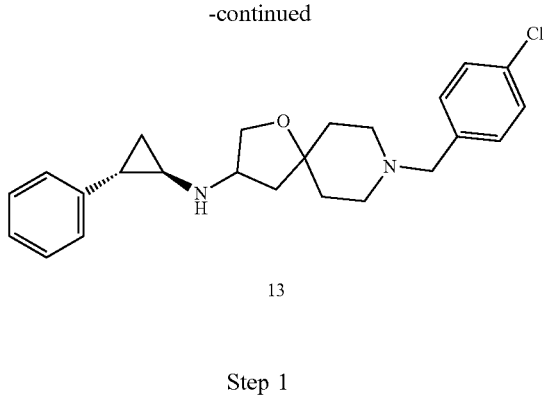

13

Step 1

Compound 1-9 (200 mg, 0.513 mmol) and compound 13-1 (114 mg, 0.814 mmol) were dissolved in anhydrous dichloromethane (5 mL), acetic acid (97.8 mg, 1.63 mmol) at 30° C. for 12 hours, sodium triacetoxyborohydride (345 mg, 1.63 mmol) was added thereto, and the reaction was carried out at 30° C. for 1 hour. The reaction mixture was diluted with dichloromethane (10 mL), and then washed with saturated sodium bicarbonate solution (15 mL×1), water (15 mL×1) and saturated brine (15 mL×1), dried over anhydrous sodium sulfate, filtered, and the mother liquor was concentrated. The product was purified by thin layer chromatography (1:2 petroleum ether/ethyl acetate, $R_f$=0.25) to obtain compound 13-2. MS-ESI calculated values [M+H]$^+$ 493, measured values 493.

Step 2

Compound 13-2 (67.0 mg, 0.136 μmol) was dissolved in a mixed solution of tetrahydrofuran (2 mL), ethanol (2 mL) and water (2 mL), and sodium hydroxide (16.3 mg, 0.408 mmol) was added thereto. The reaction was carried out at 50° C. for 2 hours. The organic phase was removed by concentration under reduced pressure. The residue was dissolved in water (3 mL), and the pH value was adjusted to 4 with hydrochloric acid (1 mol/L), the mixture was purified by high performance liquid chromatography (acidic, hydrochloric acid system) to give the hydrochloride of compound 13. $^1$H NMR (400 MHz, D$_2$O) δ 7.48-7.46 (m, 2H), 7.41-7.39 (m, 2H), 7.35-7.31 (m, 2H), 7.28-7.24 (m, 1H), 7.16-7.14 (m, 2H), 4.30-4.17 (m, 3H), 4.12-4.03 (m, 2H), 3.52-3.33 (m, 2H), 3.18-3.00 (m, 2H), 2.89-3.00 (m, 1H), 2.54-2.48 (m, 1H), 2.42-2.38 (m, 1H), 2.07-1.93 (m, 4H), 1.84-1.70 (m, 1H), 1.55-1.46 (m, 1H), 1.45-1.38 (m, 1H). MS-ESI calculated values [M+H]$^+$ 397, measured values 397.

Embodiment 14

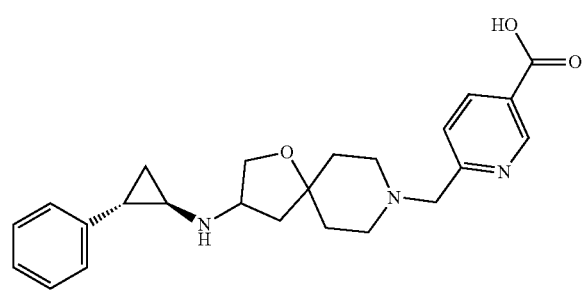 [SMILES: O=C(O)c1ccc(CN2CCC3(CC2)CC(N[C@@H]2C[C@H]2c2ccccc2)CO3)nc1]

Synthetic Route:

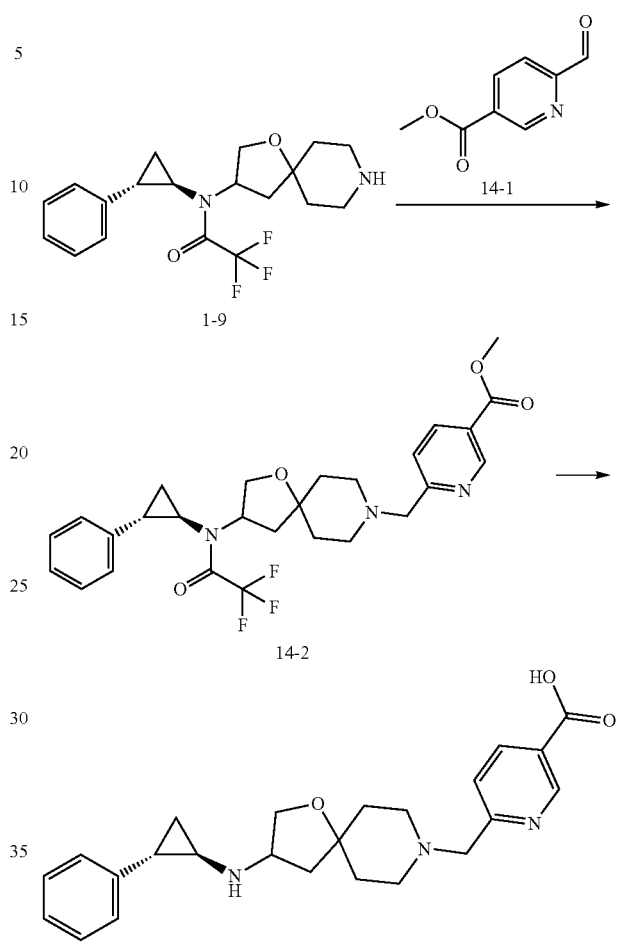

Step 1

Compound 1-9 (200 mg, 0.543 mmol) and compound 14-1 (134 mg, 0.814 mmol) were dissolved in anhydrous dichloromethane (5 mL), acetic acid (97.8 mg, 1.63 mmol) was added thereto, the reaction was carried out at 30° C. for 12 hours, sodium triacetoxyborohydride (345 mg, 1.63 mmol) was added, and the reaction was carried out at 30° C. for 1 hour. The reaction mixture was diluted with dichloromethane (10 mL), and then washed with saturated sodium bicarbonate solution (15 mL×1), water (15 mL×1) and saturated brine (15 mL×1), dried over anhydrous sodium sulfate, filtered, and the mother liquor was concentrated. The crude product was purified by thin layer chromatography (1:2 petroleum ether/ethyl acetate, $R_f$=0.25) to obtain compound 14-2. MS-ESI calculated value [M+H]$^+$ 518, measured value 518.

Step 2

Compound 14-2 (109 mg, 0.210 mmol) was dissolved in a mixed solution of tetrahydrofuran (2 mL), ethanol (2 mL) and water (2 mL), and sodium hydroxide (25.3 mg, 0.632 mmol) was added thereto. The reaction was carried out at 50° C. for 2 hours. The mixture was concentrated under reduced pressure to remove the organic phase. The residue was dissolved in water (10 mL), the pH value was adjusted to 4 with hydrochloric acid (1 mol/L), and the mixture was purified by high performance liquid chromatography (acidic, hydrochloric acid system) to obtain hydrochloride of compound 14. $^1$H NMR (400 MHz, D$_2$O) δ 9.07 (s, 1H), 8.38 (d, J=8.0 Hz, 1H), 7.62 (d, J=8.0 Hz, 1H), 7.29-7.10 (m, 5H), 4.48 (s, 2H), 4.19-4.07 (m, 3H), 3.38-3.28 (m, 4H), 2.89-2.88 (m, 1H), 2.49-2.42 (m, 2H), 2.15-1.86 (m, 5H), 1.36-1.48 (m, 2H). MS-ESI calculated values [M+H]$^+$ 408, measured values 408.

Embodiment 15

Synthetic Route:

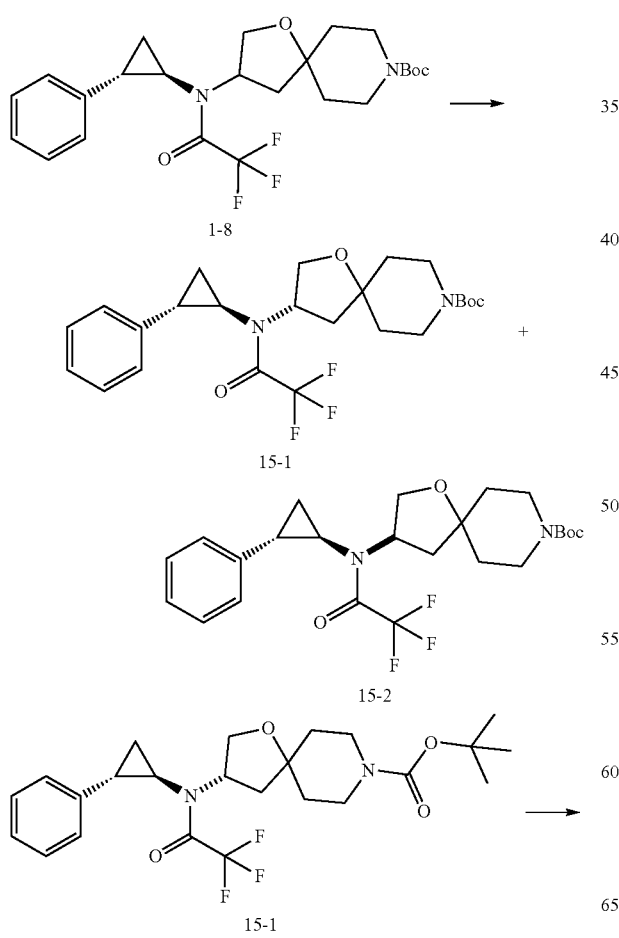

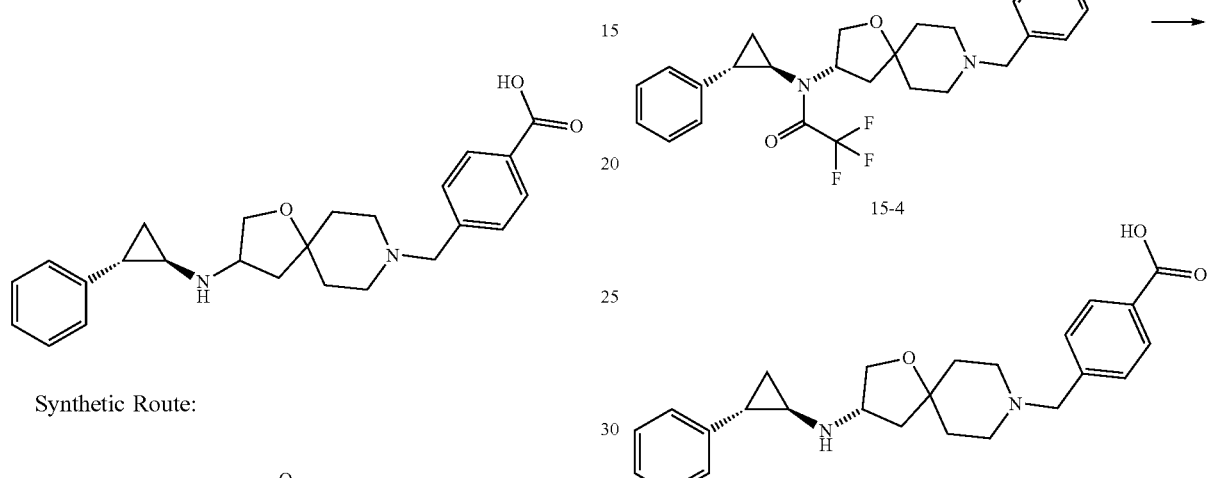

Step 1

Compounds 1-8 was separated by supercritical fluid extraction method [column: Chiralpak AD 250×25 mm I.D., 10 μm; mobile phase: A: carbon dioxide B: methanol (0.1% ammonia); isocratic: B 30%; flow: 60 g/min; column pressure: 100 bar] to obtain compound 15-1 (retention time=0.991 min) and compound 15-2 (retention time=1.248 min). Compound 15-1, calculated value MS-ESI [M+H]$^+$ 469, measured value 469; compound 15-2, MS-ESI calculated value [M+H]$^+$ 469, measured value 469.

Step 2

Compound 15-1 (300 mg, 0.640 mmol) was dissolved in anhydrous dichloromethane (3 mL), cooled to 0° C. in an ice-water bath, and trifluoroacetic acid (1.54 g, 13.5 mmol, 1.0 mL) was added under an ice-water bath, the reaction mixture was stirred at room temperature for 2 hours, and concentrated under reduced pressure to remove the solvent to obtain compound 15-3. MS-ESI calculated value [M+H]$^+$ 369, measured values 369.

Step 3

Compound 15-3 (200 mg, 0.543 mmol) and triethylamine (164 mg, 1.63 mmol) were dissolved in acetonitrile (10 mL), compound 2-5 (186 mg, 0.814 mmol) was added thereto, and the reaction solution was allowed to react at 50° C. for 12 hours, the mixture was concentrated under reduced pressure to remove the solvent, the product was dissolved in dichloromethane (30 mL×1), and then washed with dilute hydrochloric acid (1 mol/L, 10 mL×2) and brine (10 mL×1) in sequence, dried over anhydrous sodium sulfate, filtered, and the filtrate was concentrated. The product was purified by thin layer chromatography (1:1 petroleum ether/ethyl acetate, $R_f$=0.55) to obtain compound 15-4. $^1$H NMR (400 MHz, CDCl$_3$) δ 7.99-7.96 (m, 2H), 7.39-7.37 (m, 2H), 7.31-7.27 (m, 2H), 7.24-7.20 (m, 1H), 7.07-7.05 (m, 2H), 3.92-3.91 (m, 4H), 3.53 (s, 2H), 2.43-2.35 (m, 5H), 2.12-1.98 (m, 2H), 1.74-1.71 (m, 3H), 1.64-1.58 (m, 6H). MS-ESI calculated values [M+H]$^+$ 517, measured values 517.

Step 4

The hydrochloride of Compound 15 was obtained by referring to Step 2 of Embodiment 14. $^1$H NMR (400 MHz, D$_2$O) δ ppm 8.04-8.00 (m, 2H), 7.55-7.53 (m, 2H), 7.33-7.27 (m, 2H), 7.26-7.23 (m, 1H), 7.14-7.12 (m, 2H), 4.37-4.32 (m, 3H), 4.07-4.06 (m, 2H), 3.51-3.33 (m, 2H), 3.19-3.09 (m, 2H), 2.92-2.88 (m, 1H), 2.49-2.34 (s, 2H), 2.03-1.95 (m, 4H), 1.76-1.69 (m, 1H), 1.47-1.37 (m, 2H). MS-ESI calculated values [M+H]$^+$ 407, measured values 407.

Embodiment 16

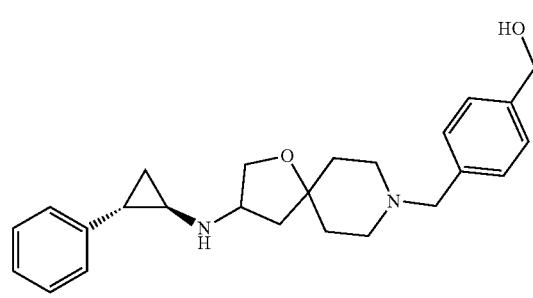

Synthetic Route:

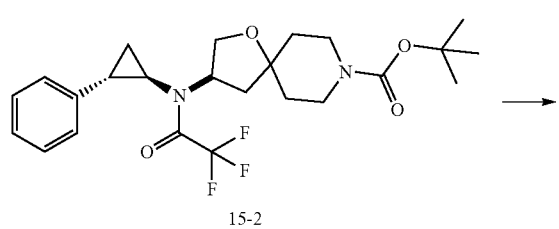

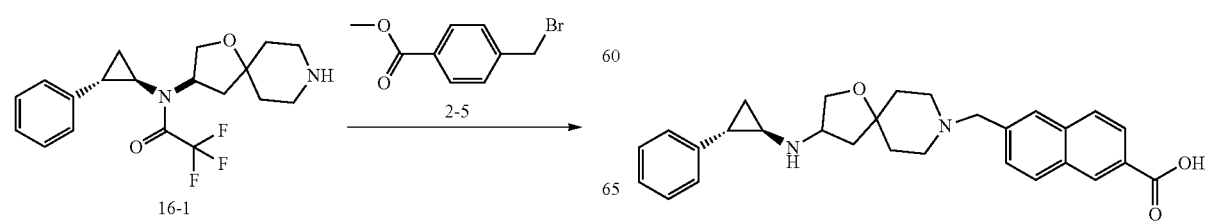

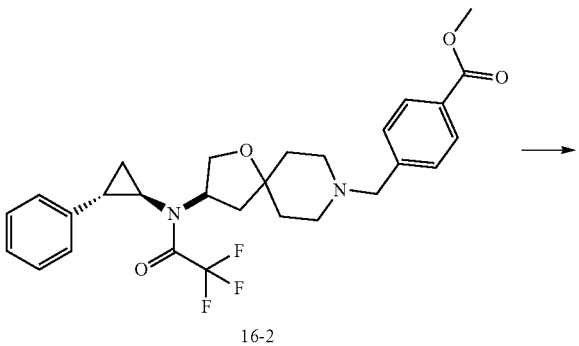

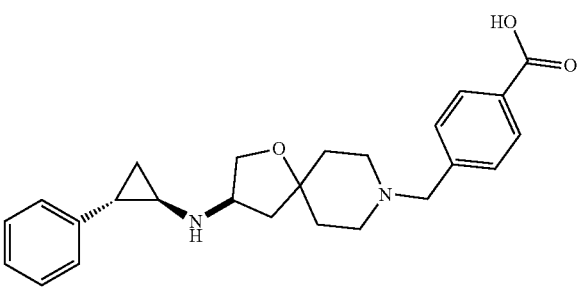 [SMILES: O=C(O)c1ccc(CN2CCC3(CC2)CC(N[C@@H]2C[C@H]2c2ccccc2)CO3)cc1]

Step 1

Compound 16-1 was obtained by referring to Step 2 of Embodiment 15. MS-ESI calculated values [M+H]$^+$ 369, measured values 369.

Step 2

Compound 16-2 was obtained by referring to Step 3 of Embodiment 15. MS-ESI calculated values [M+H]$^+$ 517, measured values 517.

Step 3

The hydrochloride of Compound 16 was obtained by referring to Step 2 of Embodiment 14. $^1$H NMR (400 MHz, D$_2$O) δ 8.04-8.02 (m, 2H), 7.55-7.53 (m, 2H), 7.32-7.23 (m, 3H), 7.14 (m, 2H), 4.37-4.32 (m, 2H), 4.19-4.03 (m, 3H), 3.49-3.33 (m, 2H), 3.22-3.04 (m, 2H), 2.90 (m, 1H), 2.48 (m, 1H), 2.40-2.34 (m, 1H), 2.03-1.92 (m, 4H), 1.77-1.70 (m, 1H), 1.50-1.37 (m, 2H). MS-ESI calculated values [M+H]$^+$ 407, measured values 407.

Embodiment 17

Synthetic Route:

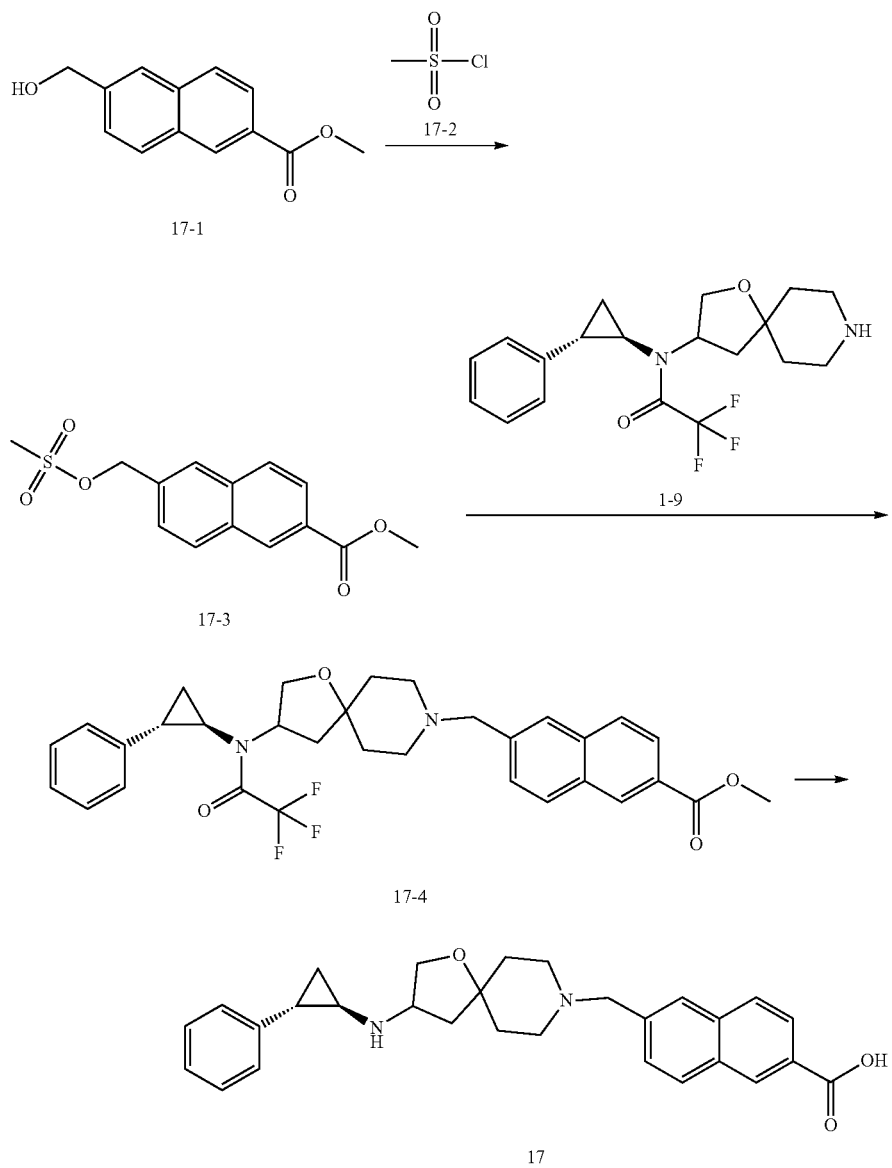

Step 1

Compound 17-1 (100 mg, 0.462 mmol) and triethylamine (140 mg, 1.39 mmol) were dissolved in dichloromethane (5 mL), cooled to 0° C. in an ice-water bath, and compound 17-2 was added dropwise under nitrogen (106 mg, 0.925 mmol), the reaction was carried out at 20° C. for 12 hours, the reaction mixture was quenched by saturated sodium bicarbonate solution (10 mL), the organic phase was washed with saturated brine (10 mL×1), and dried over anhydrous sodium sulfate, filtered, the filtrate was concentrated, and the crude product was purified by thin layer chromatography (1:1 petroleum ether/ethyl acetate, $R_f$=0.53) to obtain compound 17-3. $^1$H NMR (400 MHz, CDCl$_3$) δ 8.60 (s, 1H), 8.10-8.07 (m, 1H), 7.97-7.95 (m, 1H), 7.88-7.86 (m, 2H), 7.59-7.56 (m, 1H), 4.76 (s, 2H), 3.99 (s, 3H), 1.59 (s, 3H).

Step 2

Compound 17-4 was obtained by referring to Step 3 of Embodiment 15. MS-ESI calculated values [M+H]$^+$ 567, [M+Na]$^+$589, measured values 567, 589.

Step 3

The hydrochloride of compound 17 was obtained by referring to Step 2 of Embodiment 14. $^1$H NMR (400 MHz, CD$_3$OD) δ 8.20-8.16 (m, 3H), 8.08-8.05 (m, 1H), 7.77-7.74 (m, 1H), 7.37-7.27 (m, 2H), 8.71 (s, 1H), 7.29-7.27 (m, 1H), 7.22-7.20 (m, 2H), 4.58 (s, 2H), 4.23-4.11 (m, 3H), 3.52-3.36 (m, 4H), 3.05-3.01 (m, 1H), 2.57 (s, 1H), 2.47-2.42 (m, 1H), 2.14-2.11 (m, 4H), 1.97-1.92 (m, 1H), 1.60-1.58 (m, 1H), 1.48-1.43 (m, 1H). MS-ESI calculated values [M+H]$^+$ 457, measured values 457.

Embodiment 18

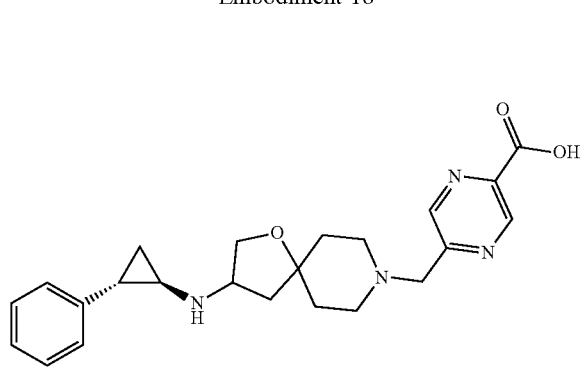

Synthetic Route:

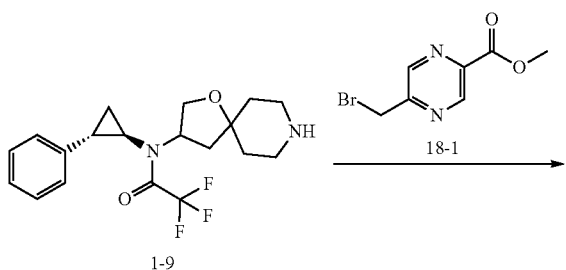

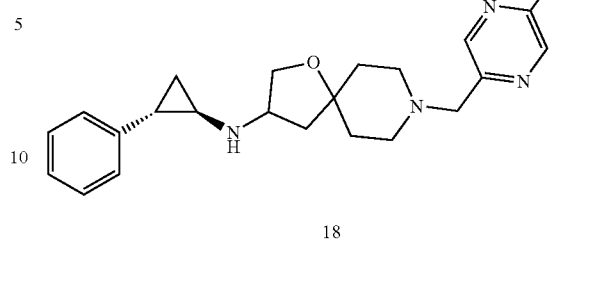

Step 1

Compound 18-2 was obtained by referring to Step 3 of Embodiment 15. MS-ESI calculated values [M+H]$^+$ 519, [M+Na]$^+$541, measured values 519, 541.

Step 2

The hydrochloride of compound 18 was obtained by referring to Step 2 of Embodiment 14. $^1$H NMR (400 MHz, CD$_3$OD) δ 9.36 (s, 1H), 8.86 (s, 1H), 7.35-7.31 (m, 2H), 7.27-7.23 (m, 1H), 7.21-7.19 (m, 2H), 4.71 (s, 2H), 4.25-4.12 (m, 3H), 3.69-3.55 (m, 2H), 3.49-3.36 (m, 2H), 3.04-3.02 (m, 1H), 2.59-2.43 (m, 2H), 2.27-2.07 (m, 4H), 2.01-1.95 (m, 1H), 1.61-1.59 (m, 1H), 1.47-1.41 (m, 1H). MS-ESI calculated values [M+H]$^+$ 409, measured values 409.

Embodiment 19

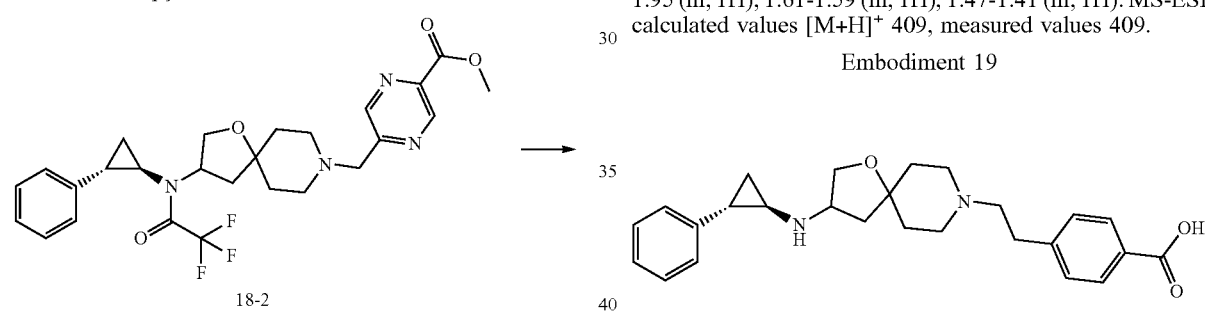

Synthetic Route:

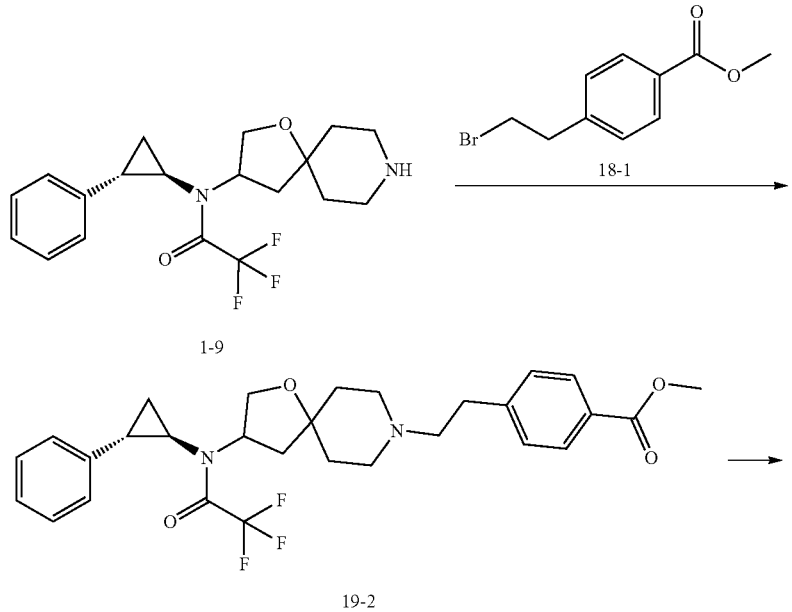

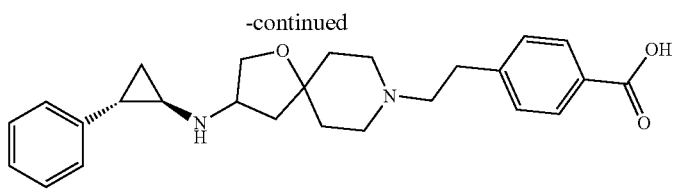

19

Step 1

Compound 19-2 was obtained by referring to Step 3 of Embodiment 15. MS-ESI calculated values [M+H]+ 531, measured values 531.

Step 2

The hydrochloride of compound 19 was obtained by referring to Step 2 of Embodiment 14. ¹H NMR (400 MHz, CD$_3$OD) δ 8.04-8.00 (m, 2H), 7.46-7.44 (m, 2H), 7.36-7.32 (m, 2H), 7.30-7.25 (m, 1H), 7.22-7.20 (m, 2H), 4.27-4.11 (m, 3H), 3.64-3.56 (m, 2H), 3.44-3.40 (m, 2H), 3.31-3.24 (m, 2H), 3.22-3.18 (m, 2H), 3.06-3.03 (m, 1H), 2.60-2.44 (m, 2H), 2.24-2.06 (m, 4H), 1.99-1.91 (m, 1H), 1.62-1.57 (m, 1H), 1.46 (m, 1H). MS-ESI calculated values [M+H]+ 421, measured values 421.

Embodiment 20

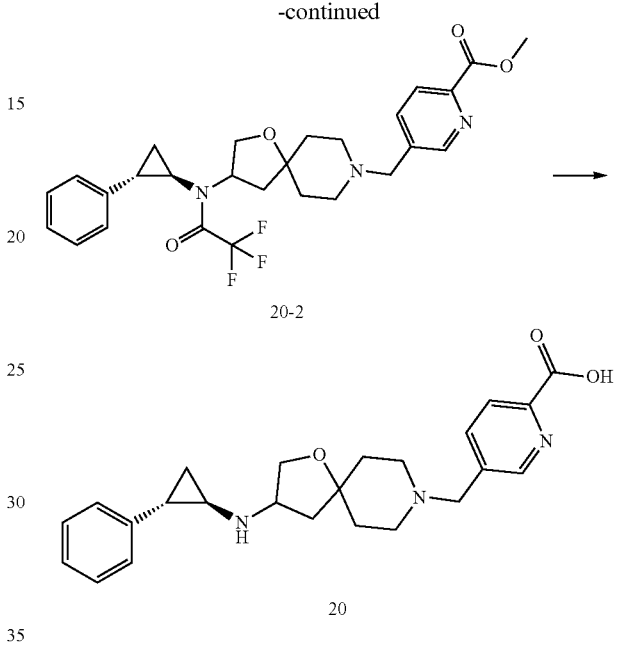

Synthetic Route:

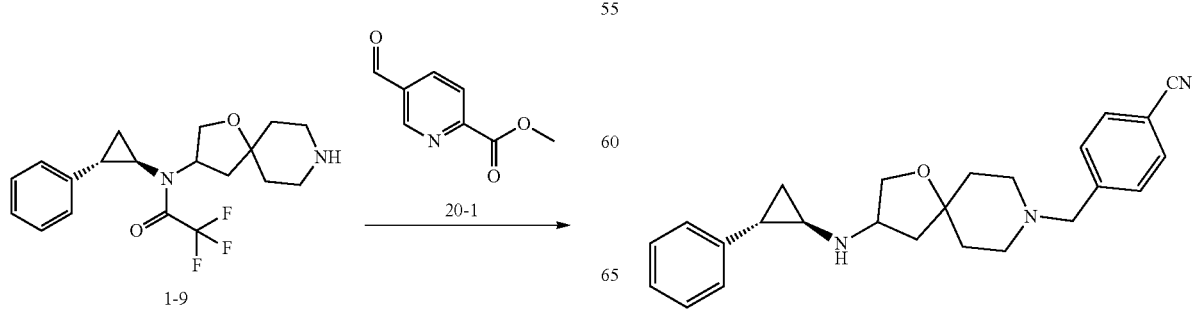

Step 1

Compound 20-2 was obtained by referring to Step 1 of Embodiment 6. MS-ESI calculated values [M+H]+ 518, measured values 518.

Step 2

The hydrochloride of compound 20 was obtained by referring to Step 2 of Embodiment 6. ¹H NMR (400 MHz, CD$_3$OD) δ 9.48-9.32 (m, 1H), 8.75-8.55 (m, 2H), 7.34-7.30 (m, 2H), 7.26-7.24 (m, 1H), 7.22-7.20 (m, 2H), 4.70 (brs, 2H), 4.25-4.18 (m, 3H), 3.42-3.37 (m, 4H), 3.05-3.03 (m, 1H), 2.64-2.62 (m, 1H), 2.45-2.43 (m, 1H), 2.36-2.24 (m, 1H), 2.12-2.06 (m, 4H), 1.65-1.61 (m, 1H), 1.43-1.40 (m, 1H). MS-ESI calculated values [M+H]+ 408, measured values 408.

Embodiment 21

Synthetic Route:

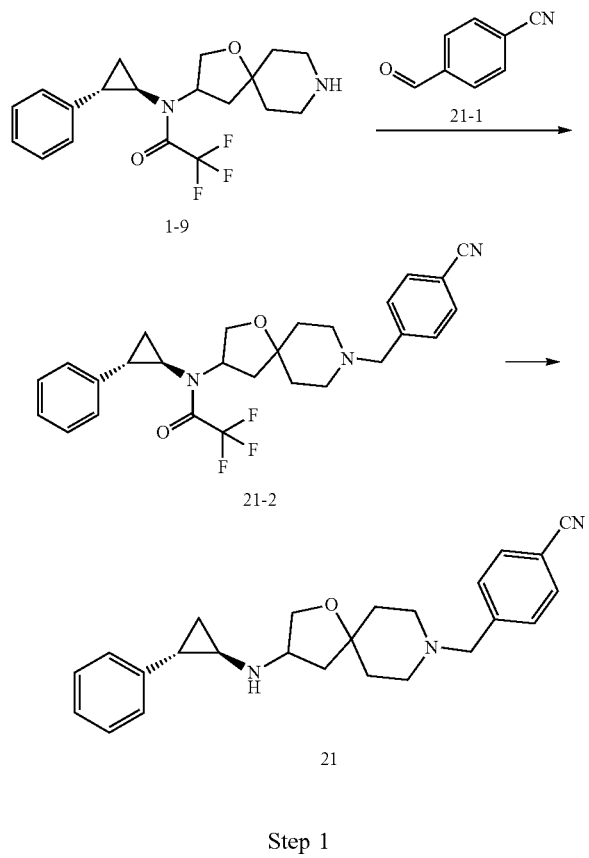

Step 1

Compound 21-2 was obtained by referring to Step 1 of Embodiment 6. MS-ESI calculated values [M+H]⁺ 484, measured values 484.

Step 2

The hydrochloride of compound 21 was obtained by referring to Step 2 of Embodiment 6. $^1$H NMR (400 MHz, CD$_3$OD) δ 7.89-7.87 (m, 2H), 7.82-7.80 (m, 2H), 7.35-7.31 (m, 2H), 7.27-7.25 (m, 1H), 7.23-7.20 (m, 2H), 4.45 (s, 2H), 4.22-4.19 (m, 1H), 4.17-4.15 (m, 2H), 3.50-3.33 (m, 3H), 3.28-3.25 (m, 1H), 3.04-3.02 (m, 1H), 2.63-2.59 (m, 1H), 2.46-2.40 (m, 1H), 2.25-2.17 (m, 1H), 2.14-2.06 (m, 3H), 2.00-1.94 (m, 1H), 1.63-1.61 (m, 1H), 1.47-1.40 (m, 1H). MS-ESI calculated values [M+H]⁺ 388, measured values 388.

Embodiment 22

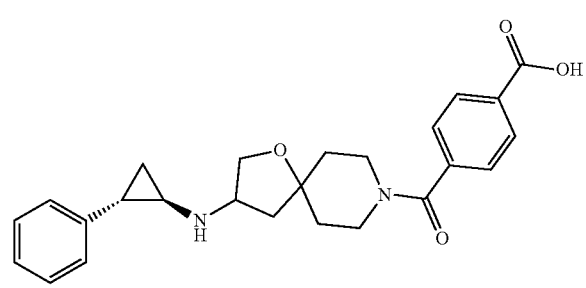 [SMILES: O=C(O)c1ccc(C(=O)N2CCC3(CC2)CC(N[C@@H]2C[C@H]2c2ccccc2)CO3)cc1]

Synthetic Route:

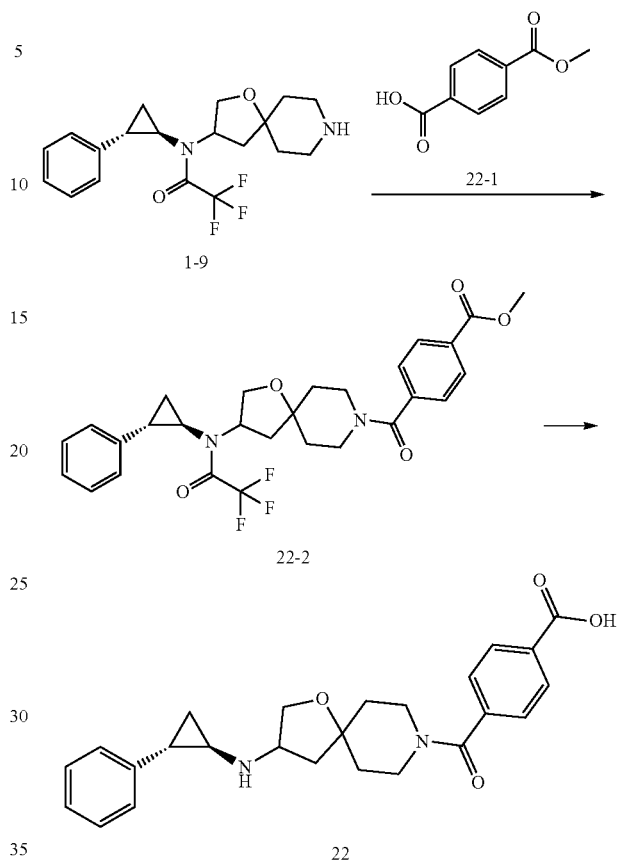

Step 1

Compound 22-1 (102 mg, 0.567 mmol), O-(7-azabenzotriazol-1-yl)-N, N, N, N-tetramethyluronium hexafluorophosphate (294 mg, 0.773 mmol) and NN-diisopropylethylamine (133 mg, 1.03 mmol) were dissolved in N,N-dimethylformamide (8 mL), the reaction mixture was stirred at 27° C. for 0.5 hour, compound 1-9 (190 mg, 0.515 mmol) was added to the reaction mixture, and the new reaction mixture was stirred at 27° C. for 10 hours, then diluted with ethyl acetate (50 mL), and washed with water (50 mL×3) and saturated brine (50 mL×1) in sequence, dried over anhydrous sodium sulfate, filtered, the filtrate was concentrated, and the crude product was purified by thin layer chromatography (1:2 petroleum ether/ethyl acetate, R$_f$=0.6) to obtain compound 22-2. MS-ESI calculated value [M+H]⁺ 531, measured value 531.

Step 2

The hydrochloride of compound 22 was obtained by referring to Step 2 of Embodiment 6. $^1$H NMR (400 MHz, CD$_3$OD) δ 8.12 (d, J=8.0 Hz, 2H), 7.53 (d, J=8.0 Hz, 2H), 7.35-7.29 (m, 2H), 7.26-7.25 (m, 1H), 7.23-7.20 (m, 2H), 4.24-4.18 (m, 2H), 4.13-4.09 (m, 2H), 3.47-3.44 (m, 3H), 3.03-3.02 (m, 1H), 2.59-2.56 (m, 1H), 2.42-2.38 (m, 1H), 2.05-1.99 (m, 1H), 1.93-1.89 (m, 2H), 1.81-1.73 (m, 2H), 1.62-1.58 (m, 1H), 1.46-1.41 (m, 1H). MS-ESI calculated value [M+H]⁺ 421, measured value 421.

Embodiment 23

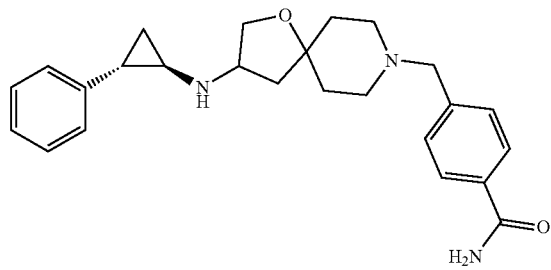 [SMILES: NC(=O)c1ccc(CN2CCC3(CC2)CC(N[C@@H]2C[C@H]2c2ccccc2)CO3)cc1]

Synthetic Route:

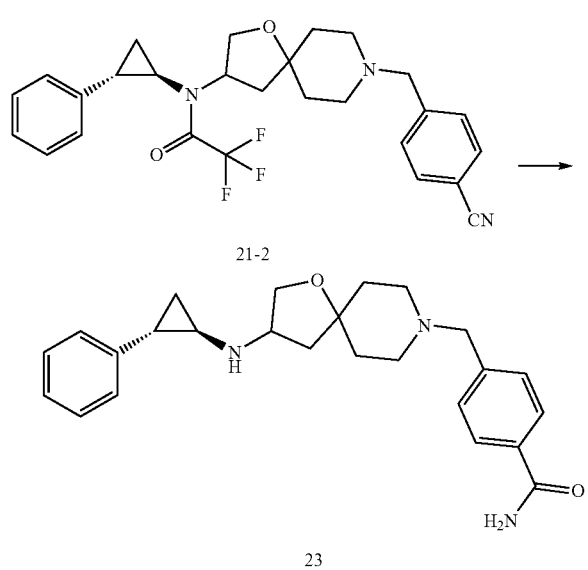

Step 1

Compound 21-2 (100 mg, 0.207 mmol) was dissolved in dimethyl sulfoxide (2 mL), and anhydrous potassium carbonate (85.8 mg, 0.620 mmol) and hydrogen peroxide (30% aqueous solution, 70.3 mg, 0.620 mmol) were added to the reaction mixture and stirred for 12 hours under nitrogen protection at 25° C. The reaction mixture was quenched by adding saturated sodium thiosulfate solution (10 mL), and the mixture was diluted with water (10 mL) and extracted with ethyl acetate (10 mL×3), the organic phase was washed with saturated sodium chloride solution (15 mL×2) and dried over anhydrous sodium sulfate, filtered, and concentrated under reduced pressure. The crude product was purified by high performance liquid chromatography (acidic, hydrochloric acid system) to obtain the hydrochloride of compound 23. $^1$H NMR (400 MHz, CD$_3$OD) δ 7.98 (d, J=8.0 Hz, 2H), 7.68 (d, J=8.0 Hz, 2H), 7.33-7.28 (m, 2H), 7.25-7.17 (m, 3H), 4.40 (s, 2H), 4.22-4.08 (m, 3H), 3.43-3.36 (m, 2H), 3.28-3.14 (m, 2H), 3.02-2.99 (m, 1H), 2.61-2.54 (m, 1H), 2.44-2.22 (m, 1H), 2.20-2.01 (m, 4H), 1.96-1.87 (m, 1H), 1.63-1.56 (m, 1H), 1.47-1.39 (m, 1H). MS-ESI calculated values [M+H]$^+$ 406, measured values 406.

Embodiment 24

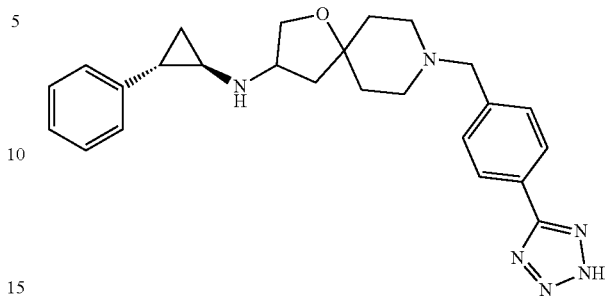

Synthetic Route:

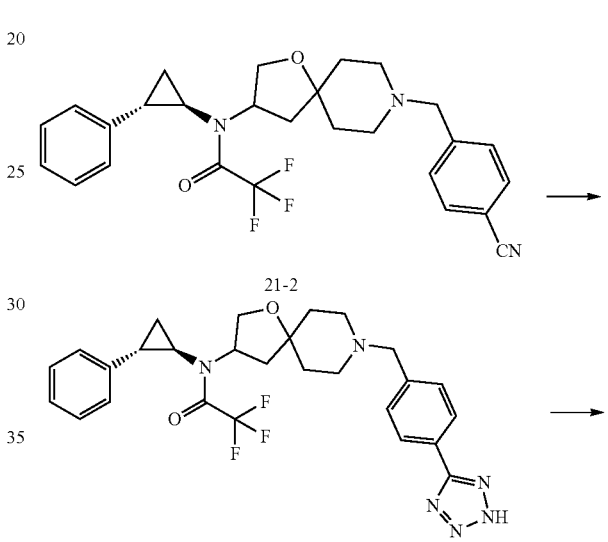

Step 1

Compound 21-2 (90.0 mg, 0.160 mmol) was dissolved in dioxane (3 mL), and trimethylsilyl azide (73.7 mg, 0.640 mmol) and dibutyltin oxide (12.0 mg, 48.0 μmol)) were added to the reaction mixture, the reaction mixture was stirred at 120° C. for 12 hours. Water (10 mL) was added to the mixture at room temperature, then extracted with ethyl acetate (10 mL×3), the organic phases were combined, and washed with saturated sodium chloride solution (20 mL×1), the organic phase was dried over anhydrous sodium sulfate, filtered, and concentrated under reduced pressure to obtain crude compound 24-1. MS-ESI calculated values [M+H]+ 527, measured values 527.

Step 2

Compound 24-1 (101 mg, 0.172 mmol) was dissolved in tetrahydrofuran (2 mL) and absolute ethanol (2 mL), sodium hydroxide (20.6 mg, 0.515 mmol) was dissolved in water (2 mL) and added dropwise to the reaction mixture, the mixture was stirred for 2 hours at 50° C. The reaction mixture was concentrated under reduced pressure to remove the solvent, diluted with water (5 mL), the pH value was adjusted to 4 with hydrochloric acid (1 mol/L), and concentrated under reduced pressure, the crude product was purified by high performance liquid chromatography (acidic, hydrochloric acid system) to obtain the hydrochloride of compound 24. $^1$H NMR (400 MHz, CD$_3$OD) δ 8.19-8.17 (m, 2H), 7.80-7.75 (m, 2H), 7.32-7.17 (m, 5H), 4.40 (s, 2H), 4.20-4.11 (m, 3H), 3.49-3.40 (m, 4H), 3.07-2.94 (m, 1H), 2.68-2.47 (m, 1H), 2.45-2.29 (m, 1H), 2.20-1.99 (m, 4H), 1.94-1.82 (m, 1H), 1.67-1.50 (m, 1H), 1.48-1.33 (m, 1H). MS-ESI calculated value [M+H]+ 431, measured value 431.

Embodiment 25

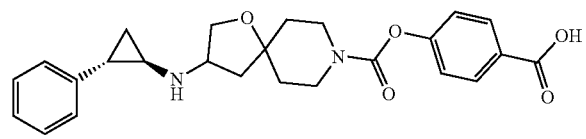 [SMILES: O=C(O)c1ccc(OC(=O)N2CCC3(CC2)CC(N[C@@H]2C[C@H]2c2ccccc2)CO3)cc1]

Synthetic Route:

Step 1

Compound 1-9 (150 mg, 0.407 mmol) was dissolved in acetonitrile (5 mL), compound 25-1 (96.1 mg, 0.448 mol) and triethylamine (124 mg, 1.22 mmol) were added to the reaction mixture, and the temperature of the system was raised to 50° C. and the mixture was stirred for 12 hours. After the solvent was removed by concentration under reduced pressure, the crude product was purified by thin layer chromatography (2:1 petroleum ether/ethyl acetate, R$_f$=0.4) to obtain compound 25-2. MS-ESI calculated values [M+H]+ 547, measured values 547.

Step 2

Compound 25-2 (191 mg, 0.342 mmol) was dissolved in tetrahydrofuran (2 mL) and absolute ethanol (2 mL), and sodium hydroxide (68.4 mg, 1.71 mmol) was dissolved in water (2 mL) and added dropwise to the reaction mixture, the mixture was stirred at 50° C. for 2 hours. The pH value of the reaction solution was adjusted to 5 with hydrochloric acid (1 mol/L) and the mixture was concentrated under reduced pressure. The crude product was purified by high performance liquid chromatography (acidic, hydrochloric acid system) to obtain the hydrochloride of compound 25. $^1$H NMR (400 MHz, CD$_3$OD) δ 8.07-8.03 (m, 2H), 7.35-7.31 (m, 2H), 7.27-7.19 (m, 5H), 4.21-4.06 (m, 3H), 4.03-3.92 (m, 1H), 3.91-3.78 (m, 1H), 3.53-3.36 (m, 2H), 3.05-3.02 (m, 1H), 2.55-2.51 (m, 1H), 2.46-2.40 (m, 1H), 2.03-1.79 (m, 4H), 1.75-1.63 (m, 1H), 1.59-1.53 (m, 1H), 1.47-1.42 (m, 1H). MS-ESI calculated value [M+H]+ 437, measured value 437.

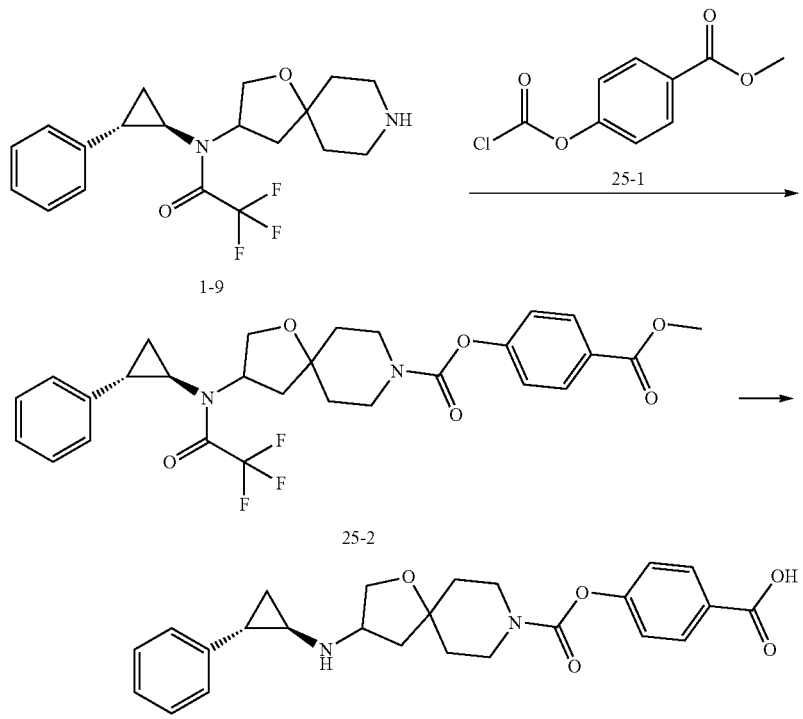

Embodiment 26

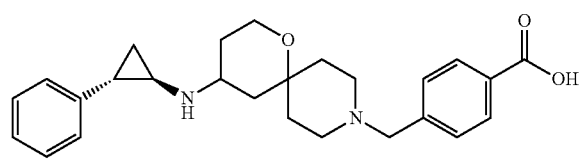 [SMILES: O=C(O)c1ccc(CN2CCC3(CC2)CC(N[C@@H]2C[C@H]2c2ccccc2)CCO3)cc1]

Synthetic Route:

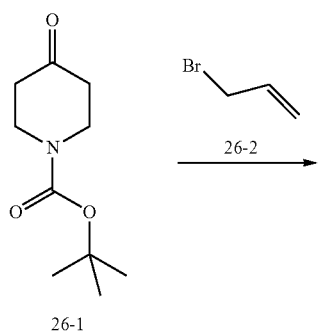

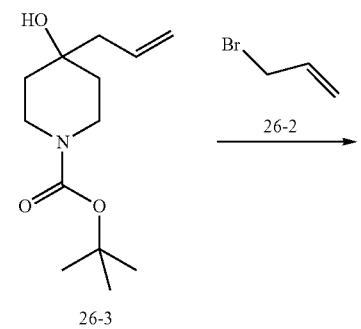

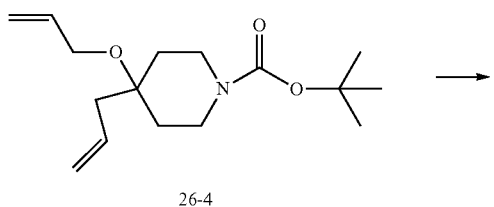

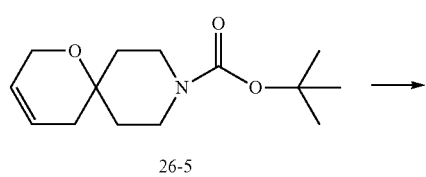

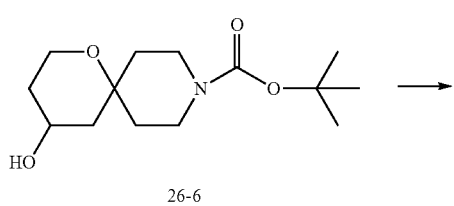

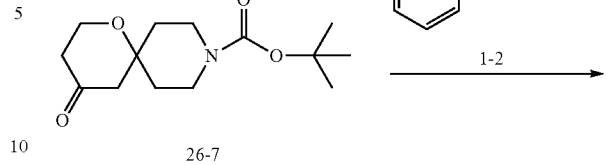

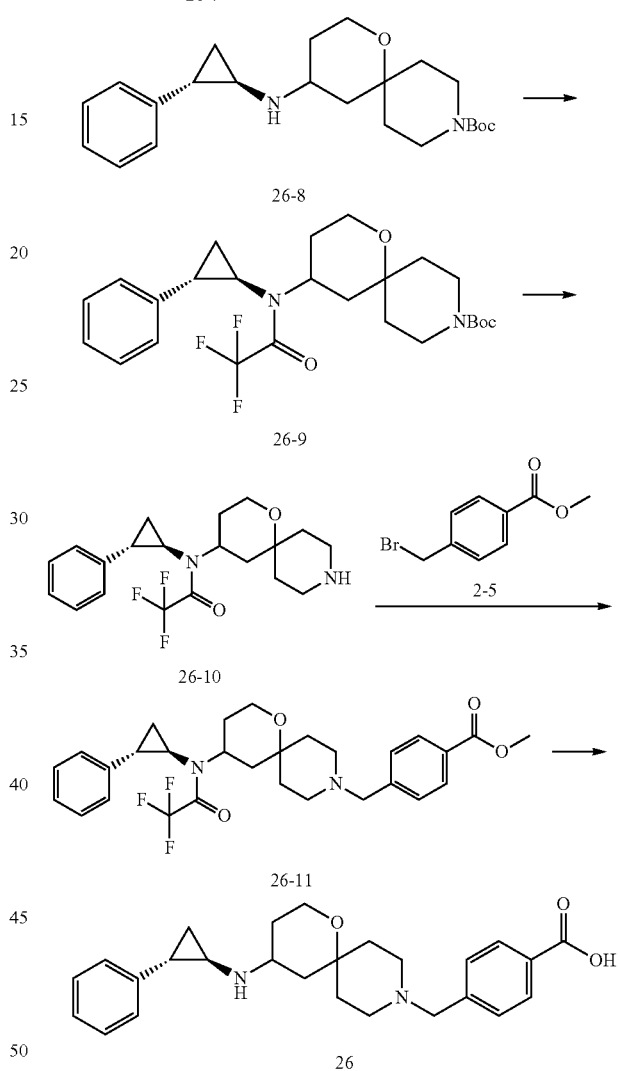

Step 1

Compound 26-1 (50.0 g, 0.251 mol) was dissolved in anhydrous tetrahydrofuran (150 mL) and water (150 mL), and ammonium chloride (49.9 g, 0.934 mol) and zinc powder (49.2 g, 0.753 mol) were added to the reaction mixture at 0° C. Then compound 26-2 (91.1 g, 0.753 mol) was slowly added dropwise at 0° C. The reaction mixture was stirred at 20° C. for 12 hours. After filtration, the filtrate was extracted with ethyl acetate (100 mL×3), the organic phases were combined, dried over anhydrous sodium sulfate, filtered, the filtrate was concentrated, and the crude product was purified by column chromatography (3:1 petroleum ether/ethyl acetate, $R_f$=0.47) to obtain compound 26-3.

¹H NMR (400 MHz, CD₃OD) δ 5.88-5.80 (m, 1H), 5.18-5.10 (m, 2H), 3.95-3.64 (m, 2H), 3.28-3.02 (m, 2H), 2.23-2.21 (m, 2H), 1.58-1.48 (m, 4H), 1.45-1.44 (m, 9H).

Step 2

Compound 26-3 (2.00 g, 8.29 mmol) was dissolved in N,N-dimethylformamide (20 mL), and sodium hydrogen (60%, 0.994 mg, 24.9 mmol) was added to the reaction mixture at 0° C. under nitrogen protection, then compound 26-2 (3.01 g, 24.9 mmol) was added thereto under nitrogen protection. The reaction mixture was stirred at 25° C. for 2 hours. Saturated ammonium chloride solution (200 mL) was added to the reaction mixture, and the mixture was extracted with ethyl acetate (100 mL×3), the organic phases were combined, dried over anhydrous sodium sulfate, filtered, the filtrate was concentrated, and the crude product was purified by column chromatography (10:1 petroleum ether/ethyl acetate, $R_f$=0.60) to obtain compound 26-4.

Step 3

Compound 26-4 (2.15 g, 7.64 mmol) was dissolved in dichloromethane (20 mL), and (1,3-dimethylimidazolidin-2-yliene) (2-isopropyloxybenzylidene) ruthenium ruthenium (VI) chloride (0.479 g, 0.764 mmol). The reaction mixture was stirred at 25° C. for 3 hours. The reaction was quenched by adding water (100 mL), and extracted with ethyl acetate (100 mL×3), the organic phases were combined, washed with saturated brine (100 mL), dried over anhydrous sodium sulfate, filtered, and concentrated, the crude product was purified by column chromatography (10:1 petroleum ether/ethyl acetate, $R_f$=0.51) to obtain compound 26-5. ¹H NMR (400 MHz, CD₃OD) δ 5.68-5.61 (m, 2H), 4.04-4.03 (m, 2H), 3.71-3.60 (m, 2H), 3.12-3.06 (m, 2H), 1.93-1.90 (m, 2H), 1.78-1.68 (m, 2H), 1.62-1.61 (m, 1H), 1.39 (s, 9H), 1.37-1.36 (m, 1H).

Step 4

Compound 26-5 (1.87 g, 7.38 mmol) was dissolved in anhydrous tetrahydrofuran (10 mL), and borane-tetrahydrofuran (1M, 22.1 mL) was added to the reaction mixture at 0° C. under nitrogen protection. The reaction mixture was stirred at 30° C. for 7 hours. Sodium hydroxide (3.54 g, 88.6 mmol), water (10 mL) and hydrogen peroxide (27.1 g, 0.295 mol) were added to the reaction mixture at 0° C. The reaction mixture was stirred for reaction at 30° C. for 1 hour. The reaction mixture was quenched with water (100 mL), extracted with ethyl acetate (100 mL×3), the organic phases were combined and washed with saturated brine (100 mL×1). The mixture was dried over anhydrous sodium sulfate, filtered, concentrated, the crude product was purified by column chromatography (2:1 petroleum ether/ethyl acetate, $R_f$=0.20) to obtain compound 26-6. ¹H NMR (400 MHz, CD₃OD) δ 3.79-3.65 (m, 4H), 3.15-2.94 (m, 2H), 1.82-1.74 (m, 3H), 1.67-1.53 (m, 6H), 1.38 (s, 9H).

Step 5

Compound 26-6 (1.65 g, 6.08 mmol) was dissolved in anhydrous dichloromethane (20 mL), and pyridinium dichromate (4.58 g, 12.2 mmol) was added to the reaction mixture at 0° C. under nitrogen protection. The reaction mixture was stirred for reaction at 30° C. for 12 hours. Then the mixture was filtered, the filtrate was extracted with dichloromethane (80 mL×1), the organic phases were combined, and washed with hydrochloric acid (1 mol/L, 50 mL) and saturated sodium chloride (100 mL×1). The mixture was then dried over anhydrous sodium sulfate, filtered, and concentrated, the crude product was purified by column chromatography (2:1 petroleum ether/ethyl acetate, $R_f$=0.59) to obtain compound 26-7. ¹H NMR (400 MHz, CD₃OD) δ 4.03-4.00 (m, 2H), 3.83-3.81 (m, 2H), 3.22-3.16 (m, 2H), 2.53-2.48 (m, 2H), 1.93-1.77 (m, 4H), 1.58-1.52 (m, 2H), 1.48-1.47 (m, 9H). MS-ESI calculated value [M−Boc+H]⁺170, [M−56+H]⁺214, measured value 170, 214.

Step 6

Compound 26-7 (240 mg, 0.891 mmol) and compound 1-2 (142 mg, 1.07 mmol) were dissolved in dichloromethane (3 mL), glacial acetic acid (53.5 mg, 0.891 mol) was added to the reaction mixture, the reaction mixture was stirred and allowed to react at 25° C. for 10 hours, and then sodium triacetoxyborohydride (378 mg, 1.78 mmol) was added to the reaction mixture, and the reaction was carried out for another 2 hours. The reaction was quenched by adding saturated sodium bicarbonate solution (20 mL) at 25° C., and the mixture was extracted with dichloromethane (20 mL×3), the organic phase was washed with saturated sodium chloride solution (30 mL×1) and dried over anhydrous sodium sulfate, filtered, and concentrated under reduced pressure to remove the solvent, the crude product was purified by thin layer chromatography (1:1 petroleum ether/ethyl acetate, $R_f$=0.3) to obtain compound 26-8. MS-ESI calculated value [M+H]⁺ 387, measured value 387.

Step 7

Compound 26-8 (1.05 g, 2.72 mmol) was dissolved in dichloromethane (10 mL), trifluoroacetic anhydride (856 mg, 4.07 mmol) and N,N-diisopropylethylamine (527 mg, 4.07 mmol) were added thereto and stirred at 25° C. for 12 hours. Dichloromethane (50 mL) was added to the reaction mixture, the reaction mixture was then diluted, and the organic phase was washed with hydrochloric acid (1 mol/L 30 mL×1) and saturated sodium chloride solution (30.0 mL×1) respectively, and then dried over anhydrous sodium sulfate, filtered, concentrated under reduced pressure to remove the solvent, the crude product was purified by thin layer chromatography (3:1 petroleum ether/ethyl acetate, $R_f$=0.5) to obtain compound 26-9. 1H NMR (400 MHz, CDCl₃) δ 7.34-7.30 (m, 2H), 7.27-7.23 (m, 1H), 7.15-7.02 (m, 2H), 4.48-4.19 (m, 1H), 3.90-3.62 (m, 4H), 3.22-3.18 (m, 1H), 3.10-2.96 (m, 1H), 2.41-2.26 (m, 1H), 2.25-2.10 (m, 2H), 2.00-1.94 (m, 1H), 1.83-1.69 (m, 3H), 1.52-1.45 (m, 12H), 1.41-1.37 (m, 1H), 1.31-1.26 (m, 1H). MS-ESI calculated values [M+Na]⁺505, measured values 505.

Step 8

Compound 26-9 (160 mg, 0.305 mmol) was dissolved in dichloromethane (2 mL), trifluoroacetic acid (104 mg, 0.914 mmol) was added at 0° C., and the reaction mixture was stirred at 25° C. for 1 hour. The reaction mixture was concentrated under reduced pressure to obtain the crude compound 26-10. MS-ESI calculated value [M+H]⁺ 383, measured value 383.

Step 9

Compound 26-10 (200 mg, 0.403 mmol) was dissolved in acetonitrile (3 mL), triethylamine (122 mg, 1.21 mmol) was added to the reaction mixture, and the reaction mixture was stirred at 25° C. for 0.5 hour, then compound 2-5 (102 mg, 0.443 mol) was added to the reaction mixture, the system was heated to 50° C. and allowed to react under stirring for 12 hours. After concentration under reduced pressure to remove the solvent, the crude product was purified by thin layer chromatography (2:1 petroleum ether/ethyl acetate, $R_f$=0.5) to obtain compound 26-11. MS-ESI calculated value [M+H]$^+$ 531, measured value 531.

Step 10

Compound 26-11 (162 mg, 0.301 mmol) was dissolved in tetrahydrofuran (2 mL) and absolute ethanol (2 mL), and sodium hydroxide (36.1 mg, 0.902 mmol) was dissolved in water (2 mL) and added dropwise to the mixture, the mixture was stirred at 50° C. for 2 hours. The pH value of the reaction mixture was adjusted to 5 with hydrochloric acid (1 mol/L) and the reaction mixture was concentrated under reduced pressure. The crude product was separated and purified by high performance liquid chromatography (acidic, hydrochloric acid system) to obtain the hydrochloride of compound 26. $^1$H NMR (400 MHz, CD$_3$OD) δ 8.14-8.12 (m, 2H), 7.70-7.68 (m, 2H), 7.34-7.17 (m, 5H), 4.41 (s, 2H), 4.02-3.87 (m, 1H), 3.84-3.60 (m, 2H), 3.43-2.32 (m, 3H), 3.23-3.08 (m, 1H), 3.04-2.89 (m, 1H), 2.67-2.42 (m, 2H), 2.23-1.93 (m, 3H), 1.86-1.43 (m, 6H). MS-ESI calculated value [M+H]$^+$ 421, measured value 421.

Embodiment 27

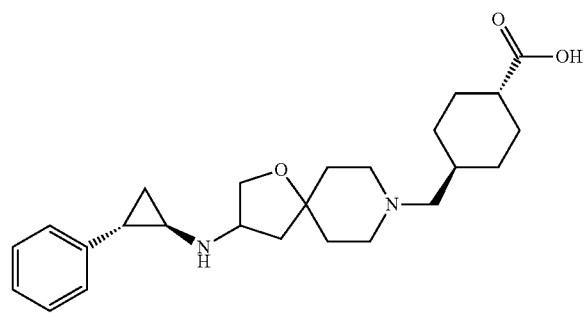 [SMILES: O=C(O)[C@H]1CC[C@H](CN2CCC3(CC2)CC(N[C@@H]2C[C@H]2c2ccccc2)CO3)CC1]

Synthetic Route:

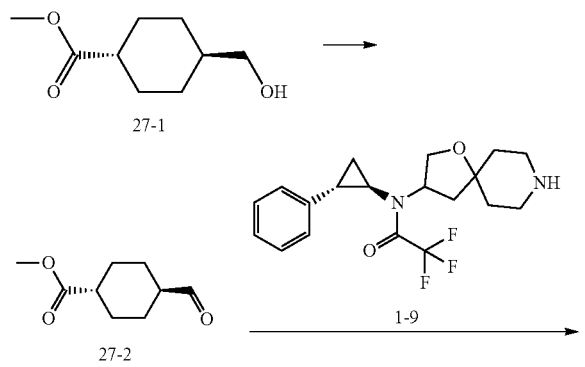

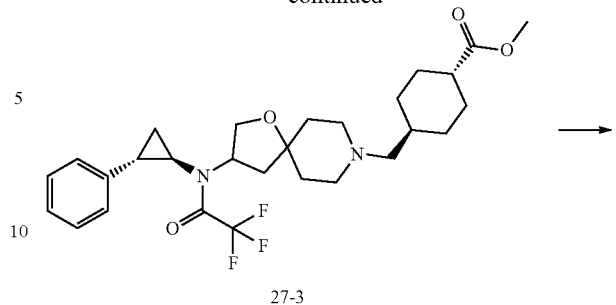

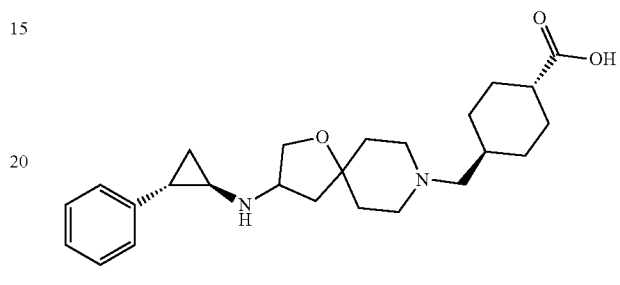

Step 1

Compound 27-1 (200 mg, 1.16 mmol) was dissolved in anhydrous tetrahydrofuran (6 mL) and cooled to 0° C., Dess-Martin periodinane (532 mg, 1.25 mmol) was added to the solution, and the reaction mixture was stirred at 29° C. for 3 hours. The reaction mixture was quenched by adding saturated sodium thiosulfate (30 mL) and extracted with ethyl acetate (30 mL×2). The organic phases were combined and washed with saturated sodium chloride solution (50 mL×1). 1)], then dried over anhydrous sodium sulfate, filtered, and concentrated under reduced pressure to obtain crude product of compound 27-2. $^1$H NMR (400 MHz, CDCl$_3$) δ 9.56 (s, 1H), 3.61 (s, 3H), 2.24-2.14 (m, 2H), 2.05-1.98 (m, 4H), 1.48-1.39 (m, 2H), 1.28-1.21 (m, 2H).

Step 2

Compound 27-3 was obtained by referring to Step 1 of Embodiment 6. MS-ESI calculated values [M+H]$^+$ 523, measured values 523.

Step 3

The hydrochloride of compound 27 was obtained by referring to Step 2 of Embodiment 6. $^1$H NMR (400 MHz, D$_2$O) δ 7.34-7.30 (m, 2H), 7.26-7.23 (m, 1H), 7.16-7.14 (m, 2H), 4.20-4.19 (m, 1H), 4.13-4.04 (m, 2H), 3.53-3.38 (m, 2H), 3.07-2.98 (m, 3H), 2.92-2.90 (m, 2H), 2.58-2.51 (m, 1H), 2.43-2.37 (m, 1H), 2.30-2.23 (m, 1H), 2.11-2.08 (m, 1H), 2.03-1.92 (m, 5H), 1.84-1.75 (m, 4H), 1.49-1.46 (m, 1H), 1.42-1.30 (m, 3H), 1.06-0.97 (m, 2H). MS-ESI calculated value [M+H]$^+$ 413, measured value 413.

Embodiment 28

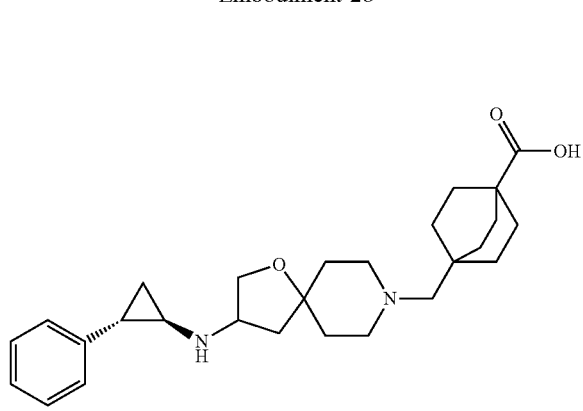

Synthetic Route:

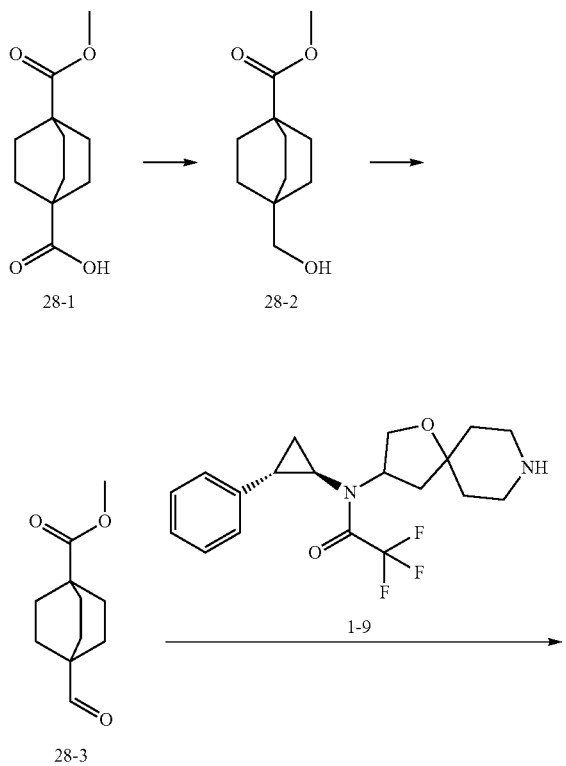

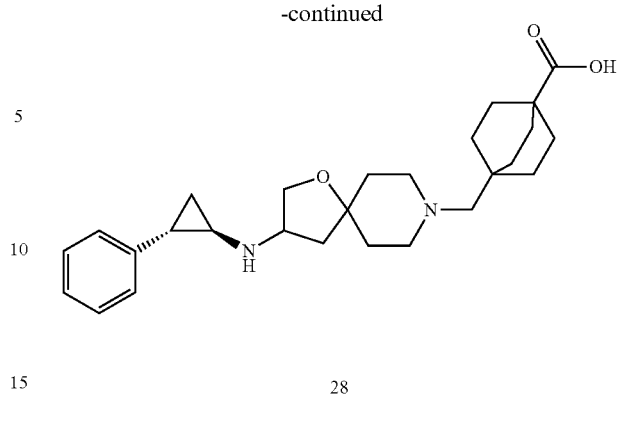

Step 1

Compound 28-1 (2.00 g, 9.42 mmol) was dissolved in anhydrous tetrahydrofuran (50 mL), N,N-carbonyldiimidazole (1.53 g, 9.42 mmol) was added thereto, and the reaction mixture was stirred at 25° C. for 1 hour. After cooling the mixture to 0° C., sodium borohydride (357 mg, 9.42 mmol) was added thereto, and the reaction mixture was stirred at 25° C. for 1 hour. The reaction mixture was quenched by adding saturated sodium bicarbonate (30 mL) and then extracted with ethyl acetate (30 mL×3), the organic phases were combined and dried over anhydrous sodium sulfate, filtered, concentrated under reduced pressure, and the residue was purified by column chromatography (1:2 petroleum ether/ethyl acetate, $R_f$=0.68) to obtain compound 28-2. $^1$H NMR (400 MHz, CDCl$_3$) δ 3.62 (s, 3H), 3.26 (s, 2H), 1.79-1.75 (m, 6H), 1.45-1.41 (m, 6H).

Step 2

Compound 28-3 was obtained by referring to Step 1 of Embodiment 27. $^1$H NMR (400 MHz, CDCl$_3$) δ 9.39 (s, 1H), 3.59 (s, 3H), 1.80-1.76 (m, 6H), 1.63-1.59 (m, 6H).

Step 3

Compound 28-4 was obtained by referring to Step 1 of Embodiment 6. MS-ESI calculated values [M+H]$^+$ 549, measured values 549.

Step 4

The hydrochloride of compound 28 was obtained by referring to Step 2 of Embodiment 6. $^1$H NMR (400 MHz, D$_2$O) δ 7.36-7.32 (m, 2H), 7.28-7.25 (m, 1H), 7.17-7.15 (m, 2H), 4.22-4.18 (m, 1H), 4.12-4.05 (m, 2H), 3.51-3.42 (m, 2H), 3.23-3.08 (m, 2H), 3.03-2.92 (m, 3H), 2.53-2.38 (m, 2H), 2.21-2.06 (m, 1H), 1.96-1.85 (m, 4H), 1.78-1.75 (m, 6H), 1.57-1.54 (m, 6H), 1.51-1.47 (m, 1H), 1.44-1.39 (m, 1H). MS-ESI calculated values [M+H]$^+$ 439, measured values 439.

Embodiment 29

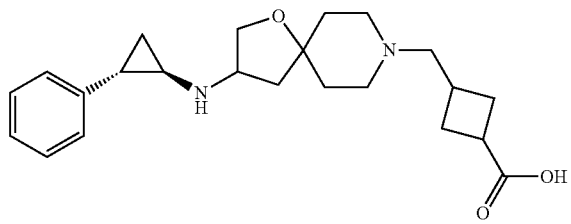 [SMILES: O=C(O)C1CC(CN2CCC3(CC2)CC(N[C@@H]2C[C@H]2c2ccccc2)CO3)C1]

Synthetic Route:

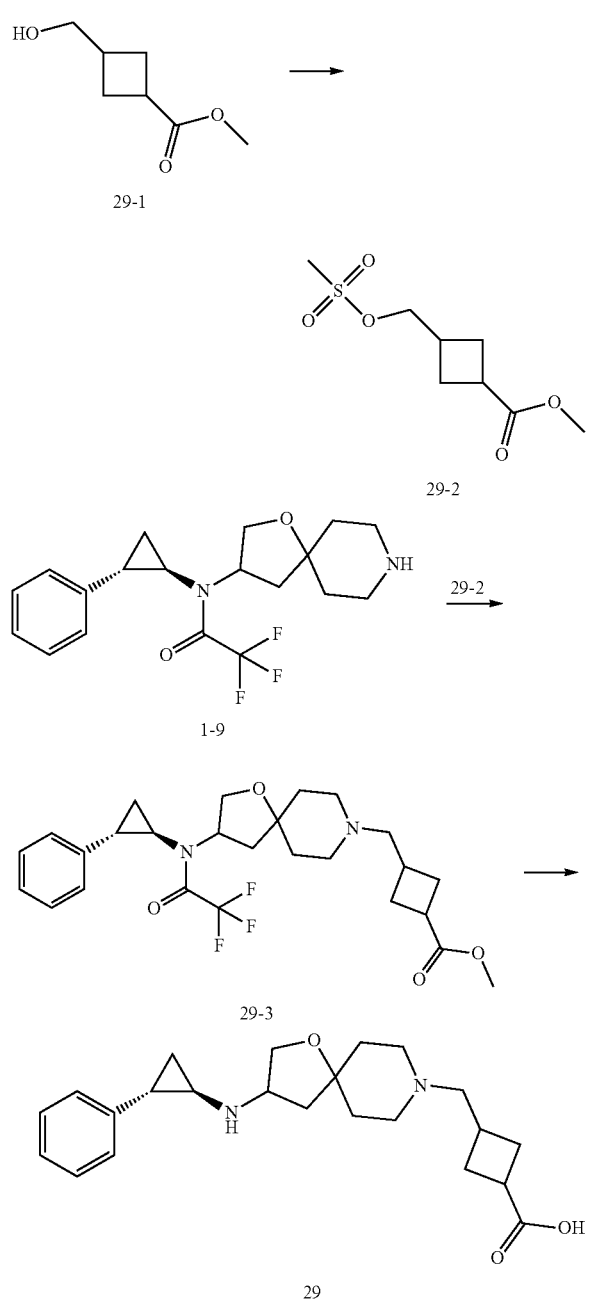

Step 1

Compound 29-1 (100 mg, 0.694 mmol) was dissolved in dichloromethane (2 mL), after cooling to 0° C., methanesulfonyl chloride (79.5 mg, 0.694 mmol) and N,N-diisopropylethylamine (179 mg, 1.39 mmol) were added to the mixture, and the mixture was stirred for 2 hours at 25° C. under nitrogen protection. The reaction was quenched by adding saturated sodium bicarbonate solution (10 mL), and the mixture was extracted with ethyl acetate (10 mL×3), the organic phase was washed with saturated sodium chloride solution (20 mL×1) and dried over anhydrous sodium sulfate, filtered, and concentrated under reduced pressure to obtain a crude product of compound 29-2.

Step 2

Compound 29-2 (70.0 mg, 0.315 mmol) and compound 1-9 (105 mg, 0.286 mmol) were dissolved in N,N-dimethylformamide (2 mL), and N,N-diisopropylethylamine (111 mg, 0.859 mmol) and potassium iodide (9.51 mg, 57.3 μmol) were added to the reaction mixture, and the system was heated to 50° C. and allowed to react under stirring for 12 hours. The reaction mixture was diluted with water (20 mL), and then extracted with ethyl acetate (10 mL×3), the organic phase was washed with saturated sodium chloride solution (15 mL×1), dried over anhydrous sodium sulfate, filtered, and concentrated under reduced pressure to remove the solvent, and then the crude product was purified by a thin layer chromatography (1:1 petroleum ether/ethyl acetate, $R_f$=0.2) to obtain compound 29-3. MS-ESI calculated value $[M+H]^+$ 495, measured value 495.

Step 3

Compound 29-3 (71.0 mg, 0.123 mmol) was dissolved in tetrahydrofuran (2 mL) and absolute ethanol (2 mL), sodium hydroxide (24.5 mg, 0.613 mmol) was dissolved in water (2 mL) and added dropwise to the mixture, then the mixture was stirred at 50° C. for 2 hours. The pH value of the reaction mixture was adjusted to 5 with hydrochloric acid (1 mol/L) and the mixture was concentrated under reduced pressure. The crude product was separated and purified by high performance liquid chromatography (acidic, hydrochloric acid system) to obtain the hydrochloride of compound 29. $^1$H NMR (400 MHz, D$_2$O) δ 7.41-7.37 (m, 2H), 7.34-7.30 (m, 1H), 7.22-7.20 (m, 2H), 4.29-4.23 (m, 1H), 4.20-4.09 (m, 2H), 3.55-3.33 (m, 2H), 3.28-2.96 (m, 6H), 2.90-2.68 (m, 1H), 2.63-2.54 (m, 1H), 2.50-2.42 (m, 3H), 2.22-1.99 (m, 6H), 1.90-1.77 (m, 1H), 1.59-1.44 (m, 2H). MS-ESI calculated value $[M+H]^+$ 385, measured value 385.

Embodiment 30

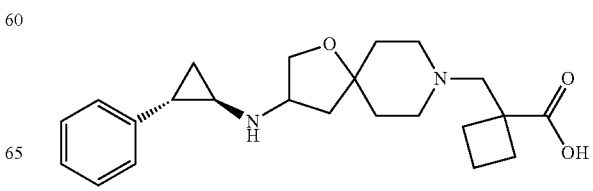

Synthetic Route:

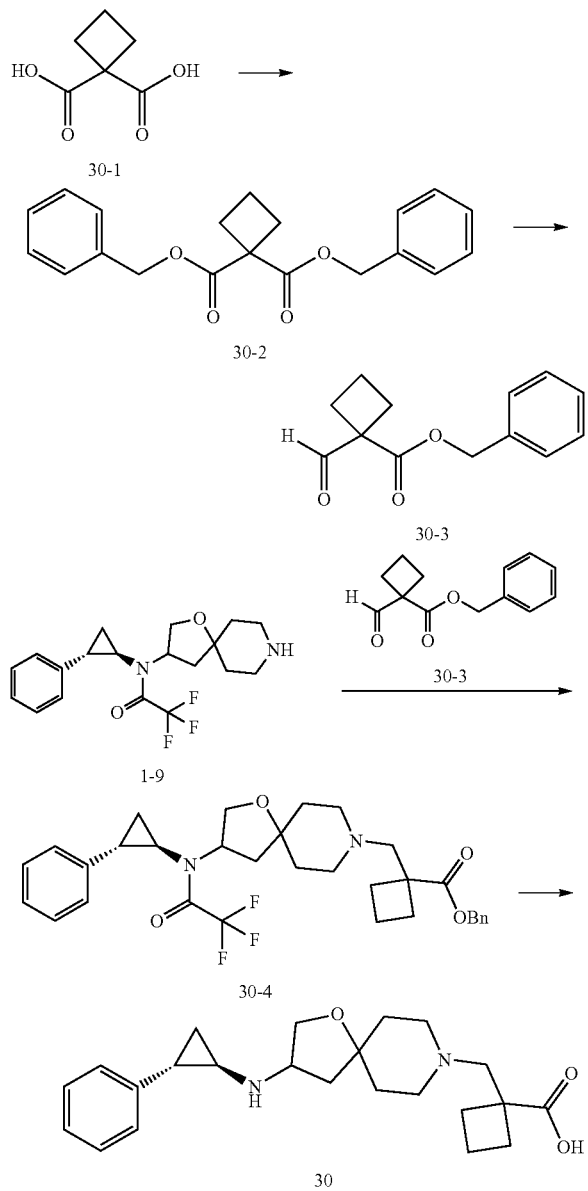

Step 1

Compound 30-1 (1.00 g, 6.94 mmol) was dissolved in anhydrous N,N-dimethylformamide (10 mL), triethylamine (2.81 g, 27.8 mmol) was added thereto at 0° C., and the mixture was stirred for 15 minutes, benzyl bromide (4.15 g, 24.3 mmol) was added thereto, and the mixture was stirred at 0° C. for 15 minutes, then heated to 25° C. and stirred for 11.5 hours. The reaction solution was quenched by adding water (50 mL) and the mixture was extracted with ethyl acetate (50 mL×3), the organic phase was washed with saturated sodium bicarbonate solution (50 mL×1) and sodium chloride solution (50 mL×1), dried over anhydrous sodium sulfate, filtered, concentrated under reduced pressure, and the residue was purified by preparative thin-layer chromatography (10:1 petroleum ether/ethyl acetate, $R_f$=0.78) to obtain compound 30-2. $^1$H NMR (400 MHz, CDCl$_3$) δ 7.36-7.28 (m, 10H), 5.18 (s, 4H), 2.63-2.59 (m, 4H), 2.07-1.98 (m, 2H).

Step 2

Compound 30-2 (6.00 g, 18.5 mmol) was dissolved in anhydrous dichloromethane (120 mL), and diisobutylaluminum hydride (1.5 M toluene solution, 24.7 mL, 36.9 mmol) was added dropwise at −78° C., the reaction mixture was stirred at −78° C. for 2 hours. The reaction was quenched by adding hydrochloric acid (1 mol/L, 36.9 mL) and water (100 mL) at −78° C., the mixture was stirred at 25° C. for 30 minutes, and extracted with ethyl acetate (100 mL×3). The organic phase was washed with saturated sodium bicarbonate (100 mL) and saturated brine (100 mL), dried over anhydrous sodium sulfate, filtered, and concentrated under reduced pressure. The crude product was purified by silica gel column chromatography (10:1 petroleum ether/ethyl acetate, $R_f$=0.5) to obtain compound 30-3. $^1$H NMR (400 MHz, CDCl$_3$) δ 9.81 (s, 1H), 7.40-7.34 (m, 5H), 5.23 (s, 2H), 2.52-2.48 (m, 4H), 2.05-1.88 (m, 2H).

Step 3

Compound 1-9 (500 mg, 1.36 mmol) and compound 30-3 (594 mg, 2.72 mmol) were dissolved in anhydrous dichloromethane (10 mL), and glacial acetic acid (245 mg, 4.08 mmol) was added to the reaction mixture. The reaction mixture was stirred at 20° C. for 10 hours, sodium triacetoxyborohydride (576 mg, 2.72 mmol) was added, and the reaction mixture was stirred at 20° C. for 2 hours. The reaction mixture was diluted with dichloromethane (50 mL), then washed with saturated sodium bicarbonate aqueous solution (50 mL×3), water (50 mL×2), and saturated brine (50 mL×1) respectively, then dried over anhydrous sodium sulfate, filtered, and the mother liquor was then concentrated and dissolved in anhydrous dichloromethane (10 mL), compound 30-3 (297 mg, 1.36 mmol) and glacial acetic acid (8.17 mg, 0.136 mmol) were added thereto, the reaction mixture was stirred at 20° C. for 10 hours, and sodium triacetoxyborohydride (577 mg, 2.72 mmol) was added, the reaction mixture was stirred at 20° C. for 2 hours. After diluting with dichloromethane (50 mL), the reaction mixture was washed with saturated aqueous solution of sodium bicarbonate (50 mL×3) and water (50 mL×2) in sequence, and washed once with saturated brine (50 mL×1), then dried over anhydrous sodium sulfate, filtered, the resulting mother liquor was concentrated, and the crude product was purified by high performance liquid chromatography (neutral, ammonium bicarbonate system) to obtain compound 30-4. $^1$H NMR (400 MHz, CDCl$_3$) δ 7.42-7.31 (m, 7H), 7.28-7.24 (m, 1H), 7.15-7.09 (m, 2H), 5.19 (d, J=6.4 Hz, 2H), 4.65-4.61 (m, 1H), 4.09-4.01 (m, 1H), 3.94-3.87 (m, 1H), 3.00-2.97 (m, 1H), 2.73-7.71 (d, J=8.4 Hz, 2H), 2.51-2.34 (m, 7H), 2.04-1.88 (m, 6H), 1.71-1.67 (m, 1H), 1.64-1.61 (m, 2H), 1.50-1.41 (m, 3H) MS-ESI calculated value [M+H]$^+$ 571, measured value 571.

Step 4

Compound 30-4 (220 mg, 0.385 mmol) was dissolved in tetrahydrofuran (2 mL), water (2 mL) and ethanol (2 mL), and sodium hydroxide (46.3 mg, 1.16 mmol) was added thereto. The reaction mixture was stirred at 60° C. for 2 hours, tetrahydrofuran and ethanol were removed by concentration under reduced pressure, the residue was dissolved in water (6 mL), and the pH value was adjusted to 4 with hydrochloric acid (1 mol/L), the mixture was concentrated under reduced pressure, the residue was purified by high performance liquid chromatography (acidic, hydrochloric acid system) to obtain the hydrochloride of compound 30. $^1$H NMR (400 MHz, CD$_3$OD) δ 7.34-7.31 (m, 2H), 7.26-7.21 (m, 3H), 4.24-4.21 (m, 1H), 4.19-4.13 (m, 2H), 3.67-3.59 (m, 2H), 3.47-3.35 (m, 2H), 3.30-3.27 (m, 1H), 3.04-3.02 (m, 1H), 2.71-2.67 (m, 1H), 2.59-2.52 (m, 2H), 2.46-2.39 (m, 1H), 2.30-2.21 (m, 3H), 2.20-1.95 (m, 6H), 1.71-1.65 (m, 2H), 1.44-1.40 (m, 1H). MS-ESI calculated value [M+H]$^+$ 385, measured value 385.

Embodiment 31

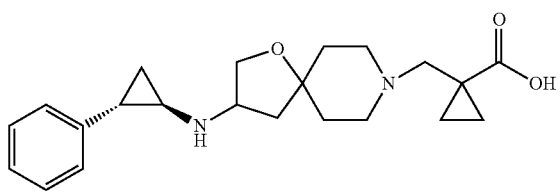 [SMILES: O=C(O)C1(CN2CCC3(CC2)CC(N[C@@H]2C[C@H]2c2ccccc2)CO3)CC1]

Synthetic Route:

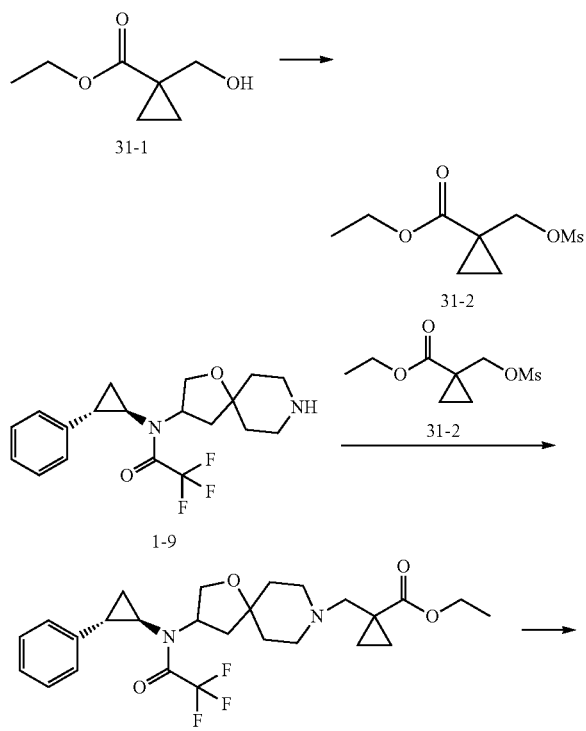

Step 1

Compound 31-1 (10.0 g, 69.4 mmol) was dissolved in anhydrous dichloromethane (100 mL), and triethylamine (20.1 g, 0.208 mol) and methanesulfonyl chloride (15.9 g, 0.139 mol) were added to the reaction mixture at 0° C. under nitrogen protection. The reaction mixture was stirred at 25° C. for 2 hours. Saturated sodium bicarbonate solution (200 mL) was added to the reaction mixture, and the mixture was extracted with ethyl acetate (100 mL×3), the organic phases were combined and dried over anhydrous sodium sulfate, filtered, and the mother liquor was concentrated to obtain compound 31-2. $^1$H NMR (400 MHz, CD$_3$OD) δ 4.27 (m, 2H), 4.12-4.09 (m, 2H), 3.02-3.01 (m, 3H), 1.38-1.36 (m, 2H), 1.21-1.18 (m, 3H), 0.99-0.96 (m, 2H).

Step 2

Compound 31-2 (181 mg, 0.814 mmol) and compound 1-9 (150 mg, 0.407 mmol) were dissolved in anhydrous dioxane (3 mL), and triethylamine (124 mg, 1.22 mmol) was added to the reaction mixture under nitrogen protection. The reaction mixture was stirred at 50° C. for 3 hours. Water (10 mL) was added to the reaction mixture, the mixture was extracted with ethyl acetate (10 mL×3), and the organic phases were combined and washed with saturated sodium chloride (20 mL×1), dried over anhydrous sodium sulfate, filtered, the filtrate was concentrated, and the crude product was purified by thin layer chromatography (2:1 petroleum ether/ethyl acetate, R$_f$=0.50) to obtain compound 31-3. $^1$H NMR (400 MHz, CD$_3$OD) δ 7.25-7.21 (m, 2H), 7.17-7.16 (m, 1H), 7.03-6.96 (m, 2H), 4.58-4.47 (m, 1H), 4.07-4.02 (m, 2H), 3.99-3.94 (m, 1H), 3.88-3.80 (m, 1H), 2.66 (s, 2H), 2.52-2.50 (m, 4H), 2.31-2.28 (m, 1H), 2.02-1.94 (m, 2H), 1.83-1.78 (m, 1H), 1.65-1.49 (m, 4H), 1.41-1.37 (m, 1H), 1.22-1.13 (m, 6H), 0.83 (m, 2H). MS-ESI calculated value [M+H]$^+$ 495, measured value 495.

Step 3

Compound 31-3 (100 mg, 0.202 mmol) was dissolved in tetrahydrofuran (1 mL), ethanol (1 mL) and water (1 mL), and sodium hydroxide (24.3 mg, 0.607 mmol) was added to the reaction mixture. The reaction mixture was stirred and reacted at 60° C. for 3 hours, the solvent was removed by concentration under reduced pressure. The residue was diluted with water and the pH value was adjusted to about 4 with aqueous hydrochloric acid solution (1 mol/L). The mixture was purified by high performance liquid chromatography (acidic, hydrochloric acid system) to obtain the hydrochloride of compound 31. $^1$H NMR (400 MHz, CD$_3$OD) δ 7.35-7.31 (m, 2H), 7.27-7.21 (m, 3H), 4.23-4.14 (m, 3H), 3.64-3.57 (m, 2H), 3.44-3.30 (m, 4H), 3.04-3.02 (m, 1H), 2.69-2.65 (m, 1H), 2.47-2.41 (m, 1H), 2.24-2.00 (m, 5H), 1.68-1.64 (m, 1H), 1.52-1.51 (m, 2H), 1.45-1.40 (m, 1H), 1.28-1.25 (m, 2H). MS-ESI calculated value [M+H]$^+$ 371, measured value 371.

Embodiment 32

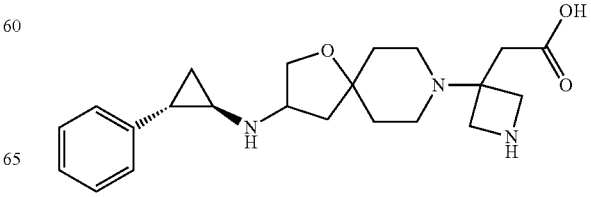

Synthetic Route:

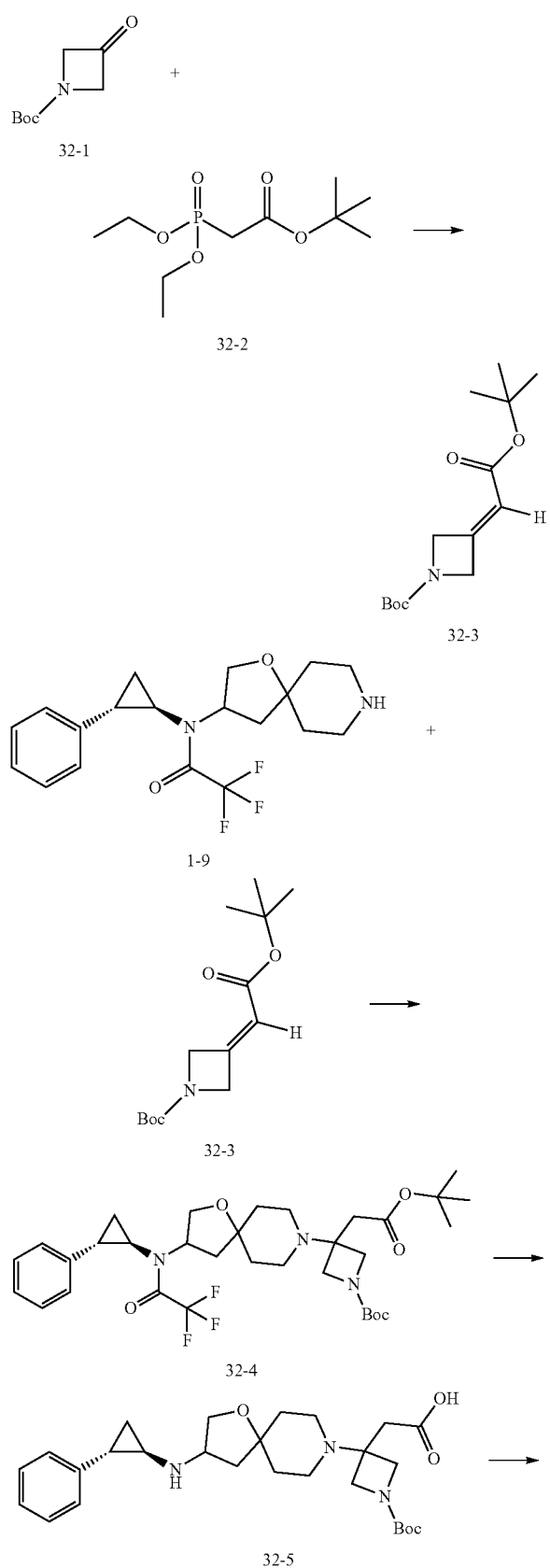

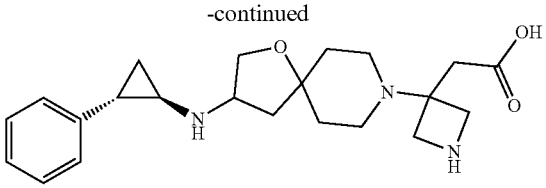

Step 1

Compound 32-2 (1.92 g, 7.59 mmol) was dissolved in anhydrous tetrahydrofuran (20 mL), and potassium tert-butoxide (852 mg, 7.59 mmol) was added to the reaction mixture at 0° C. under nitrogen protection. The reaction mixture was stirred at 25° C. for 0.5 hour. Then a solution of compound 32-1 (1 g, 5.84 mmol) in tetrahydrofuran (20 mL) was added to the mixture at 0° C. under nitrogen protection. The reaction mixture was stirred at 25° C. for 11.5 hours. Water (100 mL) was added to the reaction mixture, and the mixture was extracted with ethyl acetate (100 mL×3), the organic phases were combined, washed with saturated sodium chloride aqueous solution (100 mL×1), dried over anhydrous sodium sulfate, filtered, the filtrate was concentrated, and the crude product was purified by column chromatography (5:1 petroleum ether/ethyl acetate, $R_f$=0.80) to obtain compound 32-3. $^1$H NMR (400 MHz, CD$_3$OD) δ 5.77-5.68 (m, 1H), 4.83-4.80 (m, 2H), 4.60-4.58 (m, 2H), 1.49 (s, 9H), 1.47 (s, 9H).

Step 2

Compound 32-3 (450 mg, 1.67 mmol) and compound 1-9 (513 mg, 1.39 mmol) were dissolved in acetonitrile (20 mL), and 1,8-diazabicyclo[5.4.0]undec-7-ene (106 mg, 0.696 mmol). The reaction mixture was stirred at 65° C. for 12 hours. Water (80 mL) was added to the reaction mixture and extracted with ethyl acetate (80 mL×3), the organic phases were combined and washed with saturated aqueous solution of sodium chloride (80 mL×1), dried over anhydrous sodium sulfate, filtered, the mother liquor was concentrated, and the crude product was purified by column chromatography (2:1 petroleum ether/ethyl acetate, $R_f$=0.20) to obtain compound 32-4. $^1$H NMR (400 MHz, CD$_3$OD) δ 7.35-7.31 (m, 2H), 7.28-7.24 (m, 1H), 7.09-7.07 (m, 2H), 4.66-4.62 (m, 1H), 3.96-3.92 (m, 3H), 3.80-3.76 (m, 2H), 2.57-2.50 (m, 4H), 2.40-2.34 (m, 3H), 2.07-2.04 (m, 3H), 1.85-1.83 (m, 1H), 1.76-1.74 (m, 3H), 1.51-1.44 (m, 21H). MS-ESI calculated values [M+H]$^+$ 638, measured values 638.

Step 3

Compound 32-4 (420 mg, 0.659 mmol) was dissolved in tetrahydrofuran (4 mL), ethanol (4 mL) and water (4 mL), and sodium hydroxide (79.0 mg, 1.98 mmol) was added to the reaction mixture. The reaction mixture was stirred at 60° C. for 3 hours, and then concentrated under reduced pressure to remove the solvent, the residue was diluted with water, and the pH value was adjusted to about 3 with aqueous solution of hydrochloric acid (1 mol/L). The mixture was extracted with ethyl acetate (20 mL×3), dried over anhydrous sodium sulfate, filtered, and the mother liquor was concentrated to obtain compound 32-5. MS-ESI calculated value [M+H]$^+$ 486, measured value 486.

Step 4

Compound 32-5 (280 mg, 0.577 mmol) was dissolved in ethyl acetate (2 mL), and a solution of hydrochloric acid in ethyl acetate (4M, 2.88 mL) was added to the reaction mixture. The reaction mixture was stirred at 30° C. for 3 hours, then concentrated under reduced pressure to remove the solvent. The residue was purified by high performance liquid chromatography (hydrochloric acid system) to obtain the hydrochloride of compound 32. $^1$H NMR (400 MHz, CD$_3$OD) δ 7.37-7.33 (m, 2H), 7.29-7.26 (m, 1H), 7.18-7.16 (m, 2H), 4.68-4.67 (m, 1H), 4.47-4.41 (m, 3H), 4.22-4.10 (m, 3H), 3.17-3.06 (m, 6H), 2.94-2.93 (m, 1H), 2.52-2.43 (m, 2H), 2.05-1.89 (m, 5H), 1.51-1.50 (m, 1H), 1.45-1.40 (m, 1H). MS-ESI calculated value [M+H]$^+$ 386, measured value 386.

Embodiment 33

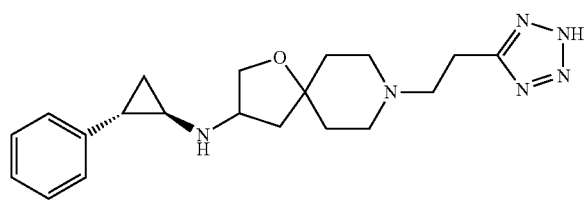 [SMILES: c1ccc([C@@H]2C[C@H]2NC2COC3(CCN(CCc4nn[nH]n4)CC3)C2)cc1]

Synthetic Route:

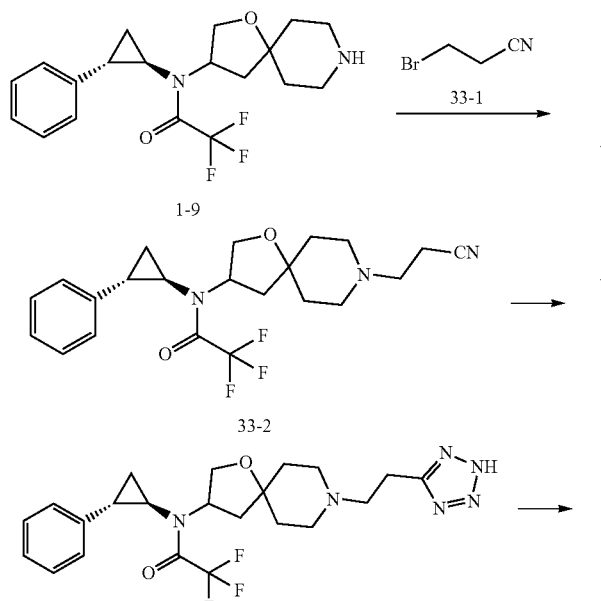

33

Step 1

Compound 1-9 (300 mg, 0.622 mmol), compound 33-1 (125 mg, 0.933 mmol) and triethylamine (189 mg, 1.87 mmol) were dissolved in acetonitrile (5 mL). The reaction mixture was stirred at 50° C. for 10 hours, concentrated under reduced pressure to remove the solvent, and the residue was dissolved with dichloromethane (50 mL). The organic phase was washed with water (50 mL×1) and saturated brine (50 mL×1) in sequence, and dried over anhydrous sodium sulfate, filtered, the mother liquor was concentrated, and the crude product was purified by thin-layer chromatography (1:2 petroleum ether/ethyl acetate, R$_f$=0.24) to obtain compound 33-2. MS-ESI calculated value [M+H]$^+$ 422, measured value 422.

Step 2

Compound 33-2 (100 mg, 0.237 mmol) was dissolved in dioxane (3 mL), trimethylsilyl azide (109 mg, 0.949 mmol) and dibutyltin oxide (17.7 mg, 71.2 μmol)) were added to the reaction mixture, the reaction mixture was stirred at 120° C. for 10 hours. Water (10 mL) was added at room temperature, and then the mixture was extracted with ethyl acetate (10 mL×3), the organic phases were combined and washed with saturated sodium chloride solution (20 mL×1), the organic phase was dried over anhydrous sodium sulfate, filtered, and the filtrate was concentrated under reduced pressure to obtain a crude product of compound 33-3. MS-ESI calculated value [M+H]$^+$ 465, measured value 465.

Step 3

Compound 33-3 (215 mg, 0.401 mmol) was dissolved in tetrahydrofuran (2 mL) and absolute ethanol (2 mL), sodium hydroxide (80.3 mg, 2.01 mmol) was dissolved in water (2 mL) and added dropwise to the solution, and the solution was stirred at 50° C. for 2 hours. The reaction mixture was concentrated under reduced pressure to remove the solvent, the pH value was adjusted to 5 with hydrochloric acid (1 mol/L) and concentrated under reduced pressure. The crude product was purified by high performance liquid chromatography (acidic, hydrochloric acid system) to obtain the hydrochloride of compound 33. $^1$H NMR (400 MHz, CD$_3$OD) δ 7.33-7.28 (m, 2H), 7.25-7.19 (m, 3H), 4.24-4.16 (m, 3H), 3.66-3.52 (m, 6H), 3.02-3.30 (m, 2H), 3.01-3.00 (m, 1H), 2.70-2.55 (m, 1H), 2.49-2.35 (m, 1H), 2.78-2.06 (m, 4H), 2.05-1.93 (m, 1H), 1.71-1.56 (m, 1H), 1.47-1.37 (m, 1H). MS-ESI calculated value [M+H]$^+$ 369, measured value 369.

Embodiment 34

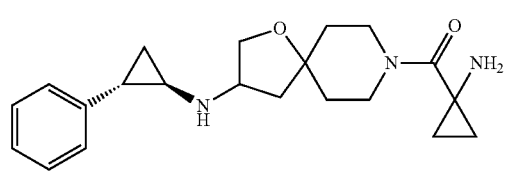 [SMILES: NC1(C(=O)N2CCC3(CC2)CC(N[C@@H]2C[C@H]2c2ccccc2)CO3)CC1]

Synthetic Route:

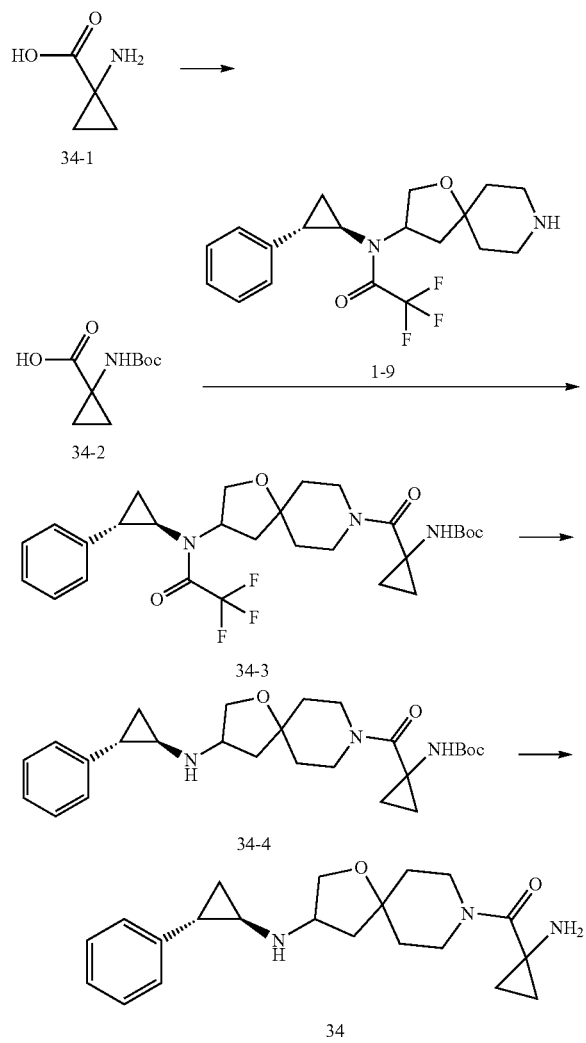

Step 1

Lithium hydroxide monohydrate (830 mg, 19.8 mmol) was dissolved in water (3 mL), di-tert-butyl dicarbonate (2.37 g, 10.9 mmol) was added to a solution of compound 34-1 (1.00 g, 9.89 mmol) in tetrahydrofuran (12 mL), the reaction mixture was stirred at 15° C. for 12 hours. The pH value was adjusted to 6 with hydrochloric acid (1 N) aqueous solution, then diluted with water (15 mL), and extracted with ethyl acetate (15 mL×3), the mixture was then washed with saturated brine (30 mL×1), dried over anhydrous sodium sulfate, filtered, and the mother liquor was concentrated to obtain a crude product of compound 34-2. $^1$H NMR (400 MHz, CDCl$_3$) δ 9.56 (brs, 1H), 1.60-1.57 (m, 2H), 1.45 (s, 9H), 1.27-1.21 (m, 2H). MS-ESI calculated values [M+Na]$^+$ 224, measured values 224.

Step 2

Compound 34-3 was obtained by referring to Step 1 of Embodiment 22. $^1$H NMR (400 MHz, CDCl$_3$) δ 7.34-7.23 (m, 3H), 7.07-7.06 (m, 2H), 5.23-5.07 (m, 1H), 4.70-4.58 (m, 1H), 4.08-3.97 (m, 3H), 3.49-3.41 (m, 2H), 3.11-2.89 (m, 1H), 2.43-2.32 (m, 1H), 2.16-2.07 (m, 2H), 1.71-1.59 (m, 6H), 1.49-1.41 (m, 12H), 1.16-0.98 (m, 1H). MS-ESI calculated value [M+H]$^+$ 552, measured value 552.

Step 3

Compound 34-4 was obtained by referring to Step 2 of Embodiment 6. MS-ESI calculated value [M+H]$^+$ 456, measured value 456.

Step 4

The hydrochloride of the compound 34 was obtained by referring to Step 4 of Embodiment 32. $^1$H NMR (400 MHz, CD$_3$OD) δ 7.33-7.29 (m, 2H), 7.24-7.18 (m, 3H), 4.18-3.93 (m, 5H), 3.48-3.39 (m, 2H), 3.28-3.21 (m, 1H), 3.02-3.00 (m, 1H), 2.65-2.56 (m, 1H), 2.47-2.37 (m, 1H), 2.05-1.92 (m, 4H), 1.66-1.53 (m, 2H), 1.39-1.30 (m, 4H). MS-ESI calculated values [M+H]$^+$ 356, measured values 356.

Biochemical Test: In Vitro Evaluation

Experiment 1: Evaluation of Enzyme Activity

The purpose of this test was to detect the in vitro inhibitory activity of the compounds against LSD1. The enzyme used in this test was human LSD1, the standard substrate was histone H3K4me peptide (20 μM), the fluorescence coupling enzyme method was used to determine the activity of the compound by combining horseradish peroxidase (HRP) and fluorescent reagent Amplex Red to detect the H$_2$O$_2$ generation as a result of the reaction of LSD1. Compounds were tested in 10-dose IC50 mode with a 3-fold serial dilution starting at 10 μM. The enzyme and the substrate were co-incubated for 30 minutes before adding the compounds to the substrate to start the reaction. Fluorescence detector: Envision, excitation wavelength: Ex/Em=530/590 nM Testing the inhibitory activity of the compounds against LSD1, and the results are shown in Table 1.

TABLE 1

In vitro enzyme activity screening test results of the compounds of the present disclosure

| Number of the compound | IC$_{50}$ (nM) |
| --- | --- |
| Hydrochloride of the compound 1 | 1689 |
| Hydrochloride of the compound 2 | 1578 |
| Hydrochloride of the compound 3 | 96.66 |
| Hydrochloride of the compound 4 | 939.7 |
| Hydrochloride of the compound 5 | 3854 |
| Hydrochloride of the compound 6 | 328.8 |
| Hydrochloride of the compound 7 | 45.07 |
| Hydrochloride of the compound 8 | 39.73 |
| Hydrochloride of the compound 9 | 37.76 |
| Hydrochloride of the compound 10 | 78.44 |
| Hydrochloride of the compound 11 | 2879 |

TABLE 1-continued

In vitro enzyme activity screening test results
of the compounds of the present disclosure

| Number of the compound | $IC_{50}$ (nM) |
|---|---|
| Hydrochloride of the compound 12 | 1377 |
| Hydrochloride of the compound 13 | 46.59 |
| Hydrochloride of the compound 14 | 117.7 |
| Hydrochloride of the compound 15 | 352.8 |
| Hydrochloride of the compound 16 | 261.8 |
| Hydrochloride of the compound 17 | 70.63 |
| Hydrochloride of the compound 18 | 92.88 |
| Hydrochloride of the compound 19 | 208.3 |
| Hydrochloride of the compound 20 | 241.7 |
| Hydrochloride of the compound 21 | 92.19 |
| Hydrochloride of the compound 22 | 908.2 |
| Hydrochloride of the compound 23 | 64.62 |
| Hydrochloride of the compound 24 | 41.51 |
| Hydrochloride of the compound 25 | 1723 |
| Hydrochloride of the compound 26 | 271.4 |
| Hydrochloride of the compound 27 | 1776 |
| Hydrochloride of the compound 28 | 1456 |
| Hydrochloride of the compound 29 | 1672 |
| Hydrochloride of the compound 30 | 1137 |
| Hydrochloride of the compound 31 | 2123 |
| Hydrochloride of the compound 32 | 1162 |
| Hydrochloride of the compound 33 | 48.24 |
| Hydrochloride of the compound 34 | 38.4 |

Conclusion: the compounds of the present disclosure have obvious inhibitory activity against LSD1.

Experimental Example 2: Evaluation of Antiproliferation Activity of NCI-111417 Cells Experimental purpose: to detect the antiproliferation activity of the compounds on NCI-H1417 cells.

Experimental materials: RPMI 1640 culture medium, fetal bovine serum, Promega CellTiter-Glo reagent. NCI-H1417 cell line purchased from ATCC. Envision multi-label reader (PerkinElmer).

Experimental method: the compounds were dissolved to 10 mM, then the compounds were diluted 5 times with DMSO in a compound plate, the compounds were diluted 3-fold with Bravo from a starting concentration of 2 mM to the 10th concentration, 250 nL of the solutions were transferred to the upper and lower duplicate wells on a blank 384 cell plate by Echo transfer plate, cell suspension of per well/1000 cells/50 μL was added to the transferred 250 nL DMSO/compound, the compounds were diluted 200-fold, i.e., the initial action concentration was 10 μM. The cell plate was placed in a carbon dioxide incubator and incubated for 10 days. 25 μL of Promega CellTiter-Glo reagent was added to each well on the cell plate and was shaken at room temperature for 10 minutes to stabilize the luminescence signal. Readings were performed by PerkinElmer Envision multi-label analyzer.

Data analysis: the equation (Max-Ratio)/(Max-Min)*100% was used to convert the original data into the inhibition rate, the value of $IC_{50}$ can be obtained by curve fitting of four-parameters (the 205 mode in XLFITS, iDBS).

Testing the antiproliferation activity of the compounds against NCI-H1417 cells, and the results are shown in Table 2.

TABLE 2 test results of the antiproliferation activity of the compounds
of the present disclosureon NCI-H1417 cells:

| Number of the compound | $IC_{50}$ (nM) |
|---|---|
| Hydrochloride of the compound 6 | 9.11 |
| Hydrochloride of the compound 15 | 13.10 |
| Hydrochloride of the compound 16 | 12.10 |
| Hydrochloride of the compound 17 | 0.65 |
| Hydrochloride of the compound 19 | 6.95 |
| Hydrochloride of the compound 20 | 3.99 |
| Hydrochloride of the compound 21 | 1.12 |
| Hydrochloride of the compound 23 | 1.68 |
| Hydrochloride of the compound 30 | 91.36 |
| Hydrochloride of the compound 32 | 3.97 |
| Hydrochloride of the compound 34 | 4.38 |

Conclusion: The compounds of the present disclosure have obvious antiproliferation activity on NCI-H1417 cells.

Experimental Example 3: Evaluation of Antiproliferation Activity on HL60 Cells

Experimental purpose: to detect the antiproliferation activity of the compound to be tested on HL60 cells.

Experimental materials: RPMI-1640 culture medium, fetal bovine serum, penicillin/streptomycin antibiotics purchased from Wisent. CellTiter-Glo (chemiluminescent cell viability assay reagent) reagents purchased from Promega. HL60 cell line purchased from Nanjing Cobioer Co., Ltd. Nivo multi-label reader (PerkinElmer).

Experimental method: HL60 cells were planted in a white 384-well plate, 40 μL of cell suspension per well, 600 HL60 cells were contained therein. The cell plate was placed in a carbon dioxide incubator for overnight culture. The compounds to be tested were diluted 5-fold with a pipet until the 10th concentration, i.e., diluted from 2 mM to 1.024 nM, double duplicate well experiment was set. 78 μL of the culture medium was added to an intermediate plate, and then 2 μL per well of the serially diluted compounds were transferred to the corresponding positions on the intermediate plate, after mixing, 10 μL per well was transferred to the cell plate. The cell plate was incubated in a carbon dioxide incubator for 6 days. Another cell plate was prepared and the signal value on the day of dosing was read as the maximum value (Max value in the equation below) to participate in the data analysis. 20 μL of chemiluminescent cell viability assay reagent was added to each well of this cell plate, which was incubated at room temperature for 10 minutes to stabilize the luminescence signal. The multi-label reader was used for reading.

Data analysis: the equation (Sample-Min)/(Max-Min) *100% was used to convert the original data into the inhibition rate, the $IC_{50}$ value can be obtained by curve fitting of four-parameters ("log(inhibitor) vs. response—Variable slope" mode in GraphPad Prism)).

The antiproliferation activity of the compounds on HL60 cells were tested, and the results are shown in Table 3.

TABLE 3

Test results of antiproliferation activity of the compounds of the present disclosure on HL60 cells

| Number of the compound | $IC_{50}$ (nM) |
|---|---|
| Hydrochloride of the compound 6 | 14.74 |
| Hydrochloride of the compound 15 | 13.8 |
| Hydrochloride of the compound 16 | 8.46 |
| Hydrochloride of the compound 17 | 0.78 |
| Hydrochloride of the compound 18 | 20.44 |
| Hydrochloride of the compound 19 | 1.46 |
| Hydrochloride of the compound 20 | 8.99 |
| Hydrochloride of the compound 21 | 1.17 |
| Hydrochloride of the compound 24 | 39.1 |
| Hydrochloride of the compound 30 | 337.2 |
| Hydrochloride of the compound 32 | 0.55 |
| Hydrochloride of the compound 34 | 1.92 |

Conclusion: The compounds of the present disclosure have obvious antiproliferation activity on HL60 cells.

Experimental Example 4: Evaluation of Inhibitory Activity Against Proliferation of MV-4-11 Cells Experimental purpose: to detect the antiproliferation activity of the compound to be tested on MV-4-11 cells.

Experimental materials: IMDM culture medium, fetal bovine serum, penicillin/streptomycin antibiotics purchased from Wisent. CellTiter-Glo (chemiluminescent cell viability assay reagent) reagents purchased from Promega. MV-4-11 cell line was purchased from Nanjing Cobioer Co., Ltd. Nivo Multi-Marker Analyzer (PerkinElmer).

Experimental method: MV-4-11 cells were planted in a white 96-well plate, 80 μL of cell suspension per well, which contained 6000 MV-4-11 cells. The cell plate was placed in a carbon dioxide incubator for overnight culture.

The compounds to be tested were diluted 5-fold with a pipet until the 8th concentration, i.e., diluted from 2 mM to 25.6 nM, double duplicate well experiment was set. 78 μL of the culture medium was added to an intermediate plate, and then 2 μL per well of the serially diluted compounds were transferred to the corresponding positions on the intermediate plate, after mixing, 20 μL per well was transferred to the cell plate. The cell plate was incubated in a carbon dioxide incubator for 6 days. Another cell plate was prepared and the signal value on the day of dosing was read as the maximum value (Max value in the equation below) to participate in the data analysis. 25 μL of the chemiluminescent cell viability assay reagent was added to each well of this cell plate, which was incubated at room temperature for 10 minutes to stabilize the luminescence signal. The multi-label analyzer was used for reading.

Data analysis: the equation (Sample-Min)/(Max-Min) *100% was used to convert the original data into the inhibition rate, the $IC_{50}$ value can be obtained by curve fitting of four-parameters ("log(inhibitor) vs. response—Variable slope" mode in GraphPad Prism)).

The antiproliferation activity of the compounds on MV-4-11 cells were tested, and the results are shown in Table 4.

TABLE 4

Test results of antiproliferation activity of the compounds of the present disclosure on MV-4-11 cells.

| Number of the compound | $IC_{50}$ (nM) |
|---|---|
| Hydrochloride of the compound 6 | 3.21 |
| Hydrochloride of the compound 15 | 13.16 |
| Hydrochloride of the compound 16 | 13.70 |
| Hydrochloride of the compound 17 | 2.86 |
| Hydrochloride of the compound 18 | 16.03 |
| Hydrochloride of the compound 19 | 4.41 |
| Hydrochloride of the compound 20 | 9.56 |
| Hydrochloride of the compound 21 | 0.46 |
| Hydrochloride of the compound 24 | 38.32 |
| Hydrochloride of the compound 30 | 33.15 |
| Hydrochloride of the compound 32 | 1.9 |
| Hydrochloride of the compound 34 | 1.37 |

Conclusion: the compounds of the present disclosure have obvious antiproliferation activity on MV-4-11 cells.

Experimental Example 5: Pharmacokinetic Evaluation of the Compounds

Experimental Purpose: To Test the In Vivo Pharmacokinetics of the Compounds in CD-1 Mice Experimental Materials CD-1 mice (male, 7-9 weeks old, Shanghai Slac)

Experimental Operation

The rodent pharmacokinetic characteristics after intravenous injection and oral administration of the compounds were tested by standard protocols, in the experiment, the candidate compounds were formulated into clear solutions and administrated to mice via a single intravenous injection and oral administration. The vehicle for intravenous injection and oral administration was a mixed solution of 10% of dimethyl sulfoxide and 90% of 10% hydroxypropyl β cyclodextrin. This project used four male CD-1 mice, two mice were administered intravenously, with a dose of 1 mg/kg, and plasma samples were collected at 0 hour (before administration) and 0.0833, 0.25, 0.5, 1, 2, 4, 8, 24 hours after administration. The other two mice were orally administered by gavage, with a dose of 2 mg/kg, plasma samples were collected at 0 hour (before administration) and 0.25, 0.5, 1, 2, 4, 8, 24 hours after administration, whole blood samples were collected within 24 hours, which were centrifuged at 3000 g for 15 minutes, and the supernatants were separated to obtain plasma samples, 4 times volume of acetonitrile solutions containing internal standard were added to precipitate the protein, the mixtures were centrifuged to obtain the supernatants, the supernatants were added with water of equal volume and centrifuged again to take the supernatant for injection, and the blood drug concentration was quantitatively analyzed by the LC-MS/MS analysis method, and pharmacokinetic parameters were calculated, such as max concentration (Cmax), clearance (CL), half-life ($T_{1/2}$), volumes of distribution (Vdss), the area under the plasma concentration-time curve ($AUC_{0\text{-}last}$), bioavailability (F) etc.

The experimental results are shown in Table 5:

TABLE 5

Pharmacokinetic test results

| Compound | Max concentration $C_{max}$ (nM) | Clearance CL (mL/min/kg) | Volumes of distribution Vdss (L/kg) | Half-life $T_{1/2}$ (IV, h) | The area under the plasma concentration-time curve $AUC_{0\text{-}last}$ PO (nM · hr) | Bioavailability F (%) |
|---|---|---|---|---|---|---|
| Hydrochloride of the compound 6 | 718 | 40.2 | 1.19 | 1.54 | 691 | 33.2 |
| Hydrochloride of the compound 14 | 629 | 16.9 | 0.551 | 0.874 | 1376 | 28.7 |
| Hydrochloride of the compound 15 | 919 | 41.8 | 0.835 | 0.49 | 765 | 39.1 |
| Hydrochloride of the compound 16 | 860 | 33.8 | 0.88 | 0.579 | 891 | 36.9 |
| Hydrochloride of the compound 20 | 714 | 19.7 | 0.752 | 0.905 | 1342 | 29 |
| Hydrochloride of the compound 23 | 144 | 68.7 | 18.6 | 4.32 | 360 | 37.2 |
| Hydrochloride of the compound 34 | 1150 | 25.3 | 2.09 | 1.39 | 2141 | 58.3 |

Conclusion: The compounds of the present disclosure have good pharmacokinetic properties, including good oral bioavailability, oral exposure, half-life and clearance, etc.

Experimental Example 6: Inhibition Test for hERG Potassium Ion Channel

Experimental purpose: to detect the effect of the embodiments to be tested on the potassium ion channel of hERG by using the fully automatic patch-clamp method.

Experimental Method

6.1. Cell Culture 6.1.1 CHO-hERG cells were cultured in a 175 cm² culture flask, after the cell density was increased to 60-80%, the culture medium was removed, the cells were washed once with 7 mL PBS (Phosphate Buffered Saline), and then 3 mL digestive fluid was added for digestion.

6.1.2 After the digestion was complete, 7 mL of culture medium was added for neutralization, then the mixture was centrifuged, the supernatant was aspirated, and then 5 mL of culture medium was added for resuspention to ensure that the cell density was 2-5×10⁶/mL.

6.2 Solution Preparation

TABLE 6.1

Composition of intracellular fluid and extracellular fluid

| Reagent | Extracellular fluid (mM) | Intracellular fluid (mM) |
|---|---|---|
| $CaCl_2$ | 2 | 5.374 |
| $MgCl_2$ | 1 | 1.75 |
| KCl | 4 | 120 |
| NaCl | 145 | — |
| Glucose | 10 | — |
| 4-(2-Hydroxyethyl)piperazine-1-ethanesulfonic acid | 10 | 10 |

TABLE 6.1-continued

Composition of intracellular fluid and extracellular fluid

| Reagent | Extracellular fluid (mM) | Intracellular fluid (mM) |
|---|---|---|
| Ethylene glycol bis(2-aminoethyl ether) tetraacetic acid | — | 5 |
| $Na_2ATP$ | — | 4 |
| pH | the pH value was adjusted to 7.4 with NaOH | the pH value was adjusted to 7.4 with KOH |

Note:
"—" means no such reagent.

6.3 Electrophysiological Recording Process

The single-cell high-impedance sealing and the whole-cell mode formation process were all automatically completed by the Qpatch instrument of the Shanghai Institute of Materia Medica, Chinese Academy of Sciences. After the whole-cell recording mode was obtained, the cells were clamped at −80 millivolts. The cells first underwent a pre-voltage of −50 millivolts for 50 milliseconds, then underwent depolarization stimulation at +40 millivolts for 5 seconds, then underwent repolarization at −50 millivolts for 5 seconds, and then the voltage returned to −80 millivolts. This voltage stimulation was applied every 15 seconds. The data were recorded for 2 minutes, then extracellular fluid was administrated, and then the data were recorded for 5 minutes. Then, the administration process begun. The concentration of the test compound started from the lowest concentration, each test concentration was administered for 2.5 minutes. After all the concentrations were administered continuously, 3 μM of Cisapride was administrated as the positive control compound. At least three cells (n≥3) were tested at each concentration.

6.4 Compound Preparation 6.4.1 20 mM Compound mother liquor was diluted with extracellular fluid, 5 μL of 20 mM compound mother liquor was added with 2495 μL of extracellular fluid to undergo 500-fold dilution to 40 μM. Then the solution was subjected to a 3-fold serial dilution with extracellular fluid containing 0.2% DMSO to obtain a required final concentration.

6.4.2 The highest test concentration was 40 μM, the concentrations were 40, 13.33, 4.44, 1.48, 0.49, 0.16 μM respectively, a total of 6 concentrations.

6.5 Data Analysis

The experimental data were analyzed by XLFit software.

6.6 Test Results

The hERG $IC_{50}$ results of the embodiment compound are shown in Table 6.2.

TABLE 6.2 hERG $IC_{50}$ value of the embodiment compound

| Test sample | hERG $IC_{50}$ (μM) | Number of testing |
|---|---|---|
| Hydrochloride of the compound 6 | >40 | N = 2 |

Conclusion: the compounds of the present disclosure have no inhibitory effect on hERG potassium ion channels.

Experimental Example 7: In Vivo Pharmacodynamic Study of the Compounds of the Present Disclosure on MC38 Mouse Colon Cancer Transplanted Tumor Model

7.1 Experiment Purpose

The purpose of this experiment was to evaluate the in vivo efficacy of the compounds of the present disclosure on MC38 mouse colon cancer transplanted tumor model.

7.2 Experimental Animals

Species: Mice
Line: $C_{57}BL/6$ mice
Week age and weight: 7 weeks old, weighing 18-23 grams
Gender: female
Supplier: Shanghai Slack Laboratory Animal Co., Ltd.

7.3 Experimental Methods and Procedures

7.3.1 Cell Culture

Name: MC38 (Mouse Colon Cancer Cell)
Source: Obio Biotechnology (Shanghai) Co., Ltd. The conservation of species and the maintenance of passage were performed by HD Biosciences (Shanghai) Co., Ltd.

Cell culture: 1640 medium containing 10% fetal bovine serum was used as culture medium, and the culture condition was 37° C., 5% carbon dioxide. The passage ratio was 1:2 to 1:3, the passage was performed 2-3 times per week.

7.3.2 Tumor Cell Inoculation 0.1 mL ($2\times10^5$ cells) of cells were subcutaneously inoculated into the right back of each mouse. On the same day, the animals were randomly grouped according to their body weight.

7.3.3 Preparation of Test Compounds

The vehicle used in the experiment was 0.5% methyl cellulose solution, the preparation method was: 5 g methyl cellulose was weighed and dissolved in 800 mL ultrapure water, stirred evenly and made up to 1000 mL with ultrapure water. The test substances were dissolved in solvent and prepared into a uniform solution with a certain concentration, and stored at 4° C.

7.3.4 Tumor Measurement and Experimental Indicators

The experimental indicator is to investigate whether the tumor growth was inhibited, delayed or cured. Tumor diameters were measured with a vernier caliper twice a week. The tumor volume was calculated by the formula: $V=0.5 a \times b^2$, a and b respectively represent the long and short diameters of the tumor.

The efficacy of the compound was evaluated by relative tumor growth rate T/C (%). Relative tumor growth rate T/C (%): the calculation formula was as follows: T/C %=$T_{RTV}$/$C_{RTV}\times100\%$ ($T_{RTV}$: therapy group RTV; $C_{RTV}$: Negative control group RTV). The relative tumor volume (RTV) was calculated based on the results of tumor measurement, the calculation formula was: RTV=$V_t/V_0$, wherein $V_0$ was the average tumor volume measured at the time of grouping administration (i.e., d0), $V_t$ is the average tumor volume measured at a single time, $T_{RTV}$ and $C_{RTV}$ were calculated from the data on the same day.

7.4 Experimental Result

TABLE 7

Evaluation of anti-tumor efficacy of the test compounds on MC38 mouse colon cancer transplanted tumor model (Based on the calculation of tumor volume on the 28th day after administration)

| Group | Tumor volume (mm³) ($28^{th}$ day) | T/C (%) |
|---|---|---|
| Vehicle (0.5% methylcellulose solution) | 1759 ± 978 | / |
| Hydrochloride of the compound 6 (1.5 mg/kg, oral administration once a day) | 1653 ± 893 | 92 |
| PD-1 monoclonal antibody (5 mg/kg, intraperitoneal injection twice a week) | 1022 ± 925 | 58 |

TABLE 7-continued

Evaluation of anti-tumor efficacy of the test compounds on MC38 mouse colon cancer transplanted tumor model (Based on the calculation of tumor volume on the 28th day after administration)

| Group | Tumor volume (mm³) (28th day) | T/C (%) |
|---|---|---|
| PD-1 monoclonal antibody + hydrochloride of the compound 6 (5 mg/kg, intraperitoneal injection twice a week + 1.5 mg/kg, oral administration once a day) | 211 ± 269 | 12 |

Note:
PD-1 monoclonal antibody source: BioXcell. PD-1 monoclonal antibodies were administrated from the 7th day after grouping, and compound 6 was administered from the day of grouping.
Conclusion: The combination of the compound of the present disclosure and PD-1 monoclonal antibody has an excellent anti-tumor effect on MC38 mouse colon cancer transplantated tumor model.

Embodiment 8: In Vivo Pharmacodynamic Study of the Compounds of the Present Disclosure on Human Small Cell Lung Cancer NCI-111417 Cell Subcutaneous Xenograft Tumor in CB-17 SCID Mouse Model

8.1 Experimental Purpose

The purpose of the experiment was to evaluate the in vivo efficacy of the compounds of the present disclosure on subcutaneous xenograft tumor of human small cell lung cancer NCI-H1417 cells in a CB-17 SCID mouse model.

8.2 Experimental Animals

Species: Mice
Line: CB-17 SCID mice
Week age and weight: 6-8 weeks old, weighing 16-21 grams
Gender: female
Supplier: Shanghai Lingchang Biotech Co., Ltd.

8.3 Experimental Methods and Procedures 8.3.1 Cell Culture

Human small cell lung cancer NCI-H1417 cells (ATCC) were cultured in vitro in a single layer, the culture conditions were RPMI-1640 culture medium supplemented with 10% fetal bovine serum, 37° C. 5% $CO_2$. When the cell saturation reached 80%-90%, the cells were collected, counted, and inoculated.

8.3.2 Tumor Cell Inoculation 0.2 mL of $10 \times 10^6$ NCI-H1417 cells were subcutaneously inoculated into the right back of each mouse (PBS: Matrigel=1:1). Group administration was started when the average volume reached 100-150 mm³.

8.3.3 Preparation of Test Compounds

The vehicle used in the experiment was 0.5% methylcellulose solution, the preparation method was: 5 g of methylcellulose was weighed and dissolved in 800 mL ultrapure water, stirred evenly and made up to 1000 mL with ultrapure water. The test substance was dissolved in a solvent and prepared into a uniform solution of a certain concentration, and stored at 4° C.

Cisplatin (Cisplatin, manufacturer Qilu Pharmaceutical Co., Ltd., 10 mg/bottle freeze-dried powder for injection, lot number 7D011A8) was added to 10 mL 0.9% NaCl to make a 1 mg/mL mother liquor, and stored at room temperature and protected from light. The mother liquor was aliquoted into 0.63 mL and stored at room temperature. 5.67 mL 0.9% NaCl was added to one of the 0.63 mL mother liquor to make a 0.1 mg/mL solution.

8.3.4 Tumor Measurement and Experimental Indicators

The experimental indicator is to investigate whether tumor growth was inhibited, delayed, or cured. Tumor diameters were measured with a vernier caliper twice a week. The tumor volume was calculated by the calculation formula: $V=0.5 \times a \times b^2$, a and b respectively represent the long and short diameters of the tumor.

The anti-tumor effect of the compounds was evaluated by TGI (%). TGI (%) can reflect the tumor growth inhibition rate. TGI (%) calculation: TGI (%)=[1-(the average tumor volume at the end of the administration in a treatment group—the average tumor volume at the beginning of the administration in the treatment group)/(the average tumor volume at the end of the treatment of the solvent control group—the average tumor volume at the beginning of the treatment of the solvent control group)]×100%.

8.4 Experimental Results

TABLE 8

Evaluation of anti-tumor effect of the compound on human small cell lung cancer NCI-H1417 xenograft tumor model (Based on the calculation of tumor volume on the 28th day after administration)

| Group | Tumor volume mean ± SEM (mm³) (28th day) | TGI (%) |
|---|---|---|
| Vehicle (0.5% methyl cellulose solution) | 446 ± 36 | / |
| Cisplatin (1 mg/kg, intraperitoneal injection, twice a week) | 165 ± 22 | 85.9% |
| Hydrochloride of the compound 6 (1.5 mg/kg, oral administration once a day) | 187 ± 14 | 79.2% |
| Cisplatin (1 mg/kg, intraperitoneal injection, twice a week) + hydrochloride of the compound 6 (1.5 mg/kg, oral administration once a day) | 33 ± 13 | 126% |

Conclusion: The compounds of the present disclosure alone or in combination with the chemotherapy drug cisplatin have an excellent anti-tumor effect on the human small cell lung cancer NCI-H1417 xenograft tumor model.

What is claimed is:
1. A compound of formula (I), a stereoisomer thereof or a pharmaceutically acceptable salt thereof,

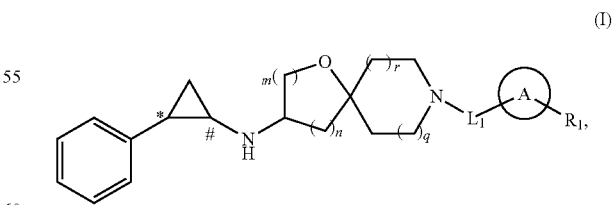

(I)

wherein,
$L_1$ is selected from —$(CH_2)g$-, —C(=O)—NH—, —C(=O)— and —C(=O)—O—;
$R_1$ is selected from H, CI, F, Br, I, OH, $NH_2$, CN, COOH, —C(=O)$NH_2$, $C_{1-6}$ alkyl, $C_{1-6}$alkoxyl, —C(=O)NH—$C_{1-6}$ alkyl and 5-6 membered heteroaryl, wherein the $C_{1-6}$ alkyl, $C_{1-6}$ alkoxyl, —C(=O)NH—$C_{1-6}$ alkyl and 5-6 membered heteroaryl are optionally substituted by 1, 2 or 3 $R_a$;

ring A is selected from $C_{6-10}$ aryl, 5-6 membered heteroaryl, $C_{3-8}$ cycloalkyl and 3-6 membered heterocycloalkyl;

$R_a$ is selected from F, Cl, Br, I, OH, $NH_2$, CN, COOH and $C_{1-3}$ alkyl;

m is 1 or 2;

n is 1;

r is 1;

q is 1;

g is 0, 1, 2 or 3;

each of the 5-6 membered heteroaryl and 3-6 membered heterocycloalkyl comprises 1, 2, 3 or 4 heteroatoms or heteroatomic groups independently selected from —NH—, —O—, —S— and N;

the carbon atom marked with "*" is a chiral carbon atom and exists in the form of (R) or (S) single enantiomer or enriched in one enantiomer;

the carbon atom marked with "#" is a chiral carbon atom and exists in the form of (R) or (S) single enantiomer or enriched in one enantiomer.

2. The compound or the pharmaceutically acceptable salt thereof as defined in claim 1, wherein $R_a$ is selected from F, Cl, Br, I, OH, $NH_2$, CN, COOH and —$CH_3$.

3. The compound or the pharmaceutically acceptable salt thereof as defined in claim 1, wherein $R_1$ is selected from H, Cl, F, Br, I, OH, $NH_2$, CN, COOH, —C(=O)$NH_2$, $C_{1-3}$ alkyl, $C_{1-3}$ alkoxyl, —C(=O)$NH_2$—$C_{1-3}$ alkyl and 5 membered heteroaryl, wherein the $C_{1-3}$ alkyl, $C_{1-3}$ alkoxyl, —C(=O)$NH_2$—$C_{1-3}$ alkyl and 5 membered heteroaryl are optionally substituted by 1, 2 or 3 $R_a$.

4. The compound, the stereoisomer thereof or the pharmaceutically acceptable salt thereof as defined in claim 3, wherein $R_1$ is selected from H, F, Cl, Br, I, OH, $NH_2$, CN, COOH, —C(=O)$NH_2$, —$CH_3$, —$OCH_3$ and tetrazolyl, wherein the —$CH_3$, —$OCH_3$ and tetrazolyl are optionally substituted by 1, 2 or 3 $R_a$.

5. The compound, the stereoisomer thereof, or the pharmaceutically acceptable salt thereof as defined in claim 4, wherein $R_1$ is selected from H, F, Cl, Br, I, OH, $NH_2$, CN, COOH, —C(=O)$NH_2$, —$CF_3$, —$OCH_3$, —$CH_2$—COOH and

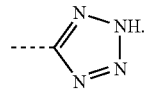

6. The compound, the stereoisomer thereof or the pharmaceutically acceptable salt thereof as defined in claim 1, wherein $L_1$ is selected from a single bond, —$CH_2$-, —$(CH_2)_2$-, —C(=O)—NH—, —C(=O)— and —C(=O)—O—.

7. The compound, the stereoisomer thereof or the pharmaceutically acceptable salt thereof as defined in claim 1, wherein ring A is selected from phenyl, naphthyl, tetrazolyl, pyridyl, pyrazinyl, cyclopropyl, cyclobutyl, cyclohexyl, bicyclo[2.2.2]octyl and azetidinyl.

8. The compound, the stereoisomer thereof or the pharmaceutically acceptable salt thereof as defined in claim 7, wherein ring A is selected from

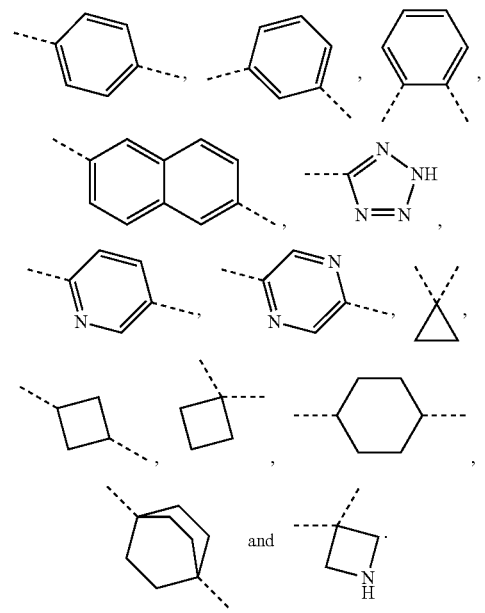

9. The compound, the stereoisomer thereof or the pharmaceutically acceptable salt thereof as defined in claim 1, wherein the compound is

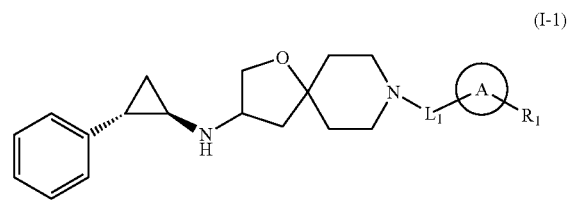

(I-1)

wherein, $R_1$, $L_1$ and ring A are as defined in claim 1.

10. The compound, the stereoisomer thereof or the pharmaceutically acceptable salt thereof as defined in claim 9, wherein the compound is selected from

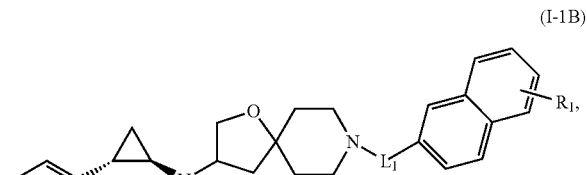

(I-1B)

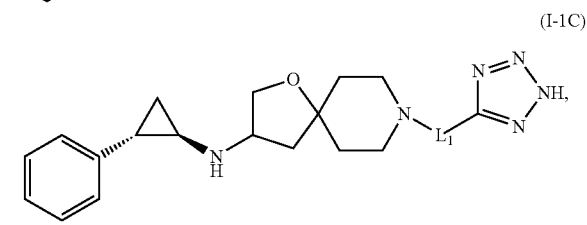

(I-1C)

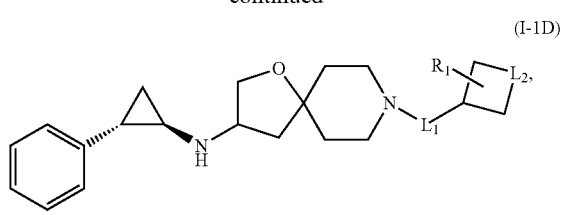
(I-1D)
wherein,
L₂ is selected from a single bond, —CH₂-, —(CH₂)₂-, —(CH₂)₃- and —NH.
11. A compound of the following formula, a stereoisomer thereof or a pharmaceutically acceptable salt thereof,
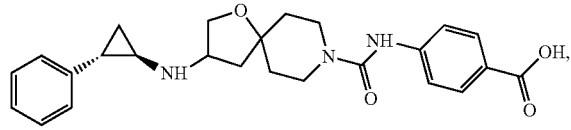
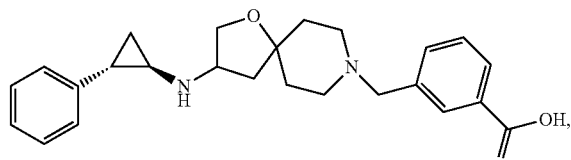
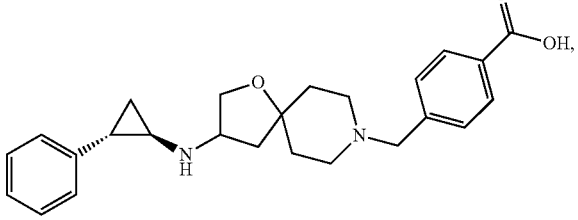
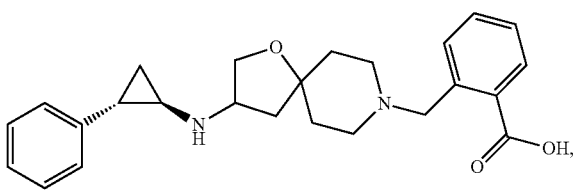
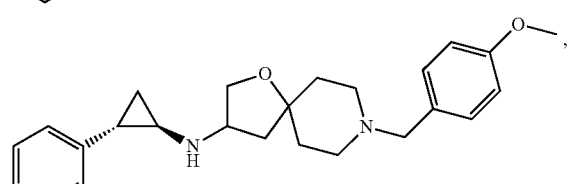
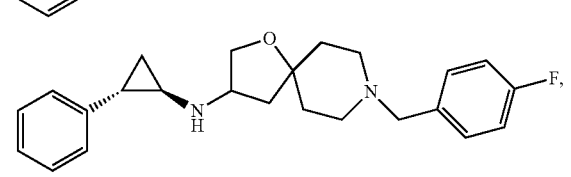
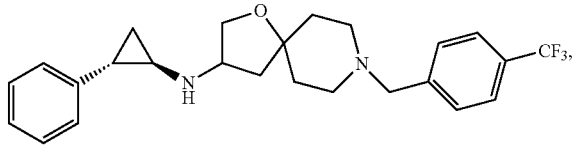
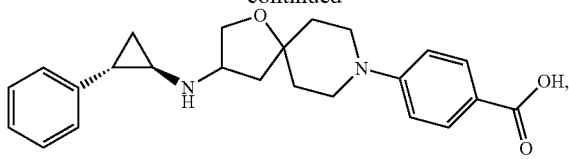
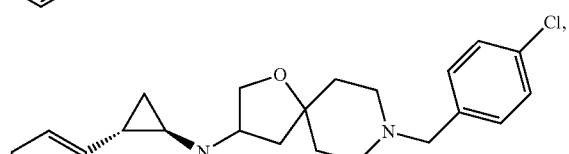
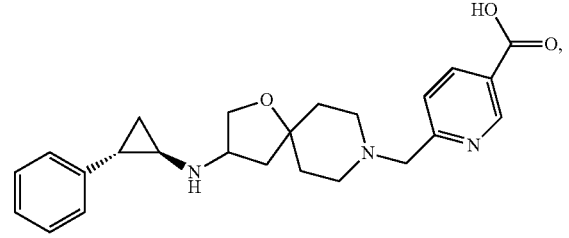
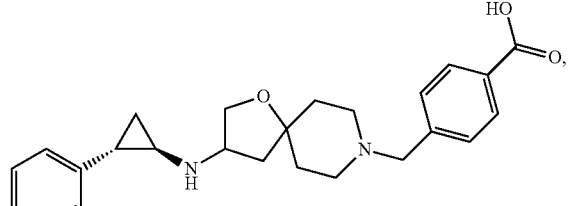
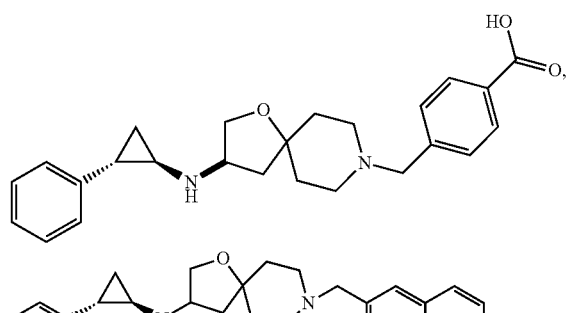
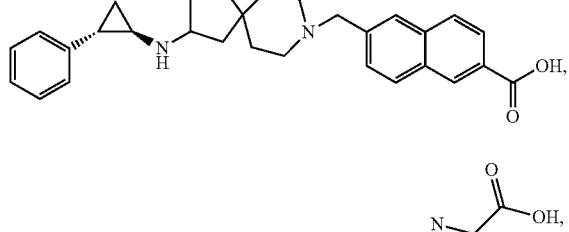
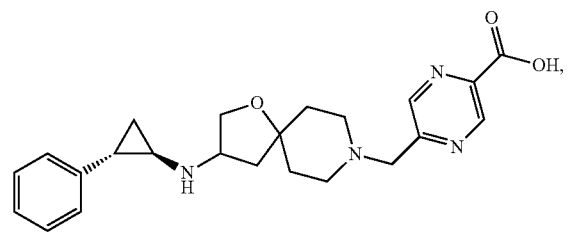

91
-continued
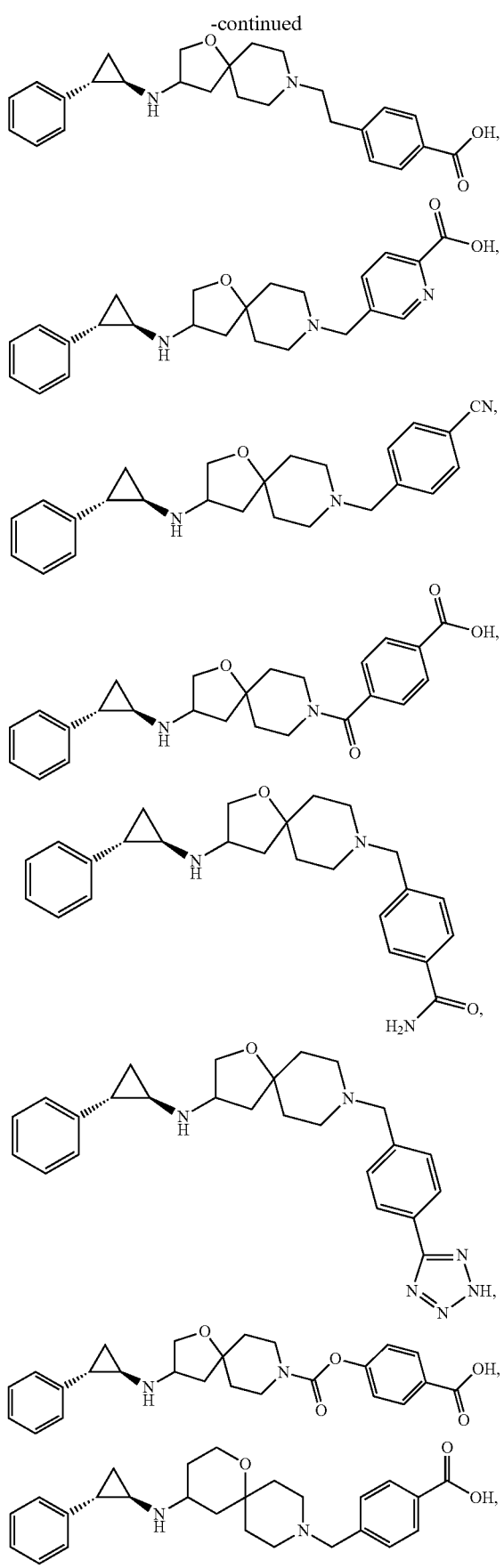
92
-continued
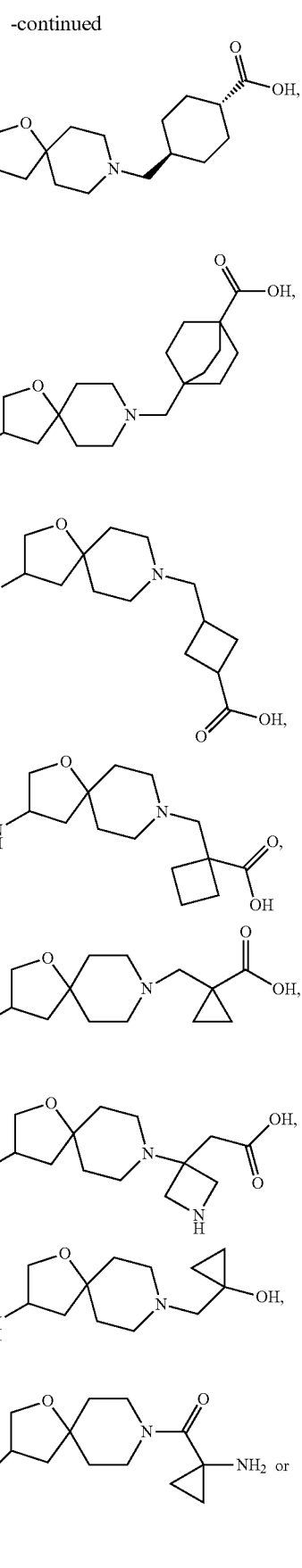

-continued

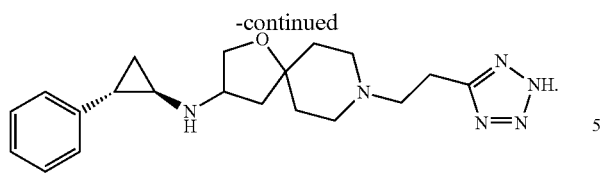

5

12. The compound, the stereoisomer thereof or the pharmaceutically acceptable salt thereof as defined in claim 1, wherein the salt is selected from hydrochloride.

13. A method for treating a disease associated with LSD1 in a subject in need thereof, comprising administering the compound, the stereoisomer thereof or the pharmaceutically acceptable salt thereof as defined in claim 1 to the subject.

14. The compound, the stereoisomer thereof or the pharmaceutically acceptable salt thereof as defined in claim 11, wherein the salt is selected from hydrochloride.

15. A method for treating a disease associated with LSD1 in a subject in need thereof, comprising administering the compound, the stereoisomer thereof or the pharmaceutically acceptable salt thereof as defined in claim 11 to the subject.

\* \* \* \* \*